(12) United States Patent
Gregory et al.

(10) Patent No.: US 7,803,808 B2
(45) Date of Patent: Sep. 28, 2010

(54) PRODUCTION OF POLYKETIDES AND OTHER NATURAL PRODUCTS

(75) Inventors: Matthew Alan Gregory, Nr Saffron Walden (GB); Christine Janet Martin, Nr. Saffron Walden (GB)

(73) Assignee: Wyeth LLC, Madison, NJ (US)

( * ) Notice: Subject to any disclaimer, the term of this patent is extended or adjusted under 35 U.S.C. 154(b) by 386 days.

(21) Appl. No.: 11/659,936

(22) PCT Filed: Aug. 11, 2005

(86) PCT No.: PCT/GB2005/003158

§ 371 (c)(1),
(2), (4) Date: Aug. 30, 2007

(87) PCT Pub. No.: WO2006/016167

PCT Pub. Date: Feb. 16, 2006

(65) Prior Publication Data

US 2009/0253732 A1 Oct. 8, 2009

(30) Foreign Application Priority Data

Aug. 11, 2004 (GB) .................. 0417852.1

(51) Int. Cl.
*C07D 498/18* (2006.01)
*A61K 31/436* (2006.01)
(52) U.S. Cl. .................. 514/291; 514/411; 540/456
(58) Field of Classification Search .................. 514/291, 514/411; 540/456
See application file for complete search history.

(56) References Cited

U.S. PATENT DOCUMENTS

| | | | |
|---|---|---|---|
| 3,929,992 A | 12/1975 | Sehgal et al. |
| 3,993,479 A | 11/1976 | Cheskis et al. |
| 4,439,196 A | 3/1984 | Higuchi et al. |
| 4,447,223 A | 5/1984 | Kaye et al. |
| 4,447,224 A | 5/1984 | DeCant, Jr. et al. |
| 4,486,194 A | 12/1984 | Ferrara |
| 4,487,603 A | 12/1984 | Harris et al. |
| 4,596,556 A | 6/1986 | Morrow et al. |
| 4,790,824 A | 12/1988 | Morrow et al. |
| 4,941,880 A | 7/1990 | Burns |
| 5,023,262 A | 6/1991 | Caufield et al. |
| 5,064,413 A | 11/1991 | McKinnon et al. |
| 5,109,112 A | 4/1992 | Siekierka et al. |
| 5,138,051 A | 8/1992 | Hughes et al. |
| 5,221,670 A | 6/1993 | Caufield |
| 5,312,335 A | 5/1994 | McKinnon et al. |
| 5,354,845 A | 10/1994 | Soldin |
| 5,362,718 A | 11/1994 | Skotnicki et al. |
| 5,378,836 A | 1/1995 | Kao et al. |
| 5,383,851 A | 1/1995 | McKinnon et al. |
| 5,391,730 A | 2/1995 | Skotnicki et al. |
| 5,399,163 A | 3/1995 | Peterson et al. |
| 5,432,183 A | 7/1995 | Schulte |
| 5,446,048 A | 8/1995 | Failli et al. |
| 5,457,182 A | 10/1995 | Wiederrecht et al. |
| 5,498,597 A | 3/1996 | Burakoff et al. |
| 5,563,145 A | 10/1996 | Failli et al. |
| 5,665,772 A | 9/1997 | Cottens et al. |
| 5,728,710 A | 3/1998 | Luengo |
| 5,763,590 A | 6/1998 | Peattie et al. |
| 5,912,253 A | 6/1999 | Cottens et al. |
| 5,955,457 A | 9/1999 | Lee et al. |
| 6,015,815 A | 1/2000 | Mollison |
| 6,670,168 B1 | 12/2003 | Katz et al. |

FOREIGN PATENT DOCUMENTS

| EP | 0 589 703 A | 3/1994 |
|---|---|---|
| WO | 94/09010 | 4/1994 |
| WO | 96/41807 | 12/1996 |
| WO | 98/01546 | 1/1998 |
| WO | 98/04279 | 2/1998 |
| WO | 98/54308 | 12/1998 |
| WO | WO 98/54308 | 12/1998 |
| WO | 00/00618 | 1/2000 |
| WO | 00/01827 | 1/2000 |

(Continued)

OTHER PUBLICATIONS

Alarcon, C.M., et al. Protein kinase activity and identification of a toxic effector domain of the target of rapamycin TOR proteins in yeast. Molecular Biology of the Cell, 10: 2531-2546 (1999).

(Continued)

*Primary Examiner*—Bruck Kifle
(74) *Attorney, Agent, or Firm*—Jennifer A. Kispert; Michael J. Herman

(57) ABSTRACT

The present invention relates to production of polyketides and other natural products and to libraries of compounds and individual novel compounds. Therefore in aspect the present invention provides 17-desmethylrapamycin and analogues thereof, methods for their production, including recombinant strains, and isolation and uses of the compounds of the invention. In a further aspect the present invention provides for the use of 17-desmethylrapamycin and analogues thereof in the induction or maintenance of immunosuppression, the stimulation of neuronal regeneration or the treatment of cancer, B-cell malignancies, fungal infections, transplantation rejection, graft vs. host disease, autoimmune disorders, diseases of inflammation vascular disease and fibrotic diseases, and in the regulation of wound healing.

14 Claims, 8 Drawing Sheets

FOREIGN PATENT DOCUMENTS

| WO | 01/03692 | 1/2001 |
|---|---|---|
| WO | 01/34816 | 5/2001 |
| WO | WO 01/34816 | 5/2001 |
| WO | 01/79520 | 10/2001 |
| WO | 01/87263 | 11/2001 |
| WO | 02/14482 | 2/2002 |
| WO | 03/033699 | 4/2003 |
| WO | 03/048375 | 6/2003 |
| WO | 03/070908 | 8/2003 |
| WO | 2004/007709 | 1/2004 |
| WO | WO 2004/007709 | 1/2004 |

OTHER PUBLICATIONS

Aparicio, J.F., et al. "Organization of the biosynthetic gene cluster for rapamycin in *Streptomyces hygroscopicus*: analysis of the enzymatic domains in the modular polyketide synthase." Gene, 169: 9-16 (1996).

Baker, H., et al. Rapamycin (AY-22,989), a new antifungal antibiotic. III. In vitro and in vivo evaluation. Journal of Antibiotics, 31: 539-545 (1978).

Balter, M. "Structural Biology: Protein Matchmaker May Lead New Gene Therapy to the Altar." Science, 273: 183 (1996).

Bierman, M., et al. "Plasmid cloning vectors for the conjugal transfer of DNA from *Escherichia coli* to *Streptomyces* spp." Gene, 116: 43-49 (1992).

Bisang, C., et al. "A chain initiation factor common to both modular and aromatic polyketide synthases." Nature, 401: 502-505 (1999).

Bohm, I., et al. "Engineering of a minimal modular polyketide synthase, and targeted alteration of the stereospecificity of polyketide chain extension." Chemistry and Biology, 5: 407-412 (1998).

Box, S.J., et al. 27-O-Demethylrapamycin, an immunosuppressant compound produced by a new strain of *Streptomyces hygroscopicus*. Journal of Antibiotics, 48: 1347-1349 (1995).

Brown, E.J., et al. "A mammalian protein targeted by G1-arresting rapamycin-receptor complex." Nature, 369: 756-758 (1994).

Brunn, G.J., et al. "Direct inhibition of the signalling functions of the mammalian target of rapamycin by the phosphoinositide 3-kinase inhibitors, wortmannin and LY294002." EMBO Journal, 15: 5256-5267 (1996).

Carlson, R.P., et al. Rapamycin, a potential disease-modifying antiarthritic drug. J. Pharmacol. Exp. Ther., 266(2): 1125-38 (1993).

Chambraud, B., et al. "FAP48, a mew protein that forms specific complexes with both immunophilins FKBP59 and FKBP12. Prevention by the immunosuppressant drugs FK506 and rapamycin." Journal of Biological Chemistry, 271: 32923-32929 (1996).

Chen, J., et al. Identification of an 11-kDa FKBP12-rapamycin-binding domain within the 289-kDa FKBP12-rapamycin-associated protein and characterization of a critical serine residue. Proc. Natl. Acad. Sci. USA, 92: 4947-4951 (1995).

Choi, J.W., et al. "Structure of the FKBP12-rapamycin complex interacting with the binding domain of human FRAP." Science, 273: 239-242 (1996).

Chung, L., et al. "Deletion of rapQNML from the rapamycin gene cluster of *Streptomyces hygroscopicus* gives production of the 16-O-desmethyl-27-desmethoxy analog." Journal of Antibiotics, 54: 250-256 (2001).

Corey, E.J., et al. "Enantioselective Synthesis of the C(18)-C(35) Segment of Immunosuppressant FK-506 Using Efficient New Methodology." Tetrahedron Letters, 30: 5235-5238 (1989).

Cortes, J., et al. "Repositioning of a domain in a modular polyketide synthase to promote specific chain cleavage." Science, 268: 1487-1489 (1995).

Del Vecchio, F., et al. Active-site residue, domain and module swaps in modular polyketide synthases. Journal of Industrial Microbiology and Biotechnology, 8: 489-494 (2003).

Dengler, W.A., et al. "Development of a propidium iodide flouescence assay for proliferation and cytotoxicity assay." Anti-cancer Drugs, 6: 522-532 (1995).

Dilella, A.G., et al. "Exon organization of the human FKBP-12 gene: correlation with structural and functional protein domains." Biochemistry, 30: 8512-8517 (1991).

Donadio, S., et al. "Modular organization of genes required for complex polyketide synthesis." Science, 252: 675-679 (1991).

Donadio, S., et al. "An erythromycin analog produced by reprogramming of polyketide synthesis." Proc. Natl. Acad. Sci. USA, 90: 7199-7123 (1993).

Dudkin, L., et al. "Biochemical correlates of mTOR inhibition by the rapamycin ester CCI-779 and tumor growth inhibition." Clin. Cancer Res., 7(6): 1758-64 (2001).

Dutton, C.J., et al. "Novel avermectins produced by mutational biosynthesis." Journal of Antibiotics, 44: 357-365 (1991).

Fehr, T., et al. "Antascomicinc A, B, C, D and E: Novel FKBP12 binding compounds from a *Micromonospora* strain." Journal of Antibiotics, 49(3): 230-233 (1996).

Feibig, H.H., et al. "Human tumor xenografts: Predictivity, characterization, and discovery of new anticancer agents. In: Fiebig HH, Burger AM (eds). Relevance of Tumor Models for Anticancer Drug Development." Contrib. Oncol., 54: 29-50 (1999).

Ferrari, S., et al. "The immunosuppressant rapamycin induces inactivation of P70s6k through dephosphorylation of a novel set of sites." Journal of Biological Chemistry, 268: 16091-16094 (1993).

Findlay, J.A., et al. "On the chemistry and high firld nuclear magnetic resonance spectroscopy of rapamycin." Canadian Journal of Chemistry, 58: 579 (1980).

Fishbein, T.M., et al. "Intestinal transplantation before and after the introduction of sirolimus." Transplantation, 73(10): 1538-42 (2002).

Foey, A., et al. "Cytokine-stimulated T cells induce macrophage IL-10 production dependent on phosphatidylinositol 3-kinase and p70S6K: implications for rheumatoid arthritis." Arthritis Res., 4(1): 64-70. Epub Oct. 10, 2001.

Galat, A. "Sequence diversification of the FK506-binding proteins in several different genomes." European Journal of Biochemistry, 267: 4945-4959 (2000).

Graziani, E.I., et al. "Novel sulphue-containing rapamycin analogs prepared by precursor-directed biosynthesis." Organic Letter, 5: 2385-2388 (2003).

Gregory, C.R., et al. "Rapamycin inhibits arterial intimal thickening caused by both alloimmune and mechanical injury. Its effect on cellular, growth factor and cytokine response in injured vessels." Transplantation, 55(6): 1409-1418 (1993).

Gregory, M.A., et al. "Integration site for *Streptomyces* phase ΦBT1 and the development of site-specific integrating vectors." Journal of Bacteriology, 185: 5320-5323 (2003).

Gregory, M.A., et al. "Isolation and characterization of pre-rapamycin, the first macrocyclic intermediate in the biosynthesis of the immunosuppressant rapamycin by *S. hygroscopicus*." Angewandte Chemie—International Edition, 43: 2551-2553 (2004).

Guba, M., et al. "Rapamycin inhibits primary and metastatic tumor growth by antiangiogenesis: involvement of vascular endothelial growth factor." Nature Medicine, 8: 128-135 (2002).

Hamilton, G.S., et al. "Immunophilins: Beyond immunosuppression." Journal of Medicinal Chemistry, 41: 5119-5143 (1998).

Hara, K., et al. "Regulation of eIF-4E BP1 phosphorylation by mTOR." Journal of Biological Chemistry, 272: 26457-26463 (1997).

Hardwick, J.S., et al. "Rapamycin-modulated transcription defines the subset of nutrient-sensitive signalling pathways directly controlled by Tor proteins." Proc. Natl. Acad. Sci. USA, 96: 14866-14870 (1999).

Hatanaka, H., et al. "FR-900520 and FR-900523, novel immunosuppressants isolated from a *Streptomyces*. II. Fermentation, isolation and physico-chemical and biological characteristics." Journal of Antibiotics (Tokyo), 41(11): 1592-601 (1988).

Hatanaka, H., et al. FK506 related compounds produced by *Streptomyces tsukubaensis* No. 9993. Journal of Antibiotics (Tokyo), 42(4): 620-2 (1989).

Hendrickson, B.A., et al. "Structural organization of the genes encoding human and murine FK506-binding protein (FKBP)13 and comparison to FKBP1" Gene, 134: 271-275 (1993).

Hentges, K.E., et al. "FRAP/mTOR is required for proliferation and patterning during embryonic developments in the mouse." Proc. Natl. Acad. Sci. USA, 98: 13796-13801 (2001).

Hung, D.T., et al. "cDNA cloning of a human 25 kDa FK506 and rapamycin binding protein." Biochemical and Biophysical Research Communications, 184: 733-738 (1992).

Hung, D.T., et al. "Understanding and controlling the cell cycle with natural products." Chemistry & Biology, 3: 623-639 (1996).

Hunziker, D., et al. "Primer unit specificity in rifamycin biosynthesis principally resides in the later stages of the biosynthetic pathway." J. Am. Chem. Soc., 12: 1092-1093 (1998).

Jain, S., et al. "Rapamycin reduces expression of fibrosis-associated genes in an experimental model of renal ischaemia reperfusion injury." Transplant Proc., 33(1-2): 556-8 (2001).

Jin, Y.J., et al. "Molecular cloning of a 25-kDa high affinity rapamycin binding protein, FKBP25." Journal of Biological Chemistry, 267: 10942-10945 (1992).

Kahan, B.D., et al. "Preclinical evaluation of new poten immunosuppressive agent, rapamycin." Tranplantation, 52: 185-191 (1991).

Kahan, B.D., et al. "Rapamycin: Clinical results and future opportunities." Transplantation, 72: 1181-1193 (2001).

Kallen, J.A., et al. "X-ray crystal structure of 28-O-methylrapamycin complexed with FKBP12: Is the cyclohexyl moiety part of the effector domain of rapamycin?" Journal of the American Chemical Society, 118: 5857-5861 (1996).

Kao, C.M., et al. "Engineered biosynthesis of a triketide lactone from an incomplete modular polyketide synthase." Journal of the American Chemical Society, 116: 11612-11613 (1994).

Kao, C.M., et al. "Manipulation of macrolide ring size by directed mutagenesis of a modular polyketide synthase." Journal of the American Chemical Society, 117: 9105-9106 (1995).

Kao, C.M., et al. "Engineered biosynthesis of structurally diverse tetraketides by a trimodular polyketide synthase." Journal of the American Chemical Society, 118: 9184-9185 (1996).

Kao, C.M., et al. "Gain of function metagenesis of the erythromycin polyketide synthase. 2. Engineered biosynthesis of eight-membered ring tetraketide lactone." Journal of the American Chemical Society, 119: 11339-11340 (1997).

Kawasome, H., et al. Targeted disruption of p70s6k defines its role in protein synthesis and rapamycin sensitivity. Proc. Natl. Acad. Sci. USA, 95: 5033-5038 (1998).

Khaw, L.E., et al. "Mutational biosynthesis of novel rapamycins by a strain of Streptomyces hygroscopicus NRRL 5491 disrupted in rapL, encoding a putative lysine cyclodeaminase." Journal of Bacteriology, 180: 809-814 (1998).

Kirby, B., et al. "Psoriasis: the future." British Journal of Dermatology, 144: 37-43 (2001).

Kirchner, G.I., et al. "Pharmacokinetics of SDZ RAD and cyclosporin including their metabolites in seven kidney graft patients after the first dose of SDZ RAD." British Journal of Clinical Pharmacology, 50: 449-454 (2000).

Konig, A., et al. "The pipecolate-incorporating enzyme for the biosynthesis of the immunosuppressant rapamycin. Nucleotide sequence analysis, disruption and heterologous expression of rapP from Streptomyces hygroscopicus." European Journal of Biochemistry, 247: 526-534 (1997).

Kuhstoss, S., et al. "Production of a novel polyketide through the constructions of a hybrid polyketide synthase." 183: 231-236 (1996).

Kunz, J., et al. "FAP1, a homologue of human transcription factor NF-X1, competes with rapamycin for binding to FKBP12 in yeast." Molecular Biology, 37: 1480-1493 (2000).

Kuo, C.J., et al. "Rapamycin selectively inhibits interleukin-2 activation of p70 66 kinase." Nature, 358: 70-73 (1992).

Lee, M.H., et al. "Site-specific integration of mycobacteriophage L5: integration-proficient vectors for Mycobacterium smegmatis, Mycobacterium tuberculosis, and bacille Calmetter-Guerin." Proc. Natl. Acad. Sci. USA, 88: 3111-5 (1991).

Liang, J., et al. "Refined structure of the FKBP12-rapamycin-FRB ternary complex at 2.2 A resolution." Acta Crystallographica Section D-Biological Crystallography, 55: 736-744 (1999).

Lumovskaya, N., et al. "Gene disruption and replacement in the rapamycin-producing Streptomyces hygroscopicus strain ATCC 29253." Microbiology-UK, 143: 875-883 (1997).

Lowden, P.A.,S., et al. "Origin and true nature of the starter unit for the rapamycin polyketide synthase." Angewandte Chemie—International Edition, 40(4): 777-779 (2001).

Lowden, P.A., et al. "New rapamycin derivatives by precursor-directed biosynthesis." ChemBioChem, 5: 535-538 (2004).

Luengo, J.I., et al. "Structure-Activity Studies of Rapamycin Analogs—Evidence That the C-7 Methoxy Group is Part of the Effector Domain and Positioned at the Fkbp12-Frap Interface." Chemistry & Biology, 2: 471-481 (1995).

Lyons, W.E., et al. "Immunosuppressant FK506 promotes neurite outgrowth in cultures of PC12 cells and sensory ganglia." Proc. Natl., Acad. Sci. USA, 91: 3191-3195 (1994).

Marshall, J.A., et al. "Synthesis of a C22-34 Subunit of the Immunosuppressant FK506." J. Org. Chem., 60 :7230-7237 (1995).

Matsuura, M., et al. The sre gene (ORF469) encodes a site-specific recombinase responsible for integration of the R4 phage genome. Journal of Bacteriology, 178(11): 3374-3376 (1996).

McAlpine, J., et al. "Revised NMR assignments for rapamycin." Journal of Antibiotics, 44: 688-690 (1991).

McDaniel, R., et al. "Multiple genetic modification of the erthromycin polyketide synthase to produce a library of novel 'unnatural' natural products." Proc. Natl. Acad. Sci., USA, 96: 1846-1851 (1999).

Molnar, I., et al. "Organisation of the biosynthetic gene cluster for rapamycin in Streptomyces hygroscopicus: analysis of genes flanking the polyketide synthase." Gene, 169: 1-7 (1996).

Morice, M.C., et al. RAVEL Study Group. "Randomized study with the Sirolimus-Coated Bx Velocity Balloon-Expandable Stent in the Treatment of Patients with de Novo Native Coronary Artery Lesions. A randomized comparison of a sirolimus-eluting stent with a standard stent for coronary revascularization." N. Eng. J. Med., 346(23): 1773-80 (2002).

McKatyn, T.M., et al. "The effects of rapamycin in murine peripheral nerve isograft and allografts." Plast. Reconstr. Surg., 109(7): 2405-17 (2002).

Nave, B.T., et al. "Mammalian target of rapamycin is a direct target for protein kinase B: identification of a convergence point for opposing effects of insulin and amino-acid deficiency on protein translation." Biochemical Journal, 344: 427-431 (1999).

Nishida, H., et al. "Generation of novel rapamycin structures by microbial manipulations." Journal of Antibiotics, 48: 657-666 (1995).

Olinyk, M., et al. "A hybrid modular polyketide synthase obtained by domain swapping." Chemistry & Biology, 3: 833-839 (1996).

Paget, M.S.B., et al. "Evidence that the extracytoplasmic function sigma factor σE required for normal cell wall structure in Streptomyces coelicolor A3(2)." Journal of Bacteriology, 181: 204-211 (1999).

Paiva, N.L., et al. "Incorporation of acetate, propinate, and methionine into rapamycin by Streptomyces hygroscopicus." Journal of Natural Products, 54: 157-177 (1991).

Paiva, N.L., et al. "The immediate precursor of the nitrogen-containing ring of rapamycin is free pipecolic acid." Enzyme and Microbial Technology, 15: 581-585 (1993).

Patterson, C.E., et al. "Developmental regulation of FKBP65. An ER-localized extracellular matrix binding-protein." Molecular Biology of the Cell, 11: 3925-3935 (2000).

Perin, E.C., et al. "Choosing a Drug-Eluting Stent: A Comparison Between CYPHER and TAXUS." Reviews in Cardiovascular Medicine, 6(suppl. 1): S13-S21 (2005).

Powell, N., et al. "The immunomodulatory drugs cyclosporin A, mycophenolate mofetil, and sirolimus (rapamycin) inhibit allergen-induced proliferation and IL-5 production by PBMCs from atopic asthmatic patients." J. Allergy Clin. Immunol., 108(6): 915-7 (2001).

Rabinovitch, A., et al. "Combination therapy with sirolimus and interleukin-2 prevents spontaneous and recurrent autoimmune diabetes in NOD mice." Diabetes, 51: 638-45 (2002).

Raught, B., et al. "The target of rapamycin (TOR) proteins." Proc. Natl. Acad. Sci. USA, 98: 7037-7044 (2001).

Reeves, C.D., et al. "Alteration of the substrate specificity of a modular polyketide synthase acyltransferase domain through site-specific mutations." Biochemistry, 40: 15464-15470 (2001).

Reid, R., et al. "A model of structure and catalysis for ketoreductase domains in modular polyketide synthases." Biochemistry, 42: 72-79 (2003).

Reitamo, S., et al. "Efficacy of sirolimus (rapamycin) administered concomitantly with a subtherapeutic dose of cyclosporin in the treatment of severe psoriasis: a randomized controlled trial." Br. J. Dermatol., 145(3): 438-45 (2001).

Rosen, M.K., et al. "Natural products as probes of cellular function: studies of immunophilins." Angewandte Chemie—International Edition in English, 31: 384-400 (1992).

Roth, T., et al. "Human tumor cell lines demonstrating the characteristic of patient tumors as useful models for anticancer drug screening." In: Feibig HH, Burger AM (eds.). Relevance of Tumor Models for Anticancer Drug Development. Contrib. Oncol., 54: 145-156 (1999).

Rowe, C.J., et al. "Construction of new vectors for high-level expression in actinomycetes." Gene, 216: 215-223 (1998).

Rowe, C.J., et al. "Engineering a polyketide with a longer chain by insertion of an extra module into the erythromycin-producing polyketide synthase." Chemistry & Biology, 8:475-485 (2001).

Roymans, D., et al. "Phosphatidylinositol 3-kinases in tumor progression." European Journal of Biochemistry, 268: 487-498 (2001).

Ruan, X., et al. "Acyltransferase domain substitutions in erythromycin polyketide synthase yield novel erythromycin derivatives." Journal of Bacteriology, 179: 6416-6425 (1997).

Salituro, G.M., et al. "Meridamycin: a novel nonimmunosuppressive FKBP12 ligand from *Streptomyces hygroscopicus*." Tetrahydron letters, 36: 997-1000 (1995).

Schreiber, S.L., et al. "The mechanism of action of cyclosporin A and FK506." Immunol. Today, 13: 136-142 (1992).

Schwecke, T., et al. "The biosynthetic gene cluster for the polyketide immunosuppressant rapamycin." Proc. Natl. Acad. Sci. USA, 92: 7839-7843 (1995).

Sedrani, R., et al. "Chemical modification of rapamycin: the discovery of SDZ RAD." Transplantation Proceedings, 30: 2192-2194 (1998).

Sehgal, R., et al. "Rapamycin (AY-22,989) a new antifungal antibiotic II. Fermentation, isolation and characterization." Journal of Antibiotics, 28: 727-733 (1975).

Shepherd, P.R., et al. "Phosphoinositide 3-kinase: the key switch mechanism in insulin signalling." Biochemical Journal, 333: 471-490 (1998).

Smovkina, T., et al. "Construction of a series of pSAM2-based integrative vectors for use in actinomycetes." Gene, 94: 53-59 (1990).

Stassi, D.L., et al. "Ethyl-substituted erythromycin derivatives produced by directed metabolic engineering." Proc. Natl. Acad. Sci. USA, 95: 7305-7309 (1998).

Staunton, J., et al. "Biosynthesis of Erythromycin and Rapamycin." Chem. Rev., 97: 2611: 2629 (1997).

Steiner, J.P., et al. "Neutrophic immunophilin ligands stimulate structural and functional recovery in neurodegenerative animal models." Proc. Natl. Acad. Sci. USA, 94: 2019-2024 (1997).

Tang, S. J., et al. "A rapamycin-sensitive signalling pathway contributes to long-term synaptic plasticity in the hippocampus." Proc. Natl. Acad. Sci. USA, 99(1): 467-472 (2002).

Van Duyne, G.D., et al. "Atomic structures of the human immunophilin FKBP-12 complexes with FK506 and rapamycin." Journal of Molecular Biology, 229: 105-124 (1993).

Van Mellaert, L., et al. "Site-specific integration of bacteriophage VXB genome in *Streptomyces venezuelae* and construction of a VXB-based integrative vector." Microbiology, 144: 3351-3358 (1998).

Vezina, C., et al. "Rapamycin (AY-22, 989), a new antifungal antibiotic. I. Taxonomy of the producing streptomycete and isolation of the active principle." Journal of Antibiotics, 28: 721-726 (1975).

Vilella-Bach, M., et al. "The FKBP12-rapamycin-binding domain is required for FKBP12-rapamycin-associated protein kinase activity and G1 progression." Journal of Biological Chemistry, 274: 4266-4272 (1999).

Waller, J.R., et al. "Molecular mechanisms of renal allograft fibrosis." British Journal of Surgery, 88: 1429-1441 (2001).

Warner, L.M., et al. "A modification of the in vivo mixed lymphocyte reaction and rapamycin's effect in this model." CLin. Immunol. Immunopathol., 64(3): 242-7 (1992).

Wilman, D.E.V. "Prodrugs in Cancer Chemotherapy." Biochemical Society Transactions, 14: 375-382 (315th Meeting, Belfast) (1986).

Wong, G.K., et al. "Antifungal activities of rapamycin and its derivatives, prolylramycin, 32-desmethylrapamycin, and 32-desnethozyrapamycin." Journal of Antibiotics, 51: 487-491 (1998).

Wu, K., et al. "The FK520 gene cluster of *Streptomyces hygroscopicus* var. *ascomyceticus* (ATCC 14891) contains genes for biosynthesis of unusual polyketide extender units." Gene, 251: 81-90 (2000).

Yem, A. W., et al. "The Hsp56 component of steroid receptor complexes binds to immobilized FK506 and shows homology to FKBP-12 and FKBP-13." Journal of Biological Chemistry, 267: 2868-2871 (1992).

Yin, J., et al. "Direct and Convenient Conversion of Alcohols to Flourides." Organic Letters, 6(9): 1465-1468 (2004).

Yu, K., et al. (mTOR, a novel target in breast cancer: the effect of CCI-779, an mTOR inhibitor, in preclinical models of breast cancer. Endocrine-Related Cancer, 8: 249-258 (2001).

Zhu, J., et al. "Rapamycin inhibits hepatic stellate cell proliferation in vitro and limits fibrogenesis in an in vivo model of liver fibrosis." Gastroenterology, 117(5): 1198-204 (1999).

Keiser, T., et al. "Chapter 1: General Introduction Actinomycete biology." Practical Streptomyces Genetics. John Innes Center (2000).

NCCLS Reference Method for Broth Dilution Antifungal Susceptibility Testing for Yeasts: Approved Standard M27-A, vol. 22, No. 15 (2002).

Khaw, LE. Ph.D. Dissertation, University of Cambridge. The Biosynthesis of Rapamycin. (1995).

Lowden, P.A.S. Ph.D. Dissertation, University of Cambridge. "Studies on the biosynthesis of rapamycin." (1997).

Reather, J.A. Ph.D. Dissertation, University of Cambridge. (2000).

↷ COSY correlation   ↷ TOCSY correlation   ↷ HMBC correlation

PRODUCTION OF POLYKETIDES AND OTHER NATURAL PRODUCTS

FIELD OF THE INVENTION

The present invention relates to production of polyketides and other natural products and to libraries of compounds and individual novel compounds. Therefore in one aspect the present invention provides 17-desmethylrapamycin and analogues thereof, methods for their production, including recombinant strains, and isolation and uses of the compounds of the invention. In a further aspect the present invention provides for the use of these novel rapamycin analogues in the induction or maintenance of immunosuppression, the stimulation of neuronal regeneration or the treatment of cancer, B-cell malignancies, fungal infections, transplantation rejection, graft vs. host disease, autoimmune disorders, diseases of inflammation, vascular disease and fibrotic diseases and in the regulation of wound healing. In a specific embodiment the present invention provides methods for the engineering of the biosynthetic genes governing production of rapamycin in order to generate engineered strains that produce 17-desmethylrapamycin and analogues thereof. The invention is also concerned with methods to generate a library of 17-desmethylrapamycin analogues by feeding non-natural starter acids to such a strain, and the library of compounds thus produced and with the generation of derivative strains in which cloned genes or gene cassettes are expressed to generate further analogues, and to processes for their preparation, and to means employed therein (e.g. nucleic acids, vectors, gene cassettes and genetically modified strains).

BACKGROUND OF THE INVENTION

Rapamycin (sirolimus) (FIG. 1) is a lipophilic macrolide produced by Streptomyces hygroscopicus NRRL 5491 (Sehgal et al., 1975; Vézina et al., 1975; U.S. Pat. Nos. 3,929,992; 3,993,749) with a 1,2,3-tricarbonyl moiety linked to a pipecolic acid lactone (Paiva et al., 1991). Other related macrolides (FIG. 2) include FK506 (tacrolimus) (Schreiber and Crabtree, 1992), FK520 (ascomycin or immunomycin) (Wu et al., 2000), FK525 (Hatanaka H, et al., 1989), FK523 (Hatanaka, H., et al., 1988), antascomicins (Fehr, T., et al., 1996) and meridamycin (Salituro et al., 1995). For the purpose of this invention rapamycin is described by the numbering convention of McAlpine et al. (1991) in preference to the numbering conventions of Findlay et al. (1980) or Chemical Abstracts (11$^{th}$ Cumulative Index, 1982-1986 p 60719CS).

The polyketide backbone of rapamycin is synthesised by head-to-tail condensation of a total of seven propionate and seven acetate units to a shikimate derived cyclohexanecarboxylic acid starter unit (Paiva et al., 1991). The L-lysine derived amino acid, pipecolic acid, is condensed via an amide linkage onto the last acetate of the polyketide backbone (Paiva et al., 1993) and is followed by lactonisation to form the macrocycle. A 107 kb genomic region containing the biosynthetic gene cluster has been sequenced (Schwecke et al., 1995). Analysis of the open reading frames revealed three large genes encoding the modular polyketide synthase (PKS) (Aparicio et al., 1996; Schwecke et al., 1995). Embedded between the PKS genes lies the rapP gene encoding a protein with sequence similarity to activation domains of nonribosomal peptide synthetases and it is thought to act analogously (König et al., 1997). The region encoding the PKS genes is flanked on both sides by 24 additional open reading frames encoding enzymes believed to be required for the biosynthesis of rapamycin (Molnár et al., 1996). These include the following post-polyketide modification enzymes: two cytochrome P-450 monooxygenases, designated as RapJ and RapN, an associated ferredoxin RapO, and three SAM-dependent O-methyltransferases RapI, RapM and RapQ. Other adjacent genes have putative roles in the regulation and the export of rapamycin (Molnár et al., 1996). The cluster also contains the gene rapL whose product RapL is proposed to catalyse the formation of the rapamycin precursor L-pipecolic acid through the cyclodeamination of L-lysine (Khaw et al., 1998; Paiva et al., 1993).

The polyketide core of rapamycin is assembled by the very large, multifunctional proteins that comprise the Type I polyketide synthase (rap PKS). This polypeptide complex comprises a loading module and fourteen extension modules, each module being responsible for both the addition of a specific acyl-CoA precursor to the growing polyketide chain, and for the degree of reduction of the β-keto carbonyl group. Each module performs several biochemical reactions which are carried out by specific domains of the polypeptide. All the extension modules contain an acyl transferase (AT) domain which selects and then donates the acyl group from a precursor to an acyl carrier protein (ACP) domain, and a β-ketosynthase (KS) domain that adds the pre-existing polyketide chain to the new acyl-ACP by decarboxylative condensation. Additional domains are present in some extension modules: β-ketoreductase (KR) domains which reduce β-keto groups to hydroxyls, dehydratase (DH) domains which act on hydroxyls to leave double bonds, and enoyl reductase (ER) domains which reduce double bonds to leave saturated carbons. In modules 3 and 6 the β-keto processing domains that are present are predicted to be inactive, as the action of these domains is not reflected in the ultimate structure. The final extension module (extension module 14) appears not to contain any β-keto-processing domains. The initiation of rapamycin biosynthesis occurs via incorporation of 4,5-dihydroxycyclohex-1-enecarboxylic acid that is derived from the shikimate pathway (Lowden, P. A. S., et al. 2001) and is common to other FKBP-binding molecules such as FK506 and FK520 (FIG. 2). Following biosynthesis of the polyketide, the NRPS module encoded by rapP, incorporates pipecolic acid (L-lysine derived), which is condensed via an amide linkage onto the last acetate of the polyketide backbone (Paiva et al., 1993). This is followed by lactonisation to form the macrocycle.

The nucleotide sequences for each of the three rapamycin PKS genes, the NRPS-encoding gene and the flanking late gene sequences and the corresponding polypeptides, are identified in Aparicio et al., 1996, and Schwecke et al., 1995 and are deposited with the NCBI under accession number X86780, and corrections to this sequence have recently been published in WO 04/007709.

The first enzyme-free product of the rapamycin biosynthetic cluster has been designated pre-rapamycin (WO 04/007709, Gregory et al., 2004). Production of the fully processed rapamycin requires additional processing of the polyketide/NRPS core by the enzymes encoded by the rapamycin late genes, RapJ, RapN, RapO, RapM, RapQ and RapI.

Rapamycin has significant pharmacological value due to the wide spectrum of activities exhibited by the compound; this emphasizes the necessity to generate novel analogues of the drug. Rapamycin shows moderate antifungal activity, mainly against Candida species but also against filamentous fungi (Baker et al., 1978; Sehgal et al., 1975; Vézina et al., 1975; U.S. Pat. Nos. 3,929,992; 3,993,749). Rapamycin inhibits cell proliferation by targeting signal transduction pathways in a variety of cell types, e.g. by inhibiting signalling pathways that allow progression from the $G_1$ to the S-phase of the cell cycle (Kuo et al., 1992). In T cells rapamycin inhibits signalling from the IL-2 receptor and subsequent autoproliferation of the T cells resulting in immunosuppression. The inhibitory effects of rapamycin are not limited to T cells, since rapamycin inhibits the proliferation of many mammalian cell types (Brunn et al., 1996). Rapamycin is, therefore, a potent immunosuppressant with established or predicted therapeutic applications in the prevention of organ allograft rejection and in the treatment of autoimmune diseases (Kahan et al., 1991). 40-O-(2-hydroxy)ethyl-rapamycin (SDZ RAD, Certican, everolimus) is a semi-synthetic analogue of rapamycin that shows immunosuppressive pharmacological effects (Sedrani, R. et al., 1998; Kirchner et al., 2000; U.S. Pat. No. 5,665,772). Approval for this drug was obtained for Europe in 2003 and it is expected to be launched in the US shortly. The rapamycin ester CCI-779 (Wyeth-Ayerst) inhibits cell growth in vitro and inhibits tumour growth in vivo (Yu et al., 2001). CCI-779 is currently in Phase III clinical trials. The value of rapamycin in the treatment of chronic plaque psoriasis (Kirby and Griffiths, 2001), the potential use of effects such as the stimulation of neurite outgrowth in PC12 cells (Lyons et al., 1994), the block of the proliferative responses to cytokines by vascular and smooth muscle cells after mechanical injury (Gregory et al., 1993) and its role in prevention of allograft fibrosis (Waller and Nicholson, 2001) are areas of intense research (Kahan and Camardo, 2001). Recent reports reveal that rapamycin is associated with a lower incidence of cancer in organ allograft patients on long-term immunosuppressive therapy than those on other immunosuppressive regimes, and that this reduced cancer incidence is due to inhibition of angiogenesis (Guba et al., 2002). It has been reported that the neurotrophic activities of immunophilin ligands are independent of their immunosuppressive activity (Steiner et al., 1997) and that nerve growth stimulation is promoted by disruption of the mature steroid receptor complex as outlined in the patent application WO 01/03692. Side effects such as hyperlipidemia and thrombocytopenia as well as potential teratogenic effects have been reported (Hentges et al., 2001; Kahan and Camardo, 2001).

Rapamycin impacts signalling cascades within the cell through the inhibition of the $p70^{S6k}$ kinase, a serine/threonine kinase in higher eukaryotes that phosphorylates the ribosomal protein S6 (Ferrari et al., 1993; Kuo et al., 1992). The S6 protein is located in the ribosomal 40S subunit and it is believed to be an important functional site involved in tRNA and mRNA binding. A regulatory function for mRNA translation through S6 phosphorylation by $p70^{S6k}$ has been postulated (Kawasome et al., 1998). Rapamycin inhibits protein synthesis through its effect on other growth related events, including the activity of cyclin-dependent kinases, phosphorylation of cAMP-responsive element modulator (CREM) and phosphorylation of the elongation factor binding protein 4E-BP1 (PHAS1) (Hung et al., 1996). The drug induces the accumulation of the dephosphorylated species of 4E-BP1 that binds to the translation initiation factor eIF-4E, thus, suppressing translation initiation of cap-dependent mRNAs (Hara et al., 1997; Raught et al., 2001).

The pharmacologic actions of rapamycin characterised to date are believed to be mediated by the interaction with cytosolic receptors termed FKBPs or immunophilins. Immunophilins (this term is used to denote immunosuppressant binding proteins) catalyse the isomerisation of cis and trans peptidyl-proline bonds and belong to a highly conserved family of enzymes found in a wide variety of organisms (Rosen and Schreiber, 1992). Two large groups of enzymes belonging to the family of immunophilins are represented by FKBPs and cyclophilins (Schreiber and Crabtree, 1992). The major intracellular rapamycin receptor in eukaryotic T-cells is FKBP12 (DiLella and Craig, 1991) and the resulting complex interacts specifically with target proteins to inhibit the signal transduction cascade of the cell. Analysis of the crystal structure of the FKBP12-rapamycin complex has identified a rapamycin-binding pharmacophore termed the 'binding domain' (Van Duyne et al., 1993) (see FIG. 1). The 'binding domain' is required for the interaction with the immunophilin and consists of the C-1 to C-14 region including the ester linkage, the pipecolic acid-derived ring, the dicarbonyl and the hemiketal ring. The interaction is characterised by many hydrophobic contacts and some hydrogen bonds including one to the hydroxyl group on the cyclohexane ring. The pipecolinyl ring (C2 to N7) makes the deepest penetration into the protein where it is surrounded by highly conserved aromatic amino acid residues lining the hydrophobic binding cavity. Both the C1 and the C8 carbonyl groups are involved in hydrogen bonding and the C9 carbonyl group protrudes into a pocket formed by three completely conserved aromatic amino acid residues (one tyrosine and two phenylalanine acid residues) in FKBP12. The domain of the immunophilin-ligand complex which interacts with the target proteins projects away from FKBP.

Most immunophilins do not appear to be directly involved in immunosuppressive activities and relatively little is known concerning their natural ligands although candidates for natural ligands of the FKBPs termed FKBP-associated proteins (FAP) such as FAP48 and FAP1 have been reported. The specific interaction of FAPs with FKBPs during the formation of complexes was prevented by rapamycin in a dose-dependent manner (Chambraud et al., 1996; Kunz et al., 2000). Immunophilins appear to function in a wide range of cellular activities such as protein folding; assembly and trafficking of proteins; co-regulation of molecular complexes including heat shock proteins; steroid receptors; ion channels; cell-to-cell interactions and transcription and translation of genes (Galat 2000; Hamilton and Steiner 1998). All immunophilins possess the protein folding property of peptidyl-prolyl cis-trans isomerisation and several immunophilins are found located in the endoplasmic reticulum, a principal site of protein synthesis in the cell. In addition to FKBP12 (U.S. Pat. No. 5,109,112) other immunophilins include FKBP12.6 (U.S. Pat. No. 5,457,182), FKBP13 (Hendrickson et al., 1993; U.S. Pat. No. 5,498,597), FKBP25 (Hung and Schreiber, 1992; Jin et al., 1992), FKBP14.6 (U.S. Pat. No. 5,354,845), FKBP52 (U.S. Pat. No. 5,763,590), FKBP60 (Yem et al., 1992) and FKBP65 (Patterson et al., 2000).

The target of the rapamycin-FKBP12 complex has been identified in yeast as TOR (target of rapamycin) (Alarcon et al., 1999) and the mammalian protein is known as FRAP (FKBP-rapamycin associated protein) or mTOR (mammalian target of rapamycin) (Brown et al., 1994). These proteins show significant similarity to the phosphotransferase domains of phosphatidylinositol 3-kinases and the observation that a point mutation in the FKBP12-rapamycin binding domain (FRB) of mTOR abolishes mTOR kinase activity provides evidence for the involvement of FRB in the function of the kinase domain (Vilella-Bach et al., 1999). The crystal structure of FKBP12-rapamycin with a truncated form of mTOR containing the FRB domain (Chen et al., 1995) has been obtained thus defining the 'effector' domain of rapamycin (Choi et al., 1996; Liang et al., 1999). The analysis of the crystal structure revealed that protein-protein contacts are relatively limited compared to the interaction between rapamycin and each protein. No hydrogen bonds between rapamycin and FRB were identified. Interaction is concentrated in a series of hydrophobic contacts between the triene region of rapamycin and mainly aromatic residues of FRB (Liang et al., 1999). The most deeply buried atom of rapamycin is the methyl attached to C23 (see FIG. 1). The C23 to C34 region and the cyclohexyl ring of rapamycin make hydrophobic contacts with FRB. A small conformational change in rapamycin was evident between the binary and the ternary complexes (Liang et al., 1999).

Divergences between the biological effects of rapamycin analogues modified at the C16 methoxy group and their ability to bind FKBP12 were detected and the location of the C16 substituents at the interfacial space between FKBP12 and mTOR was postulated (Luengo et al., 1995). The analysis of the crystal structure of FKBP12 with the non-immunosuppressive 28-O-methyl rapamycin revealed a significant difference in the orientation of the cyclohexyl ring which may result in disruption of mTOR binding (Kallen et al., 1996).

A link between mTOR signalling and localized protein synthesis in neurons; its effect on the phosphorylation state of proteins involved in translational control; the abundance of components of the translation machinery at the transcriptional and translational levels; control of amino acid permease activity and the coordination of the transcription of many enzymes involved in metabolic pathways have been described (Raught et al., 2001). Rapamycin sensitive signalling pathways also appear to play an important role in embryonic brain development, learning and memory formation (Tang et al., 2002). Research on TOR proteins in yeast also revealed their roles in modulating nutrient-sensitive signalling pathways (Hardwick et al., 1999). Similarly, mTOR has been identified as a direct target for the action of protein kinase B (akt) and of having a key role in insulin signalling (Shepherd et al., 1998; Navé et al., 1999). Mammalian TOR has also been implicated in the polarization of the actin cytoskeleton and the regulation of translational initiation (Alarcon et al., 1999). Phosphatidylinositol 3-kinases, such as mTOR, are functional in several aspects of the pathogenesis of tumours such as cell-cycle progression, adhesion, cell survival and angiogenesis (Roymans and Slegers, 2001).

The multitude of the FKBP's which are present in different cell types also underline the utility of isolating novel FKBP-ligand analogues with potentially changed binding and/or effector domains. For example, it is the inhibition of the rotamase enzyme FKBP52, which forms part of the steroid receptor complex, which has been identified as the mechanism by which rapamycin analogues (and other FKBP12-binding compounds) moderate neural regeneration and neurite outgrowth (WO 01/03692)

Pharmacokinetic studies of rapamycin and rapamycin analogues have demonstrated the need for the development of novel rapamycin compounds that may be more stable in solution, more resistant to metabolic attack and/or have improved bio-availability. Modification of rapamycin using the chemically available positions has been extensively addressed (see below). However this approach is restricted to the few sites available for chemical modification and is further limited in its utility by difficulties in selective modification at a particular position in the presence of other reactive sites on the molecule.

A range of synthesised rapamycin analogues using the chemically available sites of the molecule has been reported. The description of the following compounds was adapted to the numbering system of the rapamycin molecule described in FIG. 1. Chemically available sites on the molecule for derivatisation or replacement include C40 and C28 hydroxyl groups (e.g. U.S. Pat. Nos. 5,665,772; 5,362,718), C39 and C16 methoxy groups (e.g. WO 96/41807; U.S. Pat. No. 5,728, 710), C32, C26 and C9 keto groups (e.g. U.S. Pat. Nos. 5,378,836; 5,138,051; 5,665,772). Hydrogenation at C17, C19 and/or C21, targeting the triene, resulted in retention of antifungal activity but relative loss of immunosuppression (e.g. U.S. Pat. Nos. 5,391,730; 5,023,262). Significant improvements in the stability of the molecule (e.g. formation of oximes at C32, C40 and/or C28, U.S. Pat. Nos. 5,563,145, 5,446,048), resistance to metabolic attack (e.g. U.S. Pat. No. 5,912,253), bioavailability (e.g. U.S. Pat. Nos. 5,221,670; 5,955,457; WO 98/04279) and the production of prodrugs (e.g. U.S. Pat. Nos. 6,015,815; 5,432,183) have been achieved through derivatisation. However, chemical modification requires significant quantities of rapamycin template and, as a base and acid labile compound, it is difficult to work with. While chemical derivatisation can be group selective, it can often be difficult to be site selective. Consequently, chemical modification often requires multiple protective and deprotective steps and can produce mixed products in variable yields.

Biological approaches to producing novel rapamycin analogues were initially slow to be productive due to the difficulties encountered in working with the producing organism (Lomovskaya et al., 1997; Kieser et al., 2000) despite the availability of the sequence of the biosynthetic gene cluster of rapamycin from S. hygroscopicus (Aparicio et al., 1996; Schwecke et al., 1995). A recent patent application from the present inventors describes a wider range of rapamycin analogues than had been previously accessible via modification of the rapamycin biosynthetic pathway by manipulation of the post PKS modifying genes (WO 04/007709). Further analogues can also be accessed by feeding alternatives to the natural starter acid of the rapamycin PKS which are incorporated into the rapamycin structures (WO 04/007709). While these methods provide access to significantly more of the chemical space around the rapamycin molecule, this technology does not allow the modification of the core framework of the rapamycin molecule that is encoded by the type I polyketide synthase genes.

The isolation of rapamycin analogues using other biological methods such as biotransformation and phage-based genetic modification has also been described. Isolation of minor metabolites from both mutant strains and rapamycin producing strains has provided small quantities of a number of rapamycin analogues. These strains are often low yielding and produce mixtures of rapamycin analogues. The isolation of 27-O-desmethylrapamycin and 27-desmethoxyrapamycin was reported from the culture supernatant of S. hygroscopicus NCIMB 40319 (Box et al., 1995). The antifungal activity of 27-O-desmethylrapamycin was lower than that of rapamycin but the inhibition of FKBP12 PPlase activity seemed to be increased. The inhibition of ConA-stimulated proliferation of murine splenic T cells and the inhibition of LPS-stimulated proliferation of murine splenic B cells was decreased when compared to rapamycin (Box et al., 1995). Similarly, antifungal activities of the rapamycin analogues prolylrapamycin, 27-O-desmethylrapamycin and 27-desmethoxyrapamycin (numbering system of the rapamycin molecule as described in FIG. 1) were lower than that of rapamycin (Wong et al., 1998). Rapamycin analogues (16-O-desmethylrapamycin, 27-O-desmethylrapamycin, 39-O-desmethylrapamycin, 16,27-O-bisdesmethylrapamycin, prolylrapamycin, 26-O-desmethylprolylrapamycin, 9-deoxorapamycin, 27-desmethoxyrapamycin, 27-desmethoxy-39-O-desmethylrapamycin, 9-deoxo-27-desmethoxyrapamycin, 28-dehydrorapamycin, 9-deoxo-27-desmethoxy-39-O-desmethylrapamycin) were also isolated from *Actinoplanes* sp N902-109 after the addition of cytochrome P450 inhibitors and/or precursor feeding to the culture or after biotransformation of isolated rapamycin (Nishida et al., 1995). The use of such inhibitors, however, only allows the targeting of a particular enzyme function and is not site selective thus often resulting in mixtures of products. Rational production of a single selected analogue is not possible via this method. The resulting production of mixtures of rapamycin analogues rather than a single desired product also impacts yield. The mixed lymphocyte reaction (MLR) inhibitory activity of the compounds was assessed and little effect on the activity was detected after the loss of the methyl group at C27 or/and C16. A more significant decrease in activity was observed for 9-deoxorapamycin; additionally, the loss of the methoxy group at C27, the hydroxy group at C28 and the substitution of a pipecolic acid-derived group with a prolyl group all resulted in a reduction in potency (Nishida et al., 1995). Similarly, biotransformation of rapamycin and the isolation of 16,39-O-bisdesmethylrapamycin have been reported (WO 94/09010). The retention of some inhibitory activity in cell proliferation assays with compounds modified in the cyclohexyl ring, e.g. 39-O-desmethylrapamycin and C40 modifications such as SDZ RAD and CCI-779, identify this region of the molecule as a target for the generation of novel rapamycin analogues both with immunosuppressive and anti-cancer properties.

Novel rapamycin analogues have been reported after feeding cyclohexanecarboxylic acid, cycloheptanecarboxylic acid, cyclohex-1-enecarboxylic acid, 3-methylcyclohexanecarboxylic acid, cyclohex-3-enecarboxylic acid, 3-hydroxycyclohex-4-enecarboxylic acid and cyclohept-1-enecarboxylic acid to cultures of rapamycin-producing wild type S. hygroscopicus thus demonstrating the flexibility in the loading module of the rapamycin polyketide synthase (P. A. S. Lowden, Ph.D dissertation, University of Cambridge, 1997; Lowden et al., 2004). These novel rapamycin analogues were produced in competition with the natural starter, 4,5-dihydroxycyclohex-1-enecarboxylic acid, resulting in reduced yields and mixed products.

Two novel sulphur-containing rapamycin analogues of rapamycin have been isolated by feeding cultures of the rapamycin-producing S. hygroscopicus NRRL5491 with (±) nipecotic acid, to inhibit L-pipecolic acid production, and co-feeding the sulphur-containing pipecolate analogues (S)-1,4-thiazane-3 carboxylic acid or (S)-1,4-thiazane-4 carboxylic acid (Graziani et al., 2003).

The isolation of two recombinant S. hygroscopicus strains producing various rapamycin analogues, using biological methods mediated by phage technology (Lomovskaya et al., 1997), has been reported. In the presence of added proline analogues, a S. hygroscopicus rapL deletion mutant synthesized the novel rapamycin analogues prolylrapamycin, 4-hydroxyprolylrapamycin and 4-hydroxyprolyl-26-desmethoxy-rapamycin (Khaw et al., 1998). Similarly, the novel rapamycins 3-hydroxy-prolyl-rapamycin, 3-hydroxy-prolyl-26-desmethoxy-rapamycin, and trans-3-aza-bicyclo[3,1,0]hexane-2-carboxylic acid rapamycin have been identified from fed cultures of the same mutant strain as described in WO 98/54308. The activity of prolylrapamycin and 4-hydroxyprolyl-26-desmethoxy-rapamycin was assessed in proliferation assays and the inhibitory activity of the latter compound was significantly less than that of rapamycin (Khaw et al., 1998). The deletion of the five contiguous genes, rapQONML (responsible for post-polyketide modifications at C16, C27 and production of L-pipecolic acid) and their replacement with a neomycin resistance marker in S. hygroscopicus ATCC29253 using phage-based methodology resulted in the production of 16-O-desmethyl-27-desmethoxyrapamycin when fed with pipecolic acid (Chung et al., 2001). No complementation of this deletion mutant has been demonstrated. Furthermore, the site-specificity of neither RapM nor RapQ was identified in this work; therefore, rational design of rapamycin analogues requiring methylation at C16-OH or C27-OH was not enabled by Chung et al. (2001). The phage-based methodology suffers from a number of drawbacks, as described in more detail below, exemplified by the reported production of only three recombinant S. hygroscopicus strains over a period of 9 years from the disclosure of the gene sequence. It offers a difficult and protracted process of obtaining engineered strains and is significantly more limited in utility in comparison to the methodology disclosed within the earlier application by the present inventors (WO 04/007709).

Conventional approaches to manipulate rapamycin modifying genes using biological methods comprise the mutation or deletion of individual genes in the chromosome of a host strain or/and the insertion of individual genes as extra copies of homologous or heterologous genes either individually or as gene cassettes (WO 01/79520, WO 03/048375). However, the isolation of novel rapamycin analogues using such biological methods has been limited due to the difficulties in transforming the rapamycin-producing organism S. hygroscopicus. It has been reported that the commonly used methods of transformation with plasmid DNA or conjugal transfer were unsuccessful with the rapamycin producing strain (Lomovskya et al., 1997, Schwecke et al., 1995, Kieser et al., 2000). The state of the art prior to the disclosure of WO 04/007709 used the methodology of Lomovskya et al. (1997), a work intensive phage based method that is severely limited by the size of the cloned DNA fragments transferred into S. hygroscopicus (Kieser et al., 2000). This technology is limited to the transfer of a maximum of approximately 6.4 kbp of cloned DNA. Thus, when complementing a deletion mutant using this technology the artisan is limited to the inclusion of genetic material within this size limit, for example complementation is limited to two typical functional genes (usually approximately 1 kbp each in size) in addition to a desired promoter, regions of homology (if required) and resistance marker. WO 04/007709 disclosed the first description of recombinant technology methods for the efficient transformation of strain such as *Streptomyces hygroscopicus* subsp. *hygroscopicus* NRRL5491 that contains a rapamycin biosynthetic gene cluster. Prior to this, although the genetic information for the rapamycin biosynthetic gene cluster has been available since 1995 (Schwecke et al., 1995), limited progress in this area had hitherto been made (Khaw et al., 1998; Chung et al., 2001; WO 01/34816). WO 04/007709 describes methods for manipulating the rapamycin biosynthetic pathway and producing a number of rapamycin analogues by complementation of a deletion mutant in which the amount of post-PKS processing is specifically varied, and optionally feeding exogenous starter acids to strains in which at least rapK has been deleted or inactivated.

Previous work has demonstrated that polyketide synthase (PKS) genes can, in principle, be manipulated with the objective of providing novel polyketides. These alterations include:

Deletions: In-frame deletion of the DNA encoding part of the KR domain in module 5 of the erythromycin-producing (ery) PKS in *Saccharopolyspora erythraea* has been shown to lead to the formation of erythromycin analogues, namely 5,6-dideoxy-3-α-mycarosyl-5-oxo-erythronolide B and 5,6-dideoxy-5-oxoerythronolide B (Donadio et al., 1991).

Inactivation of individual domains: alteration of active site residues in the ER domain of module 4 of the ery PKS, by genetic engineering of the corresponding PKS-encoding DNA and its introduction into *Saccharopolyspora erythraea*, led to the production of 6,7-anhydroerythromycin C (Donadio et al., 1993).

Loading module swaps: WO 98/01546 discloses replacement of the loading module of the ery PKS with the loading module from the avermectin (ave) PKS, to produce a hybrid Type I PKS gene that incorporates different starter units to make novel erythromycin analogues. A hybrid tylactone load/platenolide polyketide synthase was generated (Kuhstoss et al., 1996) which successfully transferred the specificity of the tylactone loading module for methylmalonyl-CoA to the platenolide molecule. The elucidation of the function of $KS^Q$ (Bisang et al., 1999) and manipulation of $KS^Q$-containing loading modules is disclosed in WO 00/00618. Loading module swaps in the spinosyn biosynthetic pathway have also been described in WO 03/070908.

AT swaps: Oliynyk et al., (1996) and WO 98/01546 describe an AT domain swap where the erythromycin module 1 AT was replaced by the AT domain of rapamycin module 2 and the specificity of module 1 for the extender unit was altered accordingly. Further AT domain swaps have been described, for example in the erythromycin polyketide synthase (WO 98/01546, Ruan et al., 1997; Stassi et al., 1998) and in the spinosyn polyketide synthase (WO 03/070908).

Reductive Loop Swaps: for example alterations in the amount of reductive processing of the β-keto group formed during each condensation are described in WO 98/01546, WO 00/01827 and Kao et al., (1997).

Combinations of the domain swap approaches are exemplified in McDaniel et al., (1999).

Site-directed mutagenesis: WO 02/14482, Reeves et al., (2001), Reid et al., (2003) and Del Vecchio et al., (2003) demonstrate that it is possible to affect the substrate specificity of AT domains by selected mutation of specified residues.

Ring contraction: for example using an incomplete modular polyketide synthase (Kao et al. 1994) or moving the erythromycin chain terminating thioesterase domain downstream of modules 1, 2, 3, 5 or 6 (Cortés et al., 1995; Kao et al., 1995; Kao et al., 1996; Böhm et al., 1998) of the erythromycin PKS lead to the production of the expected truncated erythromycin molecules.

Ring expansion: insertion of a rapamycin module into the first ORF of the erythromycin PKS between erythromycin PKS modules 1 and 2 lead to production of the expected 16-membered macrolide (Rowe et al., 2001).

Modifications of PKS clusters are not limited to those described above.

However, it has also been found that not all manipulations of PKS genes are capable of producing the predicted new analogues. When Donadio et al., (1993) inactivated an enoyl reductase (ER) domain of the erythromycin PKS, the resulting anhydro-analogue was not completely processed because it was no longer a substrate for the mycarose-O-methyltransferase. Similarly, changing the polyketide starter unit prevented complete elongation and elaboration of a rifamycin analogue in *Amycolatopsis mediterranei* (Hunziker et al., 1998).

If rapamycin analogues could be made by engineering the polyketide synthase genes in the biosynthetic cluster they would be highly desirable because they are predicted to have interesting biological activity.

The sequence of the rapamycin biosynthetic cluster was first published in 1995 (Schwecke et al.; Aparicio et al., 1996). Despite the wealth of prior art regarding the manipulation of PKSs described above there have to date been no reports of successful polyketide engineering of the core polyketide synthase of the rapamycin cluster. *S. hygroscopicus*, the rapamycin producer, is a difficult organism to manipulate (Lomovskaya et al., 1997).

A host cell which has been modified to produce 17-desmethylrapamycin is claimed in U.S. Pat. No. 6,670,168, however this patent lacks any description or working example of how this compound could be made, other than the hypothesis that such a strain could be constructed by the substitution of the AT domain of module 10. The fact that a substitution at this position could hypothetically lead to 17-desmethylrapamycin was obvious to any person of skill in the art, but it is not apparent how such a substitution could be made in light of the difficulties highlighted above, and no teaching to this effect was provided in U.S. Pat. No. 6,670,168. In light of the known difficulties of working with *S. hygroscopicus* and in the absence of any detailed description of how such a recombinant host strain could be generated it is clear that this is merely a description of what these authors hoped to achieve rather than being an enabling disclosure of such a strain. Additionally, U.S. Pat. No. 6,670,168 does not provide any teaching to a person of skill in the art regarding how 17-desmethylrapamycin could be prepared or isolated. The state of the art regarding the biosynthesis of rapamycin analogues is limited to WO 04/007709 in which the genes encoding post PKS modifying enzymes are manipulated and related applications which describe the feeding of exogenous starter acids for incorporation into rapamycin. The general lack of progress in engineering the PKS of rapamycin is due to the technological difficulties in transformation of the producing organism *S. hygroscopicus* NRRL5491.

The present invention is concerned with the generation of 17-desmethylrapamycin and analogues thereof. Accessing 17-desmethylrapamycin analogues requires the engineering of the rapamycin PKS. It is not obvious within the current state of the art that it is possible to achieve the engineering required to produce such a strain. In the present invention the initial target is the engineering of *S. hygroscopicus* MG2-10. *S. hygroscopicus* MG2-10 produces pre-rapamycin when fed with the exogenous acid 3,4-dihydroxycyclohexanecarboxylic acid as disclosed in WO 04/007709 and Gregory et al., (2004). Engineering of this organism was performed to generate an engineered strain which produces 17-desmethylpre-rapamycin when fed with the exogenous acid 3,4-dihydroxycyclohexanecarboxylic acid. The current state of the art teaches how such a strain may be used in further experiments as a base strain for complementation by late gene cassettes (WO 04/007709) and/or as a base strain for feeding exogenous acids (WO 04/007709) and generating further rapamycin analogues, but does not teach how such a strain may be generated in *S. hygroscopicus* by PKS engineering. The present invention describes, surprisingly, the successful application of PKS engineering methodologies, similar to those described in Oliynyk et al., 1996, to the rapamycin PKS. This is an unexpected result as these recombinant DNA technologies have not previously been successfully applied to *S. hygroscopicus*. The generation of a strain for production of 17-desmethylpre-rapamycin analogues is a useful base strain for complementation by late gene cassettes (WO 04/007709) and/or as a base strain for feeding exogenous acids (WO 04/007709). Each of these rapamycin analogues can then further be modified by semi-synthesis. This is the first demonstration of a truly combinatorial method which may be used to generate a library of rapamycin analogues may be altered at one or more of: the PKS engineering level, the auxiliary gene level, starter acid incorporation, amino acid incorporation and further at the accessible chemical functionality on the molecule, which remains accessible to semi-synthesis.

SUMMARY OF THE INVENTION

In one aspect the present invention provides 17-desmethylrapamycin and analogues thereof, in particular, the present invention provides 17-desmethylrapamycin analogues according to the following formula:

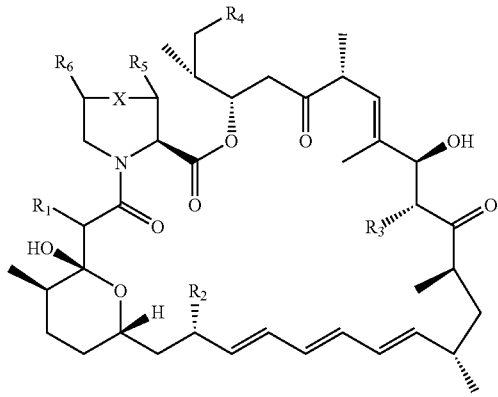

wherein:
x represents a direct bond, —CH$_2$—, —S—CH$_2$—, —CH$_2$—S— or —S(=O)—CH$_2$—;
or —CHR$_5$-x-CHR$_6$— represents

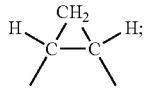

R$_1$ represents =O or (H,H);
R$_2$ represents OH or OMe;
R$_3$ represents H, OH or OMe;
R$_4$ represents a structural fragment selected from groups A, B, C, D, E and F,

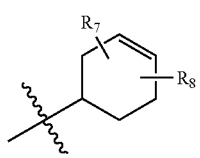 A

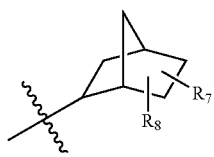 B

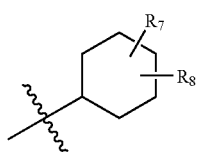 C

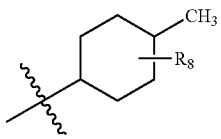 D

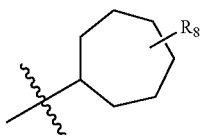 E

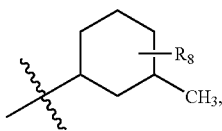 F in which
the wavy line indicates the position of attachment of the fragment,
R$_7$ represents H, OH or OMe and
R$_8$ represents H, OH, OMe, halo, thiol or C$_{1-4}$ alkyl;
or R$_4$ alternatively represents a 5- to 7-membered heterocycle containing one or more heteroatoms selected from the group consisting of O, S and N, which heterocycle is optionally substituted with one or more substituents selected from C$_{1-4}$ alkyl, OH, F and Cl; and
R$_5$ and R$_6$ are each independently H or OH,
or pharmaceutically acceptable derivatives thereof.

In a further aspect the present invention provides libraries of 17-desmethylrapamycin analogues generated using the methods of the present invention.

The novel rapamycin analogues are useful directly, and as templates for further semi-synthesis or bioconversion, to produce compounds useful as immunosuppressants, antifungal agents, anticancer agents, anti-inflammatory agents, neuroregenerative agents or agents for the treatment of transplantation rejection, graft vs. host disease, autoimmune disorders, vascular disease and fibrotic diseases or agents for use in the regulation of wound healing.

In a further aspect the present invention provides for the use of 17-desmethylrapamycin or an analogue thereof in medicine. In a further aspect the present invention provides for the use of 17-desmethylrapamycin or an analogue thereof in the preparation of a medicament for the induction or maintenance of immunosuppression, the stimulation of neuronal regeneration or the treatment of cancer, B-cell malignancies, fungal infections, transplantation rejection, graft vs. host disease, autoimmune disorders, diseases of inflammation, vascular disease or fibrotic diseases, or in the regulation of wound healing.

In one embodiment, 17-desmethylrapamycin or an analogue thereof, is used in combination therapy for the induction or maintenance of immunosuppression, the stimulation of neuronal regeneration or the treatment of cancer, B-cell malignancies, fungal infections, transplantation rejection, graft vs. host disease, autoimmune disorders, diseases of inflammation, vascular disease or fibrotic diseases, or in the regulation of wound healing.

The present invention also provides a pharmaceutical composition comprising 17-desmethylrapamycin or an analogue thereof, or a pharmaceutically acceptable salt together with a pharmaceutically acceptable carrier.

In a further aspect the present invention also provides a method for the production of 17-desmethylrapamycin or an analogue thereof said method comprising
(a) replacing the methylmalonyl-CoA specific AT domain of module 10 of the rapamycin PKS with a malonyl-CoA-specific AT domain,
(b) expressing the engineered rapamycin PKS in a suitable host cell
(c) culturing the host cell under conditions such that 17-desmethylrapamycin or an analogue thereof is produced including optionally supplying exogenous precursors
(d) optionally isolating the compound thus produced.

In a preferred embodiment the malonyl-CoA specific AT domain is selected from one of the following clusters: rapamycin, monensin, spinosyn, FK506, erythromycin, FK520, amphotericin, angolamycin, tylosin, 'hyg', FK523, meridamycin, antascomicin, FK525 and tsukubamycin. In a more preferred embodiment the malonyl-CoA specific AT domain is selected from one of the following clusters: rapamycin, monensin and FK506. In a more highly preferred embodiment the AT domain is selected from the group consisting of rapamycin module 2, monensin module 3, monensin module 6, monensin module 8, FK506 module 3 and FK506 module 7. In the most highly preferred embodiment the malonyl-CoA specific AT domain is from module 2 of rapamycin.

One skilled in the art will appreciate that this transformation could be attempted with any of a number of malonyl-CoA selective acyl transferase domains from any type I PKS or mixed NRPS/PKS. One skilled in the art will also appreciate that incorporation of malonyl-CoA by the module 10 AT could be effected by mutating the native rap AT10 to alter its specificity, for example using the methods as described in WO 02/14482, or by replacing the entire of module 10 with a module that contains an AT domain which is selective for malonyl-CoA, said module includes a natural module and a combinatorial module.

In an additional aspect, the present invention provides a method for generating a recombinant strain that contains a biosynthetic cluster that encodes an engineered rapamycin polyketide synthase where the methylmalonyl-CoA specific AT domain of module 10 has been replaced with a malonyl-CoA specific AT domain. In a preferred embodiment the malonyl-CoA specific AT domain is selected from one of the following PKS clusters: rapamycin, monensin, FK506, erythromycin, FK520, amphotericin, angolamycin, tylosin, 'hyg', FK523, meridamycin, antascomicin, FK525 and tsukubamycin. In a more preferred embodiment the malonyl-CoA specific AT domain is selected from one of the following clusters: rapamycin, monensin, FK506. In a more highly preferred embodiment the AT domain is selected from the group consisting of rapamycin module 2, monensin module 3, monensin module 6, module 8, FK506 module 3 and FK506 module 7. In the most highly preferred embodiment the malonyl-CoA specific AT domain is from module 2 of rapamycin.

Although engineering of the rapamycin polyketide synthase pathway has been exemplified herein in *S. hygroscopicus* MG2-10 (the generation of which is disclosed in WO 04/007709 and Gregory et al., (2004)) a person of skill in the art will appreciate that these methods can equally be applied to wild-type *S. hygroscopicus* NRRL5491 and other related strains. Preferably the engineered strain is selected from the group consisting of *S. hygroscopicus* MG2-10 and *S. hygroscopicus* NRRL 5491.

An embodiment of the previous aspects of the invention providing a method for the production of 17-desmethylrapamycin and analogues thereof and a method of generating a recombinant strain that contains a biosynthetic cluster that encodes an engineered rapamycin polyketide synthase, comprises the additional steps of:
(a) isolating the AT to be introduced as a single DNA fragment with suitable flanking restriction sites,
(b) amplifying and isolating the regions of DNA sequence homologous to the flanking sequences of the target AT using appropriate restriction sites,
(c) ligating the three DNA fragments as described in (a) and (b) together to give an in-frame sequence of LHS homology followed by donor AT domain followed by RHS homology,
(d) introducing the complete sequence from (c) into a vector for introduction into the host strain to give the final plasmid, said plasmid comprising:
 i) the oriT for conjugation,
 ii) one or more resistance markers,
 iii) a temperature sensitive origin of replication such that integrants can be selected by culturing at 37° C., and
 iv) an *E. coli* origin of replication
(e) transforming the host strain by conjugation using the final plasmid as described in (d) above,
(f) selecting the transformants by resistance to the relevant antibiotic,
(g) generating the primary integrants by culturing at 37° C. with antibiotic selection,
(h) screening the secondary recombinants by growth in the absence of antibiotic selection, also at 37° C.,
(i) identifying the desired strain by its ability to produce the target product and
(j) optionally confirming the genetics of the strain by standard methods.

In another aspect the present invention provides a method for making a 17-desmethylrapamycin analogue, said method comprising:
(a) generating a recombinant strain in which the methylmalonyl-CoA specific AT domain of module 10 of the rapamycin PKS has been replaced with a malonyl-CoA specific AT domain, and;
(b) feeding non-natural starter acids to a culture of said recombinant strain under conditions suitable for polyketide production, and
(c) optionally isolating the compound thus produced.

Therefore, the present invention provides a method for generating 17-desmethylrapamycin analogues which have incorporated non-natural starter acids. In a preferred embodiment the recombinant strain has had rapK deleted or inactivated. In a further preferred embodiment, the recombinant strain has had rapK deleted or inactivated and the non-natural starter acid fed to this strain is selected from the group consisting of cyclohexanecarboxylic acid, 3-methylcyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid.

In one embodiment the strain is not a recombinant *S. hygroscopicus* host cell that produces 17-desmethylrapamycin. In a further embodiment the strain is not a recombinant *S. hygroscopicus* host cell that produces 17-desmethylrapamycin in the absence of the provision of exogenous precursors.

In a further aspect, the present invention provides a method for generating a 17-desmethylrapamycin analogue, said method comprising:
(a) generating a recombinant strain in which the methylmalonyl-CoA specific AT domain of module 10 of the rapamycin PKS has been replaced with a malonyl-CoA specific AT domain (as described in more detail above),
(b) additionally deleting or inactivating one or more rapamycin auxiliary genes selected from rapI, rapJ, rapK, rapL, rapM, rapN, rapO and rapQ,
(c) culturing the strain thus obtained, optionally in the presence of an exogenous precursor if required, to produce the 17-desmethylrapamycin analogue, and
(d) optionally isolating the compound thus produced.

In an alternative preferred embodiment the auxiliary genes that have been deleted are rapI, rapJ and rapQ. In an alternative preferred embodiment the auxiliary genes that have been deleted are rapJ, rapM and rapQ.

In a further aspect, the present invention provides a method for generating a 17-desmethylrapamycin analogue, said method comprising:
(a) generating a recombinant strain in which the methylmalonyl-CoA specific AT domain of module 10 of the rapamycin PKS has been replaced with a malonyl-CoA specific AT domain (as described in more detail above),
(b) additionally deleting or inactivating one or more rapamycin auxiliary genes selected from rapI, rapJ, rapK, rapL, rapM, rapN, rapO and rapQ,
(c) re-introducing all or a subset of auxiliary genes in-trans to complement or partially complement the deletion,
(d) culturing the strain thus obtained, optionally in the presence of an exogenous precursor if required, to produce the 17-desmethylrapamycin analogue, and
(e) optionally isolating the compound thus produced.

In a preferred embodiment, in step (b) all the rapamycin auxiliary genes are deleted or inactivated. In a further preferred embodiment the recombinant strain is genetically complemented with one or more auxiliary genes selected from the group consisting of rapI, rapJ, rapK, rapL, rapM, rapN, rapO and rapQ or homologues thereof. In a specific embodiment the strain is complemented with all the auxiliary genes. In a further preferred embodiment the recombinant strain is genetically complemented with the auxiliary genes rapK, rapM, rapN, rapO and rapL or homologues thereof. In an alternative preferred embodiment the recombinant strain is genetically complemented with the rapamycin auxiliary genes rapK, rapI, rapN, rapO and rapL or homologues thereof.

In a further aspect of the invention, the above modifications are combined, therefore the present invention provides a method for making a 17-desmethylrapamycin analogue, said method comprising:
(a) generating a recombinant strain in which the methylmalonyl-CoA specific AT domain of module 10 of the rapamycin PKS has been replaced with a malonyl-CoA specific AT domain,
(b) additionally deleting or inactivating one or more rapamycin auxiliary genes selected from rapI, rapJ, rapK, rapL, rapM, rapN, rapO and rapQ,
(c) optionally re-introducing all or a subset of auxiliary genes in-trans to complement or partially complement the deletion,
(d) feeding non-natural starter acids to said recombinant strain under suitable conditions for the production of polyketides, and
(e) optionally isolating the compound thus produced.

In a preferred embodiment, the auxiliary gene(s) which have been deleted or inactivated include rapK.

In a preferred embodiment, in step (b) all the rapamycin auxiliary genes are deleted or inactivated. In a specific aspect the present invention provides an alternative method for generating 17-desmethylrapamycin analogues with non-natural starter acids by genetically complementing the recombinant strain in which all the rapamycin auxiliary genes have been deleted or inactivated with the rapamycin auxiliary genes rapI, rapJ, rapL, rapM, rapN, rapO and rapQ or their homologues, this generates a strain containing all auxiliary genes except rapK, and feeding with exogenous starter acids. In a preferred embodiment the exogenous non-natural starter acid is cyclohexanecarboxylic acid. In an alternative preferred embodiment the non-natural starter acid is 3-methylcyclohexanecarboxylic acid. In an alternative preferred embodiment the non-natural starter acid is cycloheptanecarboxylic acid. In an alternative preferred embodiment the non-natural starter acid is selected from the group consisting of 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid.

In a further embodiment, the present invention provides a method for generating 17-desmethylrapamycin analogues with combinations of auxiliary gene activities and non-natural starter acids. In a preferred embodiment the auxiliary genes that have been deleted are rapK, rapM and rapQ and the non-natural starter acid fed to this strain is cyclohexanecarboxylic acid. In an alternative preferred embodiment the non-natural starter acid fed to this strain with deleted rapK, rapM and rapQ is 3-methylcyclohexanecarboxylic acid. In an alternative preferred embodiment the non-natural starter acid fed to this strain with deleted rapK, rapM and rapQ is cycloheptanecarboxylic acid. In a preferred embodiment the auxiliary genes that have been deleted are rapK, rapM and rapQ and the non-natural starter acid fed to this strain is selected from the group consisting of 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid.

In a further preferred embodiment the auxiliary genes that have been deleted are rapK, rapI and rapQ and the non-natural starter acid fed to this strain is selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the auxiliary genes that have been deleted are rapK, rapI and rapQ and the non-natural starter acid fed to this strain is 3-methylcyclohexanecarboxylic acid. In a more highly preferred embodiment the auxiliary genes that have been deleted are rapK, rapI and rapQ and the non-natural starter acid fed to this strain is cyclohexanecarboxylic acid.

In an alternative preferred embodiment the auxiliary genes that have been deleted are rapK and rapM and the non-natural starter acid fed to this strain is selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the non-natural starter acid fed is cyclohexanecarboxylic acid.

In a further alternative preferred embodiment, the auxiliary genes that have been deleted are rapK, rapI and rapM and the non-natural starter acid fed to this strain is selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the non-natural starter acid fed is cyclohexanecarboxylic acid.

In an alternative preferred embodiment, the auxiliary genes that have been deleted are rapK, rapI, rapJ and rapQ and the non-natural starter acid fed to this strain is selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the non-natural starter acid fed is cyclohexanecarboxylic acid.

In an alternative preferred embodiment, the auxiliary genes that have been deleted are rapK, rapJ, rapM and rapQ and the non-natural starter acid fed to this strain is selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the non-natural starter acid fed is cyclohexanecarboxylic acid.

In a further embodiment the present invention provides a method for generating 17-desmethylrapamycin analogues by genetically complementing a recombinant strain in which all of the rapamycin auxiliary genes have been deleted or inactivated with one or more auxiliary genes selected from rapI, rapJ, rapK, rapL, rapM, rapN, rapO and rapQ or their homologues in combination with feeding natural or non-natural starter acids. In a preferred embodiment said recombinant strain is genetically complemented with rapI, rapJ, rapN, rapO and rapL and fed with a non-natural starter acid selected from the group consisting of cyclohexanecarboxylic acid, 3-methylcyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a preferred embodiment said recombinant strain is genetically complemented with rapJ, rapN, rapO and rapL and fed with a non-natural starter acid selected from the group consisting of cyclohexanecarboxylic acid, 3-methylcyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid.

In an alternative preferred embodiment said recombinant strain is genetically complemented with rapJ, rapM, rapN, rapO and rapL and fed a starter acid selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the starter acid fed is with 3-methylcyclohexanecarboxylic acid.

In an alternative preferred embodiment said recombinant strain is genetically complemented with rapI, rapJ, rapN, rapO, rapQ and rapL and fed with a starter acid selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the starter acid fed is cyclohexanecarboxylic acid.

In an alternative preferred embodiment said recombinant strain is genetically complemented with rapJ, rapN, rapO, rapQ and rapL and fed with a starter acid selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the starter acid fed is cyclohexanecarboxylic acid.

In an alternative preferred embodiment said recombinant strain is genetically complemented with rapM, rapN, rapO and rapL and fed with a starter acid selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the starter acid fed is cyclohexanecarboxylic acid.

In an alternative preferred embodiment said recombinant strain is genetically complemented with rapI, rapN, rapO and rapL and fed with a starter acid selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the starter acid fed is cyclohexanecarboxylic acid.

In a further aspect, the present invention provides a method for generating a library of 17-desmethylrapamycin analogues, said method comprising:

(a) generating a recombinant strain in which the methylmalonyl-CoA specific AT domain of module 10 of the rapamycin PKS has been replaced with a malonyl-CoA specific AT domain, (b) optionally deleting or inactivating one or more rapamycin auxiliary genes selected from rapI, rapJ, rapK, rapL, rapM, rapN, rapO and rapQ, (c) optionally re-introducing all or a subset of the rapamycin auxiliary genes in-trans to complement or partially complement the deletion, (d) feeding an array of non-natural starter acids to a production culture of said recombinant strain to generate a number of 17-desmethylrapamycin analogues, (e) feeding natural or novel amino acids to a production culture of said recombinant strain under suitable conditions such that polyketides are produced, (f) optionally isolating the compound thus produced and (g) optionally performing semi-synthesis on the rapamycin analogues isolated.

These and other embodiments of the invention are described in more detail in the following description, the examples and claims set forth below.

DEFINITIONS

Figure 1:
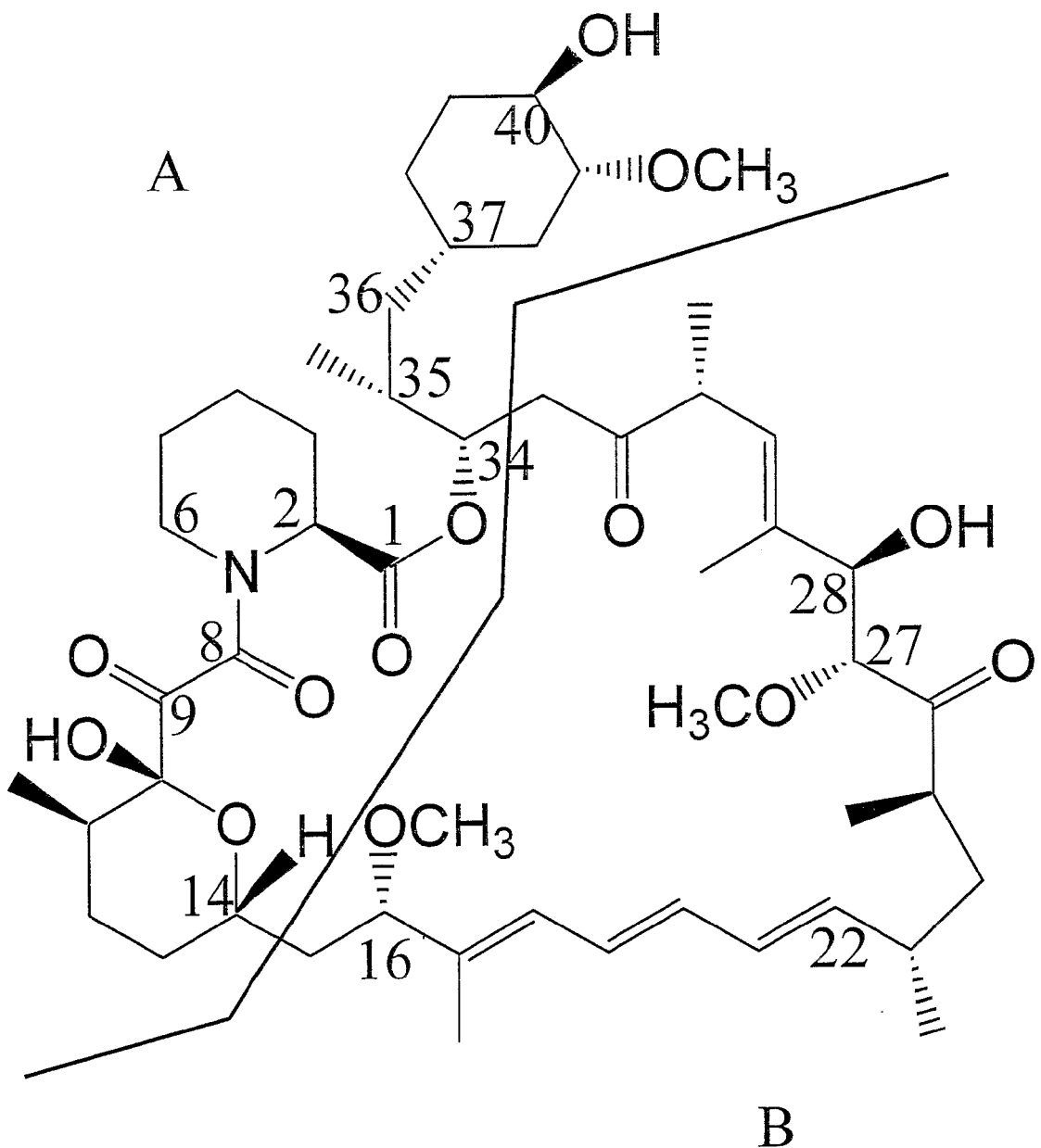
FIG. 1 Structure of rapamycin: A is the 'binding domain, and B is the 'effector domain'.
Figure 2:
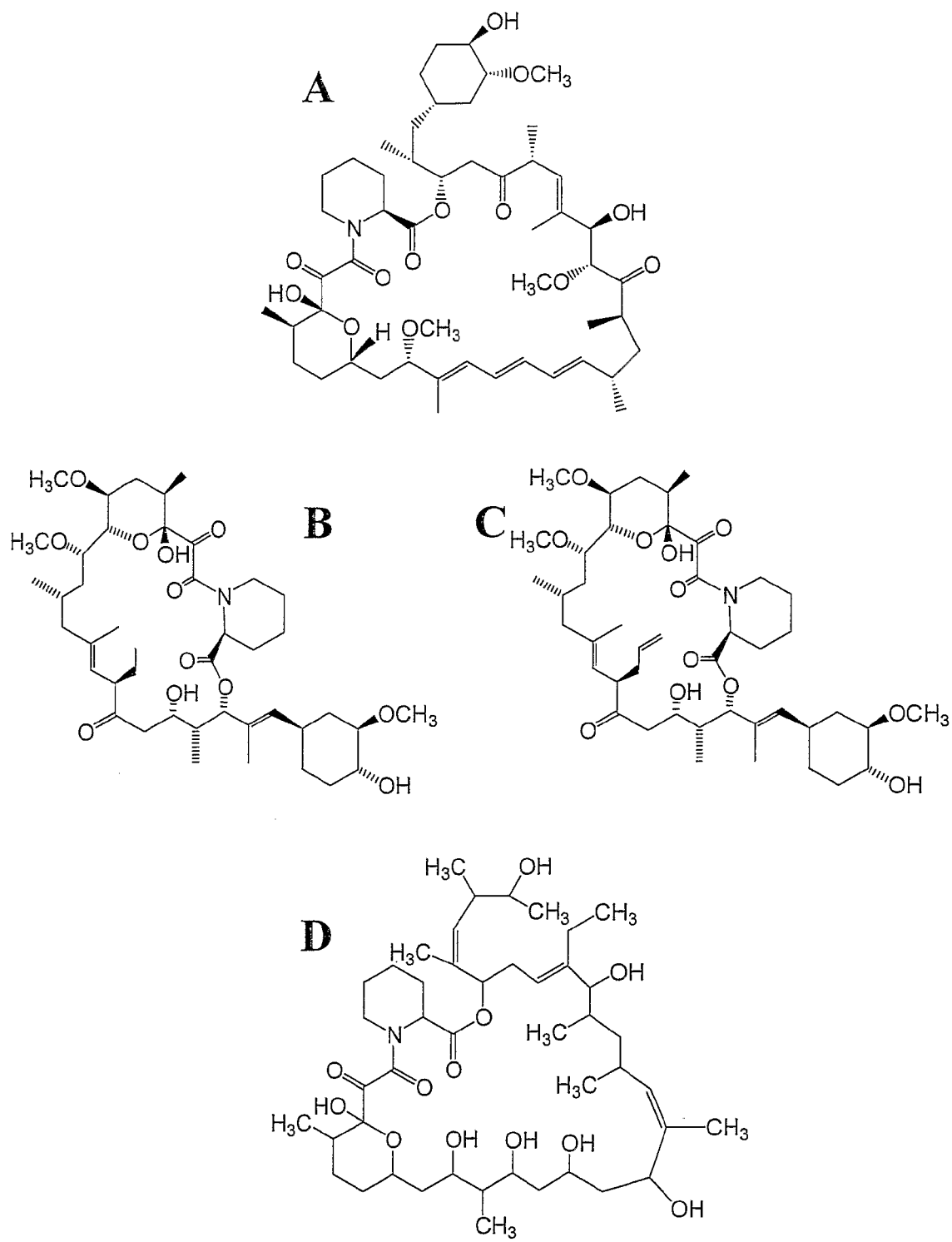
FIG. 2 Structures of rapamycin (A), FK506 (B), FK520 (C) and meridamycin (D).
Figure 3:
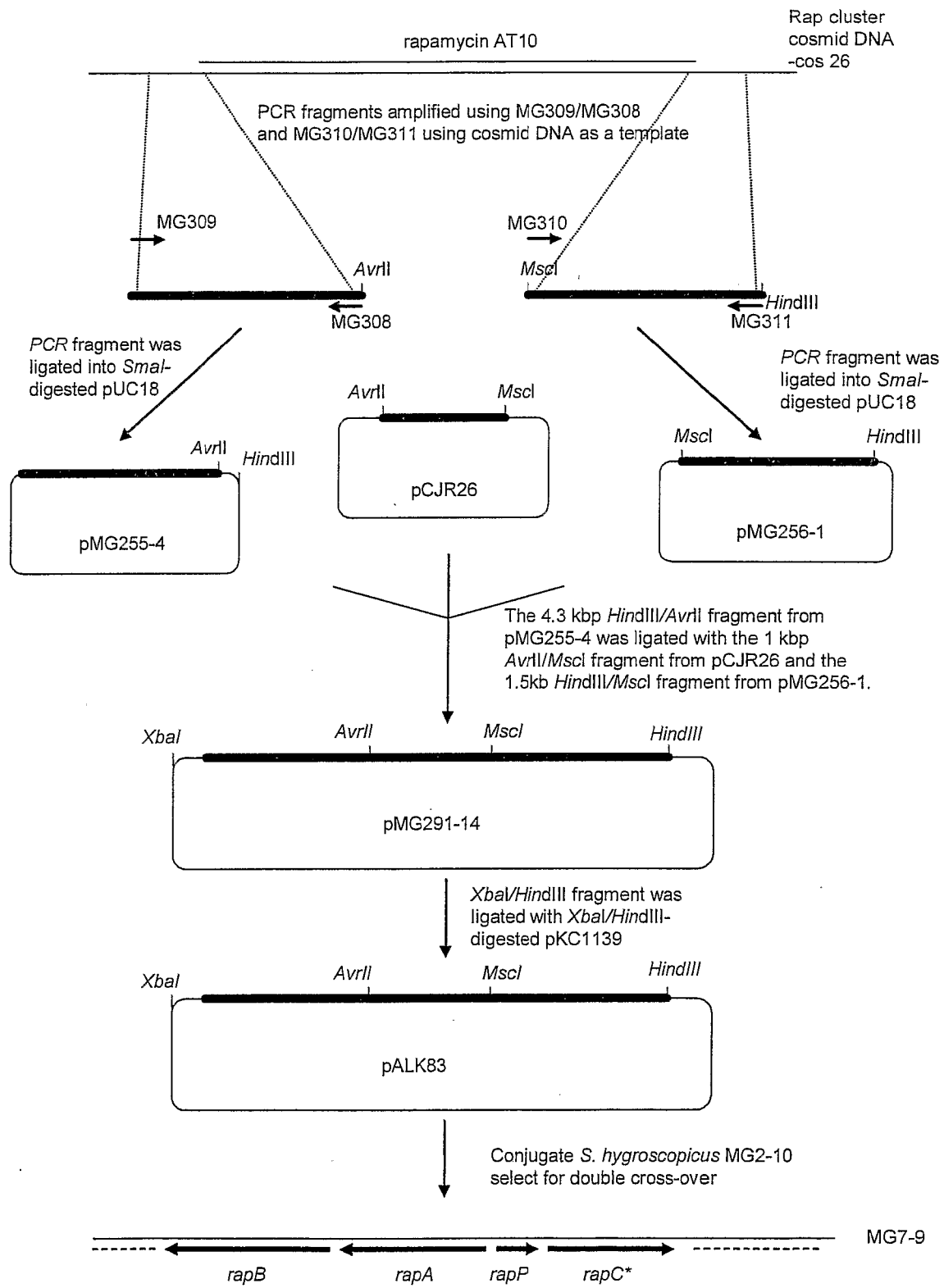
FIG. 3 Genetic engineering of MG2-10 to generate MG7-9.

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group)

As used herein the term "17-desmethylrapamycin and analogues thereof" is intended to include compounds within the scope of formula I below:

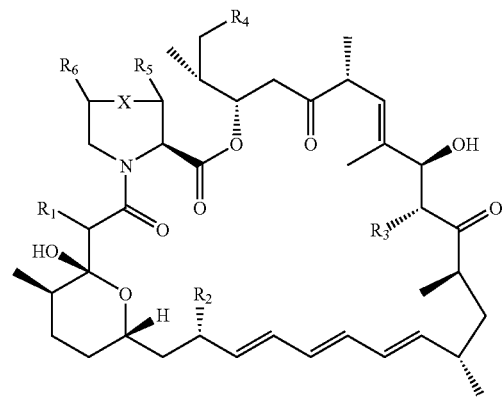

wherein:

x represents a direct bond, —CH$_2$—, —S—CH$_2$—, —CH$_2$—S— or —S(=O)—CH$_2$—;

or —CHR$_5$-x-CHR$_6$— represents

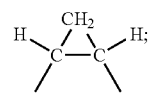

$R_1$ represents =O or (H,H);

$R_2$ represents OH or OMe;

$R_3$ represents H, OH or OMe;

$R_4$ represents a structural fragment selected from groups A, B, C, D, E and F,

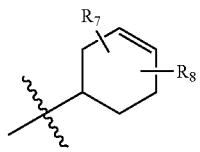
A

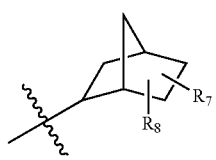
B

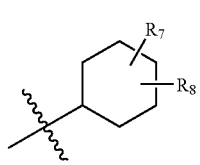
C

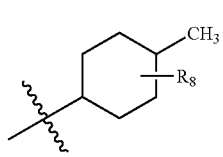
D

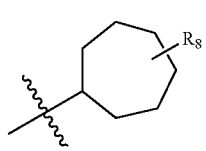
E

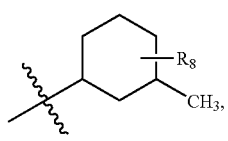
F in which the wavy line indicates the position of attachment of the fragment, $R_7$ represents H, OH or OMe and $R_8$ represents H, OH, OMe, halo, thiol or $C_{1-4}$ alkyl;

or $R_4$ alternatively represents a 5- to 7-membered heterocycle containing one or more heteroatoms selected from the group consisting of O, S and N, which heterocycle is optionally substituted with one or more substituents selected from $C_{1-4}$ alkyl, OH, F and Cl; and $R_5$ and $R_6$ are each independently H or OH, or pharmaceutically acceptable derivatives thereof, which compounds are hereinafter referred to as "compounds of the invention".

As used herein the term "pharmaceutically-acceptable derivatives" includes pharmaceutically-acceptable salts (e.g. acid addition salts). It also includes references to solvates (e.g. hydrates).

As used herein the term "halo" includes fluoro, chloro, bromo and iodo.

As used herein the term "thiol" includes the group SH.

Unless otherwise specified, $C_{1-4}$ alkyl groups mentioned herein may be straight-chained or, when a sufficient number of C-atoms are present (i.e. a minimum of 3) be branched. Such $C_{1-4}$ alkyl groups may additionally be substituted by one or more halo (e.g. fluoro) atoms.

Heterocyclic groups that $R_4$ may represent may be fully saturated, partly unsaturated, wholly aromatic or partly aromatic in character. Such groups may also be monocyclic or, where possible, bicyclic. Values of heterocyclic $R_4$ groups that may be mentioned include dioxanyl, dioxolyl, furanyl, hexahydropyrimidinyl, hydantoinyl, imidazolyl, isoxazolidinyl, isoxazolyl, maleimido, morpholinyl, oxadiazolyl, 1,2- or 1,3-oxazinanyl, oxazolyl, piperazinyl, piperidinyl, pyranyl, pyrazinyl, pyrazolyl, pyridinyl, pyridonyl, pyrimidinyl, pyrrolidinonyl, pyrrolidinyl, pyrrolinyl, pyrrolyl, sulfolanyl, 3-sulfolenyl, tetrahydrofuranyl, tetrahydropyranyl, 3,4,5,6-tetrahydropyridinyl, 1,2,3,4-tetrahydropyrimidinyl, 3,4,5,6-tetrahydropyrimidinyl, tetrazolyl, thiadiazolyl, thiazolidinyl, thiazolyl, thienyl, triazolyl and the like (e.g. saturated or partially unsaturated, monocyclic groups such as dioxanyl, dioxolyl, hexahydropyrimidinyl, hydantoinyl, isoxazolidinyl, maleimido, morpholinyl, piperazinyl, piperidinyl, pyrrolidinonyl, pyrrolidinyl, pyrrolinyl, sulfolanyl, 3-sulfolenyl, tetrahydrofuranyl, tetrahydropyranyl, 3,4,5,6-tetrahydropyridinyl, 1,2,3,4-tetrahydropyrimidinyl, 3,4,5,6-tetrahydropyrimidinyl, thiazolidinyl and the like or, particularly, saturated, monocyclic groups containing one heteroatom selected from N, S or, particularly, O, such as piperidinyl, pyrrolidinyl, tetrahydrofuranyl, tetrahydropyranyl, and the like). However, in a particular embodiment relating to the compounds of the invention, $R_4$ represents a structural fragment selected from groups A, B, C, D, E and F (i.e. it does not represent a heterocyclic group).

As used herein the term "modifying gene(s)" includes the genes required for post-polyketide synthase modifications of the polyketide, for example but without limitation, cytochrome P-450 monooxygenases, ferredoxins and SAM-dependent O-methyltransferases. In the rapamycin system these modifying genes include rapN, rapO, rapM, rapI, rapQ, and rapJ. A person of skill in the art will appreciate that homologues of these genes exist in related biosynthetic gene clusters and the use of these homologous genes in the methods of the invention is also contemplated.

As used herein the term "precursor supply gene(s)" includes the genes required for the supply of the natural or non-natural precursors, the genes required for the synthesis of any naturally or non-naturally incorporated precursors and the genes required for the incorporation of any naturally or non-naturally incorporated precursors. For example but without limitation in the rapamycin system these genes include rapL, rapK, rapP and rapA. A person of skill in the art will appreciate that homologues of these genes exist in related biosynthetic gene clusters and the use of these homologous genes in the methods of the invention is also contemplated.

As used herein, the term "auxiliary gene(s)" includes references to modifying genes, precursor supply genes or both modifying genes and precursor supply genes.

As used herein, the term "precursor" includes the natural starter acid (i.e. 4,5-dihydroxycyclohex-1-enecarboxylic acid), non-natural starter acids, naturally incorporated amino acids (i.e. pipecolic acid, proline), non-naturally incorporated amino acids, malonyl-CoA and methylmalonyl-CoA As used herein the term "non-natural starter acid" refers to any compound which can be incorporated as a starter acid in polyketide synthesis that is not the starter acid usually chosen by that PKS.

For the avoidance of doubt, the terms "precursor" and "non-natural starter acid" include N-acylcysteamine thioesters of oligoketides (e.g. diketides and triketides), and N-acylcysteamine thioesters or esters of carboxylic acids which may be incorporated into the final product.

As used herein the term "natural module" refers to a set of contiguous domains from a KS to an ACP domain, comprising KS-AT-ACP (in that order) and optionally additionally containing one or more domains selected from: a β-ketoreductase (KR) domain, a KR domain and a dehydratase (DH) domain, and a KR domain, a DH domain and a enoyl reductase (ER) domain.

As used herein, the term "combinatorial module" refers to a set of contiguous domains which extends from one point in a natural module to a corresponding point in a subsequent module, for example from the start of an AT domain in module A to the starter of the AT domain in module B, or from the middle of the KS domain in module B to the middle of the KS domain in module C. These combinatorial modules may be "double" or larger, i.e. may contain the same number of domains as two or more natural modules.

As used herein the term "pre-rapamycin" refers to the first enzyme-free product produced by the activity of the rapamycin polyketide synthase (comprising rapA, rapB, and rapC) and rapP before the action of any modifying genes, and in particular to a compound with the structure shown below:

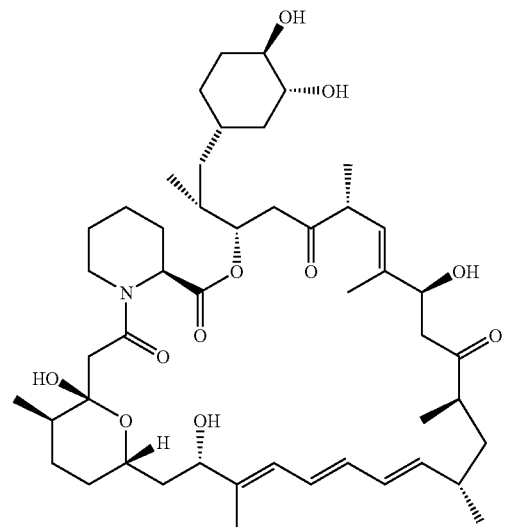

As used herein, the term "autoimmune disorder(s)" includes, without limitation: systemic lupus erythrematosis (SLE), rheumatoid arthritis, myasthenia gravis and multiple sclerosis.

As used herein, the term "diseases of inflammation" includes, without limitation: psoriasis, dermatitis, eczema, seborrhoea, inflammatory bowel disease (including but not limited to ulcerative colitis and Crohn's disease), pulmonary inflammation (including asthma, chronic obstructive pulmonary disease, emphysema, acute respiratory distress syndrome and bronchitis) and eye uveitis.

As used herein, the term "cancer" refers to a malignant new growth that arises from epithelium, found in skin or, more commonly, the lining of body organs, for example, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, gliobastoma, primary liver cancer and ovarian cancer.

As used herein the term "B-cell malignancies" includes a group of disorders that include chronic lymphocytic leukaemia (CLL), multiple myeloma, and non-Hodgkin's lymphoma (NHL). They are neoplastic diseases of the blood and blood forming organs. They cause bone marrow and immune system dysfunction, which renders the host highly susceptible to infection and bleeding.

As used herein, the term "vascular disease" includes, without limitation: hyperproliferative vascular disorders (e.g. restenosis and vascular occlusion), graft vascular atherosclerosis, cardiovascular disease, cerebral vascular disease and peripheral vascular disease (e.g. coronary artery disease, arteriosclerosis, atherosclerosis, nonatheromatous arteriosclerosis or vascular wall damage).

As used herein the terms "neuronal regeneration" refers to the stimulation of neuronal cell growth and includes neurite outgrowth and functional recovery of neuronal cells. Diseases and disorders where neuronal regeneration may be of significant therapeutic benefit include, but are not limited to, Alzheimer's disease, Parkinson's disease, Huntingdon's chorea, amyotrophic lateral sclerosis, trigeminal neuralgia, glossopharyngeal neuralgia, Bell's palsy, muscular dystrophy, stroke, progressive muscular atrophy, progressive bulbar inherited muscular atrophy, cervical spondylosis, Gullain-Barre syndrome, dementia, peripheral neuropathies and peripheral nerve damage, whether caused by physical injury (e.g. spinal cord injury or trauma, sciatic or facial nerve lesion or injury) or a disease state (e.g. diabetes).

As used herein the term "fibrotic diseases" refers to diseases associated with the excess production of the extracellular matrix and includes (without limitation) sarcoidosis, keloids, glomerulonephritis, end stage renal disease, liver fibrosis (including but not limited to cirrhosis, alcohol liver disease and steato-heptatitis), chronic graft nephropathy, vasculopathy, cardiac fibrosis, pulmonary fibrosis (including but not limited to idiopathic pulmonary fibrosis and cryptogenic fibrosing alveolitis), macular degeneration, retinal and vitreal retinopathy and chemotherapy or radiation-induced fibrosis.

As used herein, the term "wound healing" refers to the process of repair that follows injury to the skin and other soft tissues and includes, without limitation, healing of post-surgical wounds, treatment of burns or hypertrophic or keloid scars and the prevention of surgical adhesions.

DESCRIPTION OF THE INVENTION

In one aspect the present invention provides 17-desmethylrapamycin and analogues thereof, in particular the present invention provides 17-desmethylrapamycin analogues according to the following formula:

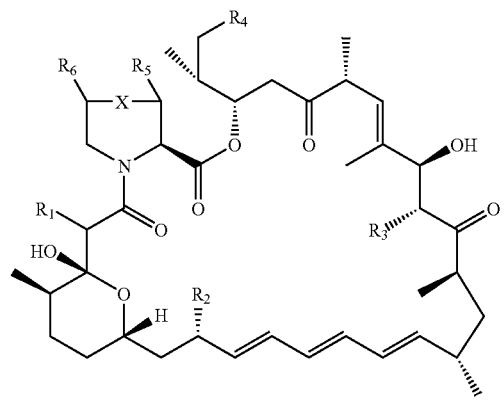

wherein:

x represents a direct bond, —$CH_2$—, —S—$CH_2$—, —$CH_2$—S— or —S(=O)—$CH_2$—;

or —$CHR_5$-x-$CHR_6$— represents

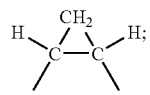

$R_1$ represents =O or (H,H);
$R_2$ represents OH or OMe;
$R_3$ represents H, OH or OMe;
$R_4$ represents a structural fragment selected from groups A, B, C, D, E and F,

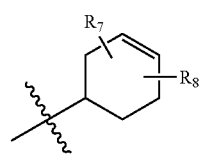

A

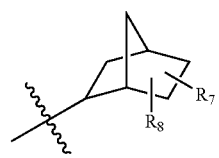

B

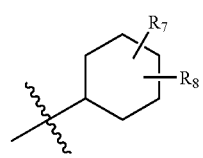

C

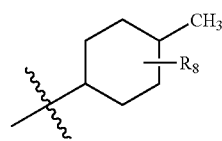

D

-continued

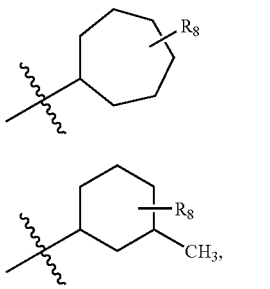

in which
the wavy line indicates the position of attachment of the fragment,
$R_7$ represents H, OH or OMe and
$R_8$ represents H, OH, OMe, halo, thiol or $C_{1-4}$ alkyl;
or $R_4$ alternatively represents a 5- to 7-membered heterocycle containing one or more heteroatoms selected from the group consisting of O, S and N, which heterocycle is optionally substituted with one or more substituents selected from $C_{1-4}$ alkyl, OH, F and Cl; and
$R_5$ and $R_6$ are each independently H or OH,
or pharmaceutically acceptable derivatives thereof.

In one embodiment, $R_4$ represents a structural fragment selected from the groups A, B, C, E and F (e.g. a structural fragment selected from the groups A, C, E and F), as hereinbefore defined, in which $R_7$ and $R_8$ are as hereinbefore defined (e.g. $R_7$ represents H, OH or OMe and $R_8$ represents H, OH, OMe, Cl or F (such as H, OH, OMe or F)).

In a further embodiment $R_4$ represents a structural fragment selected from the groups A(i), C(i), E(i) and F(i):

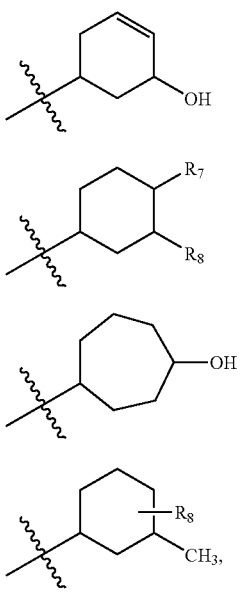

wherein $R_7$ and $R_8$ are as hereinbefore defined (e.g. $R_7$ represents H or OH and $R_8$ represents H, OH or OMe).

In a further preferred embodiment $R_4$ represents the structural fragment C(i), as defined above, in which $R_8$ is H and $R_7$ is H, OMe or, particularly, OH.

In preferred embodiments when $R_5$ represents OH, $R_6$ represents H and when $R_6$ represents OH, $R_5$ represents H; x represents a direct bond or, particularly, $CH_2$.

In an alternative embodiment $R_2$ represents OH.

In an alternative embodiment $R_4$ represents a 6-membered ring with an oxygen at the 4 position (i.e. tetrahydropyran-4-yl).

A preferred embodiment of the compounds of the invention is that in which:
$R_1$ represents (H, H) or =O;
$R_2$ represents OH or OMe;
$R_3$ represents OH or OMe;
$R_4$ represents the structural fragment C(i), as defined above, in which $R_7$ represents OH and $R_8$ represents H, OH or OMe; and
x represents $CH_2$.

In a more highly preferred embodiment:
$R_1$ represents (H, H);
$R_2$ represents OH;
$R_3$ represents H;
$R_4$ represents structural fragment C(i), as defined above, in which $R_7$ represents OH and $R_8$ represents H; and
x represents $CH_2$.

In a preferred embodiment:
$R_1$ represents (H, H);
$R_2$ represents OH;
$R_3$ represents H;
$R_4$ represents the structural fragment C(i), as defined above, in which $R_7$ and $R_8$ both represent OH; and
x represents $CH_2$.

In a more highly preferred embodiment:
$R_1$ represents (H, H);
$R_2$ represents OH;
$R_3$ represents H;
$R_4$ represents the structural fragment C(i), as defined above, in which $R_7$ represents OH and $R_8$ represents F; and
x represents $CH_2$.

In a more highly preferred embodiment:
$R_1$ represents =O;
$R_2$ represents OH or OMe;
$R_3$ represents H, OH or OMe;
$R_4$ represents the structural fragment C(i), as defined above, in which $R_7$ represents OH and $R_8$ represents F or Cl; and
x represents $CH_2$.

In a more highly preferred embodiment:
$R_1$ represents =O;
$R_2$ represents OH;
$R_3$ represents OMe;
$R_4$ represents the structural fragment C(i), as defined above, in which $R_7$ represents OH and $R_8$ represents H; and
x represents $CH_2$.

In a more highly preferred embodiment:
$R_1$ represents =O;
$R_2$ represents OH;
$R_3$ represents OH;
$R_4$ represents the structural fragment C(i), as defined above, in which $R_7$ represents OH and $R_8$ represents H; and
x represents $CH_2$.

In a more highly preferred embodiment:
$R_1$ represents =O;
$R_2$ represents OH;
$R_3$ represents OMe;
$R_4$ represents the structural fragment C(i), as defined above, in which $R_7$ represents OH and $R_8$ represents OMe; and x represents $CH_2$.

In one embodiment the compound is not 17-desmethylrapamycin.

In relation to all of the above-mentioned embodiments of the compounds of the invention in which the group $R_4$ represents a substituted cyclohexane ring, further embodiments that may be mentioned include those in which the relative stereochemistry of the substituents on the cyclohexane ring is such that each of the substituents (including the polyketide ring to which the group $R_4$ is attached) can simultaneously adopt an equatorial position when the cyclohexane ring is in a chair conformation. Thus, for example compounds of the invention that may be mentioned include those in which groups attached at the 2-, 4- and/or or 6-positions of the cyclohexane rings of structural fragments C, D, F, C(i) and F(i) are trans-relative to the polyketide ring attached at the 1-position of the cyclohexane group. Further, other compounds of the invention that may be mentioned include those in which groups attached at the 3- and/or 5-positions of the cyclohexane rings of structural fragments C, D, F, C(i) and F(i) are cis-relative to the polyketide ring attached at the 1-position of the cyclohexane group. Thus, yet further compounds of the invention that may be mentioned include those in which, when the group $R_4$ represents the structural fragment C(i), then, relative to the polyketide ring attached at position 1 of the cyclohexane ring, the group $R_7$ (if present, and particularly if an OH or OMe group) has trans-stereochemistry and the group $R_8$ (if present, and particularly if an OH or OMe group) has cis-stereochemistry. Similarly, when the group $R_4$ represents a cyclohex-3-ene ring (i.e. the structural fragment A or A(i)), then compounds of the invention that may be mentioned include those in which, relative to the polyketide ring attached at position 1 of the cyclohexene ring, substituents at 2- and/or 6-positions have trans-stereochemistry and substituents at the 3-position have cis-stereochemistry.

A person of skill in the art will appreciate that the methods described herein for the generation of 17-desmethylrapamycin and analogues thereof are applicable to the generation of libraries of related analogues. Therefore, in a further aspect the present invention provides libraries of 17-desmethylrapamycin analogues generated using the methods of the present invention. In particular, the present invention provides libraries of 17-desmethylrapamycin analogues differing in one or more of: the starter acid incorporated, the amino acid incorporated, the degree of post-PKS processing and semi-synthetic derivatisation.

The novel rapamycin analogues are useful directly, and as templates for further semi-synthesis or bioconversion, to produce compounds useful as immunosuppressants, antifungal agents, anticancer agents, anti-inflammatory agents, neuroregenerative agents or agents for the treatment of transplantation rejection, graft vs. host disease, autoimmune disorders, vascular disease and fibrotic diseases or agents for use in the regulation of wound healing. Methods for the semisynthetic derivatisation of rapamycin and analogues thereof are well known in the art and include (but are not limited to) those modifications described in e.g. U.S. Pat. Nos. 5,665,772; 5,362,718, WO 96/41807; U.S. Pat. Nos. 5,728,710, 5,378, 836; 5,138,051; 5,665,772; 5,391,730; 5,023,262, 5,563,145, 5,446,048, 5,912,253, 5,221,670; 5,955,457; WO 98/04279, U.S. Pat. Nos. 6,015,815 and 5,432,183)

In a further aspect, the present invention provides the use of 17-desmethylrapamycin or analogues thereof in medicine. In a further aspect the present invention provides for the use of 17-desmethylrapamycin or an analogue thereof in the preparation of a medicament for the induction or maintenance of immunosuppression, the stimulation of neuronal regeneration or the treatment of cancer, B-cell malignancies, fungal infections, transplantation rejection, graft vs. host disease, autoimmune disorders, diseases of inflammation vascular disease and fibrotic diseases or agents for use in the regulation of wound healing.

Rapamycin analogues are also known to have utility in the treatment of other conditions, including, but not limited to lymphangioleiomyomatosis and tuberous sclerosis. The uses and methods involving the compounds of the invention also extend to these other indications.

One skilled in the art would be able by routine experimentation to determine the ability of these compounds to inhibit fungal growth (e.g. Baker, H., et al., 1978; NCCLS Reference method for broth dilution antifungal susceptibility testing for yeasts: Approved standard M27-A, 17 (9). 1997). Additionally, one skilled in the art would be able by routine experimentation to determine the ability of these compounds to inhibit tumour cell growth, (see Dudkin, L., et al., 2001; Yu et al. 2001). In a further aspect the compounds of this invention are useful for inducing immunosuppression, assays for determining a compound's efficacy in these areas are well known to those of skill in the art, for example but without limitation: Immunosuppressant activity—Warner, L. M., et al., 1992, Kahan et al. (1991) & Kahan & Camardo, 2001); Allografts—Fishbein, T. M., et al., 2002, Kirchner et al. 2000; Autoimmune/Inflammatory/Asthma—Carlson, R. P. et al., 1993, Powell, N. et al., 2001; Diabetes I—Rabinovitch, A. et al., 2002; Psoriasis—Reitamo, S. et al., 2001; Rheumatoid arthritis—Foey, A., et al., 2002; Fibrosis—Zhu, J. et al., 1999, Jain, S., et al., 2001, Gregory et al. 1993.

The ability of the compounds of this invention to induce immunosuppression may be demonstrated in standard tests used for this purpose. In a further aspect the compounds of this invention are useful in relation to antifibrotic, neuroregenerative and anti-angiogenic mechanisms, one skilled in the art would be able by routine experimentation to determine the ability of these compounds to prevent angiogenesis (e.g. Guba, M., et al., 2002). One of skill in the art would be able by routine experimentation to determine the utility of these compounds to treat vascular hyperproliferative disease, for example in stents (e.g. Morice, M. C., et al., 2002). Additionally, one of skill in the art would be able by routine experimentation to determine the neuroregenerative ability of these compounds (e.g. Myckatyn, T. M., et al., 2002, Steiner et al., 1997).

The present invention also provides a pharmaceutical composition comprising 17-desmethylrapamycin or an analogue thereof, or a pharmaceutically acceptable salt thereof, together with a pharmaceutically acceptable carrier.

The aforementioned compounds of the invention or a formulation thereof may be administered by any conventional method for example but without limitation they may be administered parenterally, orally, topically (including buccal, sublingual or transdermal), via a medical device (e.g. a stent), by inhalation or via injection (subcutaneous or intramuscular). The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The compounds of the invention may be administered alone or in combination with other therapeutic agents, co-administration of two (or more) agents allows for significantly lower doses of each to be used, thereby reducing the side effects seen.

In one embodiment, 17-desmethylrapamycin or an analogue thereof is co-administered with another therapeutic agent for the induction or maintenance of immunosuppression, for the treatment of transplantation rejection, graft vs. host disease, autoimmune disorders or diseases of inflammation preferred agents include, but are not limited to, immunoregulatory agents e.g. azathioprine, corticosteroids, cyclophosphamide, cyclosporin A, FK506, Mycophenolate Mofetil, OKT-3 and ATG.

In a alternative embodiment, 17-desmethylrapamycin or an analogue thereof is co-administered with another therapeutic agent for the treatment of cancer or B-cell malignancies preferred agents include, but are not limited to, methotrexate, leukovorin, adriamycin, prenisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® or hsp90 inhibitors (e.g. 17-AAG). Additionally, 17-desmethyl rapamycin or an analogue thereof may be administered in combination with other therapies including, but not limited to, radiotherapy or surgery.

In one embodiment, 17-desmethylrapamycin or an analogue thereof is co-administered with another therapeutic agent for the treatment of vascular disease, preferred agents include, but are not limited to, ACE inhibitors, angiotensin II receptor antagonists, fibric acid derivatives, HMG-CoA reductase inhibitors, beta adrenergic blocking agents, calcium channel blockers, antioxidants, anticoagulants and platelet inhibitors (e.g. Plavix™)

In one embodiment, 17-desmethylrapamycin or an analogue thereof is co-administered with another therapeutic agent for the stimulation of neuronal regeneration, preferred agents include, but are not limited to, neurotrophic factors e.g. nerve growth factor, glial derived growth factor, brain derived growth factor, ciliary neurotrophic factor and neurotrophin-3.

In one embodiment, 17-desmethylrapamycin or an analogue thereof is co-administered with another therapeutic agent for the treatment of fungal infections; preferred agents include, but are not limited to, amphotericin B, flucytosine, echinocandins (e.g. caspofungin, anidulafungin or micafungin), griseofulvin, an imidazole or a triazole antifungal agent (e.g. clotrimazole, miconazole, ketoconazole, econazole, butoconazole, oxiconazole, terconazole, itraconazole, fluconazole or voriconazole).

By co-administration is included any means of delivering two or more therapeutic agents to the patient as part of the same treatment regime, as will be apparent to the skilled person. Whilst the two or more agents may be administered simultaneously in a single formulation this is not essential. The agents may be administered in different formulations and at different times.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compounds of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Solutions or suspensions of compounds of the invention suitable for oral administration may also contain excipients e.g. N,N-dimethylacetamide, dispersants e.g. polysorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate), Tablets may contain excipients such as microcrystalline cellulose, lactose (e.g. lactose monohydrate or lactose anhydrous), sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxy-propylcellulose (HPC), macrogol 8000, sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

The compounds of the invention may also be administered using medical devices known in the art. For example, in one embodiment, a pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. In a specific embodiment the compounds of the invention may be administered using a drug-eluting stent, for example corresponding to those described in WO 01/87263 and related publications or those described by Perin (Perin, E C, 2005). Many other such implants, delivery systems, and modules are known to those skilled in the art.

In an alternative embodiment of the present aspect the compounds of the invention may be presented to the patient in the form of "prodrugs", this is particularly applicable in the case of an anticancer agent but may also be used for other indications.

The term "prodrug" as used in this application refers to a precursor or derivative form of a pharmaceutically active substance that is less cytotoxic compared to the parent drug and is capable of being enzymatically activated or converted into the more active parent form (see, for example, Wilman D. E. V., 1986 and Stella V. J. et al., 1985).

The dosage to be administered of a compound of the invention will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, preferably from 10-60%, or more, by weight, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

In an alternative aspect the present invention provides a method for the production of 17-desmethylrapamycin or an analogue thereof said method comprising (a) replacing the methylmalonyl-CoA specific AT domain of module 10 of the rapamycin PKS with a malonyl-CoA-specific AT domain, (b) expressing the engineered rapamycin PKS in a suitable host cell (c) culturing the host cell under conditions such that 17-desmethylrapamycin or an analogue thereof is produced including optionally supplying exogenous precursors (d) optionally isolating the compound thus produced.

In a specific embodiment, the compound produced is not 17-desmethylrapamycin.

This replacement results in the incorporation of malonyl-CoA by rapamycin PKS module 10 and the absence of a methyl branch at C17 compared to rapamycin or pre-rapamycin. In a preferred embodiment, the malonyl-CoA specific AT domain is selected from one of the following polyketide synthase gene clusters: rapamycin, monensin, FK506, erythromycin, FK520, amphotericin, angolamycin, tylosin, 'hyg', FK523, meridamycin, antascomicin, FK525 and tsukubamycin. In a more preferred embodiment the malonyl-CoA specific AT domain is selected from one of the following clusters: rapamycin, monensin or FK506. In a more highly preferred embodiment the malonyl-CoA specific AT domain is selected from the group consisting of the AT domain from rapamycin module 2, the AT domain from monensin module 3, the AT domain from monensin module 6, the AT domain from monensin module 8, the AT domain from FK506 module 3 and the AT domain from FK506 module 7. In the most highly preferred embodiment the malonyl-CoA specific AT domain is the AT domain from module 2 of rapamycin.

It should be noted that a number of errors in the deposited sequence have been identified such as those reported in WO 04/007709. The present authors predict that there may be further errors in the deposited sequence some of which may be in the regions used in this work to engineer the cluster. The sequences in the sequence listing represent sequences of synthesised oligonucleotides which were designed on the basis of the published sequence and DNA fragments amplified by polynucleotide chain reaction (PCR) which have been sequenced. They may therefore not be identical to the deposited sequence. One skilled in the art will appreciate that cloned DNA fragments that have not been sequenced will have the biologically correct sequence to form functional proteins and errors in the deposited sequence have no effect on this. Also identified (NCBI accession number X86780) are the predicted translation products of the PKS genes, and (Aparicio et al., 1996) the boundaries of the domains and modules. One skilled in the art will appreciate that there is an amount of fluidity in the definition of a domain and the boundaries as defined in Schwecke et al., (1995) should be considered to be examples of where boundaries may be.

One skilled in the art will appreciate that there are many malonyl-CoA specific AT domains in type I polyketide synthases (and mixed PKS-NRPS) that could be used as donor AT domains and that this transformation could be attempted with any of a number of malonyl-CoA selective acyl transferase domains from any type I PKS or mixed NRPS/PKS. One skilled in the art will also appreciate that incorporation of malonyl-CoA by the module 10 AT could be effected by mutating the rapAT10 to alter its specificity, for example using the methods as described in WO 02/14482, or by replacing module 10 with a module that contains an AT domain which is selective for malonyl-CoA, said module including a natural module or a combinatorial module.

The introduction of the malonyl-CoA specific AT into module 10 of the rapamycin PKS is achieved by the introduction of restriction sites flanking the donor domain and cloning this in-frame and in the same position as the acyltransferase of rapamycin module 10. One skilled in the art will appreciate that this can be achieved by use of a range of restriction enzyme sites and a range of junction positions. In a preferred embodiment the malonyl-CoA specific AT domain of rapamycin AT2 is introduced on a DNA fragment flanked by the restriction enzyme sites MscI and AvrII. The MscI site is introduced at the beginning of the AT domain overlapping with the DNA sequence encoding the conserved amino acid sequence PGQ, see below. The AvrII site is introduced at the end of the AT domain overlapping with the DNA sequence encoding the conserved amino acid sequence VLG, see below. One skilled in the art will appreciate that within this cloning strategy the MscI site is methylated and passaging through an *E. coli* strain such as ET12567 to generate dcm$^{-1}$ DNA is required prior to digestion with the restriction enzyme MscI. Alternative embodiments involve the use of different restriction sites, for example but without limitation SpeI and AvrII, MscI and BglII, SpeI and BglII. An alternative preferred restriction site combination is SpeI and AvrII.

```
Generation of an MscI site at the start of the AT
domain:
Rap AT10        F    P    G    Q    G    (SEQ ID NO: 1)
                ttt  ccc  ggg  cag  gga  (SEQ ID NO: 2)

Rap AT2         F    P    G    Q    G    (SEQ ID NO: 3)
                ttc  ccg  ggt  cag  ggg  (SEQ ID NO: 4)

MscI junction   F    P    G    Q    G    (SEQ ID NO: 5)
                ttt  cct  ggc  cag  ggg  (SEQ ID NO: 6)

Generation of an AvrII site at the end of the AT
domain
Rap AT10        A    V    L    G    D    (SEQ ID NO: 7)
                gcg  gtg  ctg  ggt  gat  (SEQ ID NO: 8)

Rap AT2         A    V    L    G    D    (SEQ ID NO: 9)
                gcg  gtg  ctg  ggt  gat  (SEQ ID NO: 10)

AvrII           A    V    L    G    D    (SEQ ID NO: 11)
junction        gcg  gtc  cta  ggt  gat  (SEQ ID NO: 12)
```

In a preferred embodiment the rapamycin polyketide synthase of *S. hygroscopicus* MG2-10 is engineered to have a malonyl-CoA specific AT in module 10. In a highly preferred embodiment the malonyl-CoA AT is rapamycin AT2, as described in example 1 herein.

One skilled in the art will appreciate that there are a number of ways in which DNA may be introduced into a cell in order to effect the engineering of a PKS gene cluster. In example 1 we describe a conjugative method using a temperature sensitive origin plasmid. One skilled in the art will appreciate that other methods may also be used, for example but without limitation, homologous recombination without using a self-replicating vector, the methods as described in WO 03/033699. Therefore the recombinant methods of generating an engineered rapamycin PKS should not be limited to those described herein.

However, the methods described herein are the preferred methods for generating an engineered PKS cluster. To date no success for the engineering of rapA, rapB or rapC has been reported with the alternative methods described above.

In a further aspect the present invention provides a method for generating a recombinant strain that contains an engineered biosynthetic cluster that encodes a rapamycin polyketide synthase where the methylmalonyl-CoA specific AT domain of module 10 has been replaced with a malonyl-CoA specific AT domain, as described above. In a preferred embodiment, the malonyl-CoA specific AT domain is selected from one of the following polyketide synthase gene clusters: rapamycin, monensin, FK506, erythromycin, FK520, amphotericin, angolamycin, tylosin, 'hyg', FK523, meridamycin, antascomicin, FK525 and tsukubamycin. In a more preferred embodiment the malonyl-CoA specific AT domain is selected from one of the following clusters: rapamycin, monensin or FK506. In a more highly preferred embodiment the malonyl-CoA specific AT domain is selected from the group consisting of rapamycin module 2, monensin module 3, monensin module 6, monensin module 8, FK506 module 3 and FK506 module 7. In the most highly preferred embodiment the malonyl-CoA specific AT domain is from module 2 of rapamycin.

Although engineering of the rapamycin polyketide synthase pathway has been exemplified herein in *S hygroscopicus* MG2-10 (the production of which is disclosed in WO 04/007709 and in Gregory et al., (2004)) a person of skill in the art will appreciate that these methods can equally be applied to wild-type *S. hygroscopicus* NRRL5491 and other related strains (see below). Preferably, the engineered strain is selected from the group consisting of *S. hygroscopicus* MG2-10 and *S. hygroscopicus* NRRL5491.

In this context, strains related to *S. hygroscopicus* NRRL5491 include: *Actinoplanes* sp. N902-109 (e.g. FERM BP-3832), *Streptomyces* sp. AA6554, *Streptomyces hygroscopicus* var. *ascomyceticus* MA 6475 (e.g. ATCC 14891), *Streptomyces hygroscopicus* var. *ascomyceticus* MA 6678 (e.g. ATCC 55087), *Streptomyces hygroscopicus* var. *ascomyceticus* MA 6674, *Streptomyces hygroscopicus* var. *ascomyceticus* (e.g. ATCC 55276), *Streptomyces tsukubaensis* No. 9993 (e.g. FERM BP-927), *Streptomyces hygroscopicus* subsp. *yakushimaensis*, *Streptomyces* sp. (e.g. DSM 4137), *Streptomyces* sp. (e.g. DSM 7348), *Micromonospora* n.sp. A92-306401 (e.g. DSM 8429) and *Streptomyces* sp. MA 6858 (e.g. ATCC 55098). In one embodiment the strain is not a recombinant *S. hygroscopicus* host cell that produces 17-desmethylrapamycin. In a further embodiment the strain is not a recombinant *S. hygroscopicus* host cell that produces 17-desmethylrapamycin in the absence of the provision of exogenous precursors. In a further embodiment the strain is not a recombinant *S. hygroscopicus* host cell containing a deletion of the five contiguous genes, rapQONML.

Optionally, this method can be combined with the methods disclosed in WO 04/007709 to allow the production of 17-desmethylrapamycin analogues which differ from the natural rapamycin structure in the degree of processing by the post-PKS enzymes or in the incorporation of non-natural starter acids.

An embodiment of the previous aspects of the invention providing a method for the production of 17-desmethylrapamycin and analogues thereof and a method of generating a recombinant strain that contains a biosynthetic cluster that encodes an engineered rapamycin polyketide synthase, comprises the additional steps of:
(a) isolating the AT to be introduced as a single DNA fragment with suitable flanking restriction sites,
(b) amplifying and isolating the regions of DNA sequence homologous to the flanking sequences of the target AT using the same appropriate restriction sites,
(c) ligating the three DNA fragments as described in (a) and (b) together to give an in-frame sequence of LHS homology followed by donor AT domain followed by RHS homology,
(d) introducing the complete sequence from (c) into a vector for introduction into the host strain to give the final plasmid, said plasmid comprising:
  i) the oriT for conjugation,
  ii) one or more resistance markers,
  iii) a temperature sensitive origin of replication such that integrants can be selected by culturing at 37° C., and
  iv) an *E. coli* origin of replication (e) transforming the host strain by conjugation using the final plasmid as described in (d) above,
(f) selecting the transformants by resistance to the relevant antibiotic,
(g) generating the primary integrants by culturing at 37° C. with antibiotic selection,
(h) screening the secondary recombinants by growth in the absence of antibiotic selection, also at 37° C.,
(i) identifying the desired strain by its ability to produce the target product and
(j) optionally confirming the genetics of the strain by standard methods.

One skilled in the are will appreciate that appropriate restriction sites as referred to in step (b) must be such that the three sequences are in-frame when ligated together—they are not necessarily the same as the two sites used for the AT; specifically the restriction site on the RHS of the left-hand region of homology must be the same as, or compatible with to give an in-frame sequence, the site on the LHS of the AT; the restriction site on the LHS of the left-hand region of homology can be any site appropriate to carry out the subsequent cloning steps. Similarly, the site on the LHS of the right-hand region of homology must be the same as, or compatible with to give an in-frame sequence, the site on the RHS of the AT; the restriction site on the RHS of the right-hand region of homology can be any site appropriate to carry out the subsequent cloning steps.

In a further aspect the present invention provides a method for making a 17-desmethylrapamycin analogue, said method comprising:
(a) generating a recombinant strain in which the methylmalonyl-CoA specific AT domain of module 10 of the rapamycin PKS has been replaced with a malonyl-CoA specific AT domain,
(b) feeding non-natural starter acids to a culture of said recombinant strain under conditions suitable for polyketide production, and
(c) optionally isolating the compound thus produced.

Therefore, the present invention provides a method for generating 17-desmethylrapamycin analogues which have incorporated non-natural starter acids. In particular the present invention provides for the incorporation of cyclic and heterocyclic starter acids into 17-desmethylrapamycin analogues, said method comprising feeding said alternative starter acids to a strain which contains the engineered rapamycin biosynthetic gene cluster which is responsible for the synthesis of the 17-desmethylpre-rapamycin core. In one embodiment the recombinant strain has had a precursor supply gene deleted or inactivated. In a preferred embodiment the precursor supply gene which has been deleted or inactivated is rapK. In a further preferred embodiment the recombinant strain has had rapK deleted or inactivated and the non-natural starter acid fed to this strain is selected from the group consisting of cyclohexanecarboxylic acid, 3-methylcyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In one embodiment the strain is not a recombinant *S. hygroscopicus* host cell that produces 17-desmethylrapamycin. In a further embodiment, the strain is not a recombinant *S. hygroscopicus* host cell that produces 17-desmethylrapamycin in the absence of the provision of exogenous precursors.

This aspect of the invention provides methods for the efficient production of a multiplicity of basic products through the incorporation of non-natural precursors (e.g. cyclic or heterocyclic starter acids). Methods may also embody further aspects as set out below.

Therefore in one aspect the present invention provides a method of generating 17-desmethylrapamycin analogues which incorporate a cyclic or heterocyclic starter acid, said method comprising:
(a) modifying said recombinant strain that contains the engineered rapamycin PKS genes to additionally delete or inactivate at least one precursor supply gene; and
(b) feeding a cyclic or heterocyclic non-natural starter acid to said recombinant strain In a preferred embodiment the recombinant strain is generated using the methods described in WO 04/007709 and herein. In a preferred embodiment, one of the precursor supply genes which has been deleted or inactivated is rapK.

In one embodiment, the exogenous acids fed include (without limitation) cycloalkyl carboxylic acids, or simple esters thereof, with ring sizes varying from 5 to 7 atoms. In a preferred embodiment the carboxylic acids are those described in WO 04/007709.

In another preferred embodiment the non-natural starter acids are those described in example 2 herein. In a more preferred embodiment non-natural starter acids fed to this strain is selected from the group consisting of cyclohexanecarboxylic acid, 3-methylcyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid.

In one embodiment, the heterocyclic starter acids that may be fed may include (without limitation): heterocyclic carboxylic acids, or simple esters thereof, with ring sizes varying from 5 to 7 atoms, said rings may contain one or more heteroatoms, where the ring contains more than one heteroatom said heteroatoms may be the same or they may be different. The heteroatom may be selected from the group consisting of O, S and N. Where the ring contains an N it may be as the free base (NH), as the acylated amine (N-acyl), as the alkylated amine (N-alkyl) or as the alkylated N-oxide (N-alkyl, N—O). Where the ring contains an S it may be as a cyclic thioether, sulfoxide or sulfone. In all of the above heterocyclic carboxylic acids the remainder of the ring may be unsubstituted or optionally it may contain one or more substituents, including but not limited to a $C_{1-4}$ alkyl, OH, F and Cl. Preferably, in one embodiment the heterocyclic carboxylic acid contains a 6 membered ring, with an oxygen atom in the 4 position. In a further preferred embodiment, the heterocyclic carboxylic acid is tetrahydro-2H-pyran-4-carboxylic acid In a further aspect, the present invention provides a method for generating a 17-desmethylrapamycin analogue, said method comprising:
(a) generating a recombinant strain in which the methylmalonyl-CoA specific AT domain of module 10 of the rapamycin PKS has been replaced with a malonyl-CoA specific AT domain (as described in more detail above),
(b) additionally deleting or inactivating one or more rapamycin auxiliary genes selected from rapI, rapJ, rapK, rapL, rapM, rapN, rapO and rapQ,
(c) culturing the strain thus obtained, optionally in the presence of an exogenous precursor if required, to produce the 17-desmethylrapamycin analogue, and
(d) optionally isolating the compound thus produced.

In a preferred embodiment the auxiliary genes which have been deleted or inactivated are rapI, rapJ and rapQ. In an alternative preferred embodiment the auxiliary genes that have been deleted are rapJ, rapM and rapQ.

In an alternative aspect of the present invention, the altered rapamycin PKS is expressed in a host cell in which one or more of the rapamycin auxiliary genes has been deleted or inactivated. In an alternative embodiment the altered rapamycin PKS is expressed in a host cell in which all of the auxiliary genes have been deleted or inactivated for example, but not limited to, the host strain *S. hygroscopicus* MG2-10 (WO 04/007709; Gregory et al., 2004). A person of skill in the art will appreciate, based on the disclosure present in WO 04/007709, that if rapK has been deleted or inactivated, an exogenous acid will need to be supplied for the production of 17-desmethylrapamycin or an analogue thereof.

In a further aspect, the present invention provides a method for generating a 17-desmethylrapamycin analogue, said method comprising:
(a) generating a recombinant strain in which the methylmalonyl-CoA specific AT domain of module 10 of the rapamycin PKS has been replaced with a malonyl-CoA specific AT domain (as described in more detail above),
(b) additionally deleting or inactivating one or more rapamycin auxiliary genes selected from rapI, rapJ, rapK, rapL, rapM, rapN, rapO and rapQ,
(c) re-introducing all or a subset of auxiliary genes in-trans to complement or partially complement the deletion,
(d) culturing the strain thus obtained, optionally in the presence of an exogenous precursor if required, to produce the 17-desmethylrapamycin analogue, and
(e) optionally isolating the compound thus produced.

In a preferred embodiment, in step (b) all the rapamycin auxiliary genes are deleted or inactivated. In a further preferred embodiment the recombinant strain is genetically complemented with one or more auxiliary genes selected from the group consisting of rapI, rapJ, rapK, rapL, rapM, rapN, rapO and rapQ or homologues thereof. In a specific embodiment the strain is complemented with all the auxiliary genes. In a further preferred embodiment the recombinant strain is genetically complemented with the rapamycin auxiliary genes rapK, rapM, rapN, rapO and rapL or homologues thereof. In an alternative preferred embodiment the recombinant strain is genetically complemented with the rapamycin auxiliary genes rapK, rapI, rapN, rapO and rapL or homologues thereof.

Therefore, in a specific aspect of the present invention the AT swap is carried out in *S. hygroscopicus* MG2-10 (which is disclosed in WO 04/007709 and Gregory et al., (2004)) where all of the auxiliary genes have been removed, to generate a strain which requires chemical complementation with an exogenous acid to produce a rapamycin product. For example feeding cyclohexanecarboxylic acid leads to the production of 17-desmethyl-39-deshydroxypre-rapamycin and feeding the starter acid 3,4-dihydroxycyclohexanecarboxylic acid leads to the production of 17-desmethylpre-rapamycin. In a preferred embodiment the strain generated by carrying out an AT swap in *S. hygroscopicus* MG2-10 is *S. hygroscopicus* MG7-9 which is generated, as described in example 1, by introducing the acyl transferase of rapamycin module 2 into module 10 to replace the native AT10.

One skilled in the art will appreciate that in *S. hygroscopicus* MG7-9 there is not a copy of rapL and that the chemical complementation described does not refer to addition of pipecolic acid or an alternative amino acid. It is the case that supplementing the complex production media with lysine serves to provide the strain with pipecolic acid (via a process not determined, but established by observation of the produced pre-rapamycin analogues). Culturing of this strain (*S. hygroscopicus* MG7-9) leads to co-production of 17-desmethylprolylrapamycin analogues being observed at low levels and similar observations are made for other strains that are deficient in RapL. Exogenous natural and novel amino acids can be incorporated into the wild-type rapamycin molecule by feeding into the production media in direct competition with pipecolic acid. One skilled in the art will appreciate that similarly, natural or non-natural amino acids could be fed to rapL deleted strains such as, but not limited to, *S. hygroscopicus* MG7-9 in order to provide further novel rapamycin analogues.

Optionally, one or more of the deleted auxiliary genes may be introduced into said host cell under an appropriate promoter. In a preferred embodiment one or more of the deleted genes may be introduced into the chromosomal phage attachment site of the *Streptomyces* phage phiBT1 (Gregory et al., 2003). One skilled in the art will appreciate that complementation in-trans is not limited to this phage attachment site, or indeed to the use of an attachment site. Therefore, complementation of deleted auxiliary genes can also be effected by, but not limited to, introduction of one or more auxiliary genes under an appropriate promoter into other phage attachment sites such as the attachment site for *Streptomyces* phage phiC31 for example by using a derivative of pSET152 (Bierman et al., 1992). Such integration may similarly be performed using other available integration functions including but not limited to: vectors based on pSAM2 integrase (e.g. in pPM927 (Smovkina et al., 1990)), R4 integrase (e.g. in pAT98 (Matsuura et al., 1996)), VWB integrase (e.g. in pKT02 (Van Mellaert et al., 1998)), and L5 integrase (e.g. Lee et al., 1991). One skilled in the art will recognise that there are many Actinomycete phages which may be expected to contain integration functions that could be transferred to a delivery vector along with a suitable promoter to generate further systems that can be used to introduce genes into *S. hygroscopicus*. Indeed many further *S. hygroscopicus* phages have been identified and integration functions could be obtained from those and utilised in a similar way. As more phages are characterised one would expect there to be further available integrases that could be used similarly. In some cases this may need alteration of the host strain by addition of the specific attB site for the integrase to enable high efficiency integration. Introduction of auxiliary genes under an appropriate promoter can also be effected by, without limitation, homologous recombination into a neutral position in the chromosome, homologous recombination into a non-neutral position in the chromosome (for example to disrupt a chosen gene). Self-replicating vectors can also be used for example, but not limited to, vectors containing the *Streptomyces* origin of replication from pSG5 (e.g. pKC1139 Bierman et al., 1992), pIJ101 (e.g. pIJ487, Kieser et al., 2000) and SCP2* (e.g. pIJ698, Kieser et al., 2000). More than one of the above systems may be employed in the engineering of a recombinant strain to generate a 17-desmethylrapamycin analogue. One skilled in the art will recognise that it is also possible to generate biosynthetic pathways that will produce the same products as deletion of all the auxiliary genes and complementation in trans, by inactivating or deleting each auxiliary gene as appropriate. Expression of such genes within said host cell, with the feeding of free acids where appropriate, leads to the production of 17-desmethylrapamycin analogues which have incorporated natural or non-natural starter acids and/or which have altered levels of post polyketide processing. In a further embodiment, the altered rapamycin PKS can be expressed in a heterologous host cell which naturally lacks the rapamycin auxiliary genes (or equivalents thereof) together with a selection of said auxiliary genes. In a preferred embodiment, at least rapK is deleted or RapK is otherwise absent from the host strain, and a variety of exogenous carboxylic acids can be fed to said host strain to produce 17-desmethylrapamycin analogues which have incorporated non-natural starter acids.

In a further aspect of the invention, the above modifications are combined, therefore the present invention provides a method for making a 17-desmethylrapamycin analogue, said method comprising:
  (a) generating a recombinant strain in which the methylmalonyl-CoA specific AT domain of module 10 of the rapamycin PKS has been replaced with a malonyl-CoA specific AT domain,
  (b) additionally deleting or inactivating one or more rapamycin auxiliary genes selected from rapI, rapJ, rapK, rapL, rapM, rapN, rapO and rapQ,
  (c) optionally re-introducing all or a subset of auxiliary genes in-trans to complement or partially complement the deletion,
  (d) feeding non-natural starter acids to said recombinant strain under suitable conditions for the production of polyketids, and
  (e) optionally isolating the compound thus produced.

In a preferred embodiment, the auxiliary gene(s) which have been deleted or inactivated include rapK.

In a preferred embodiment, in step (b) all the rapamycin auxiliary genes are deleted or inactivated. In a specific aspect, the present invention provides an alternative method for generating 17-desmethylrapamycin analogues which have incorporated non-natural starter acids by genetically complementing the recombinant strain in which all of the rapamycin auxiliary genes have been deleted or inactivated with the rapamycin auxiliary genes rapI rapJ, rapL, rapM, rapN, rapO and rapQ or their homologues, generating a strain containing all the auxiliary genes except rapK, and feeding with exogenous starter acids. In a preferred embodiment the exogenous non-natural starter acid is cyclohexanecarboxylic acid. In an alternative preferred embodiment the non-natural starter acid is 3-methylcyclohexanecarboxylic acid. In an alternative preferred embodiment the non-natural starter acid is cycloheptanecarboxylic acid. In an alternative preferred embodiment the non-natural starter acid is selected from the group consisting of 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid.

In a further aspect the present invention provides a method for generating 17-desmethylrapamycin analogues by fermentation of the recombinant strain with combinations of auxiliary gene activities and non-natural starter acids. In a preferred embodiment the auxiliary genes that have been deleted are rapK, rapM and rapQ and the non-natural starter acid fed to this strain is cyclohexanecarboxylic acid. In an alternative preferred embodiment the non-natural starter acid fed to this strain with deleted rapK, rapM and rapQ is 3-methylcyclohexanecarboxylic acid. In an alternative preferred embodiment the non-natural starter acid fed to this strain with deleted rapK, rapM and rapQ is cycloheptanecarboxylic acid. In a preferred embodiment the auxiliary genes that have been deleted are rapK, rapM and rapQ and the non-natural starter acid fed to this strain is selected from the group consisting of 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid.

In a further preferred embodiment the auxiliary genes that have been deleted are rapK, rapI and rapQ and the non-natural starter acid fed to this strain is selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the auxiliary genes that have been deleted are rapK, rapI and rapQ and the non-natural starter acid fed to this strain is 3-methylcyclohexanecarboxylic acid. In a more highly preferred embodiment the auxiliary genes that have been deleted are rapK, rapI and rapQ and the non-natural starter acid fed to this strain is cyclohexanecarboxylic acid.

In an alternative preferred embodiment the auxiliary genes that have been deleted are rapK and rapM and the non-natural starter acid fed to this strain is selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the non-natural starter acid fed is cyclohexanecarboxylic acid.

In a further alternative preferred embodiment, the auxiliary genes that have been deleted are rapK, rapI and rapM and the non-natural starter acid fed to this strain is selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the non-natural starter acid fed is cyclohexanecarboxylic acid.

In an alternative preferred embodiment, the auxiliary genes that have been deleted are rapK, rapI, rapJ and rapQ and the non-natural starter acid fed to this strain is selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the non-natural starter acid fed is cyclohexanecarboxylic acid.

In an alternative preferred embodiment, the auxiliary genes that have been deleted are rapK, rapJ, rapM and rapQ and the non-natural starter acid fed to this strain is selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the non-natural starter acid fed is cyclohexanecarboxylic acid.

In a further aspect the present invention provides a method for generating 17-desmethylrapamycin analogues by genetically complementing a recombinant strain in which all of the rapamycin auxiliary genes have been deleted or inactivated with one or more auxiliary genes selected from rapI, rapJ, rapK, rapL, rapM, rapN, rapO and rapQ or their homologues in combination with feeding natural or non-natural starter acids. In a preferred embodiment said recombinant strain is genetically complemented with rapI, rapJ, rapN, rapO and rapL and fed with a non-natural starter acid selected from the group consisting of cyclohexanecarboxylic acid, 3-methylcyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a preferred embodiment said recombinant strain is genetically complemented with rapJ, rapN, rapO and rapL and fed with a non-natural starter acid selected from the group consisting of cyclohexanecarboxylic acid, 3-methylcyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid.

In an alternative preferred embodiment said recombinant strain is genetically complemented with rapJ, rapM, rapN, rapO and rapL and fed with a starter acid selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the starter acid fed is 3-methylcyclohexanecarboxylic acid.

In an alternative preferred embodiment said recombinant strain is genetically complemented with rapI, rapJ, rapN, rapO, rapQ and rapL and fed with a starter acid selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the starter acid fed is cyclohexanecarboxylic acid.

In an alternative preferred embodiment said recombinant strain is genetically complemented with rapJ, rapN, rapO, rapQ and rapL and fed with a starter acid selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the starter acid fed is cyclohexanecarboxylic acid.

In an alternative preferred embodiment said recombinant strain is genetically complemented with rapM, rapN, rapO and rapL and fed with a starter acid selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the starter acid fed is cyclohexanecarboxylic acid.

In an alternative preferred embodiment said recombinant strain is genetically complemented with rapI, rapN, rapO and rapL and fed with a starter acid selected from the group consisting of 3-methylcyclohexanecarboxylic acid, cyclohexanecarboxylic acid, cycloheptanecarboxylic acid, 3-fluoro-4-hydroxycyclohexanecarboxylic acid, 4-fluoro-3-hydroxycyclohexanecarboxylic acid, 3-chloro-4-hydroxycyclohexanecarboxylic acid and 4-chloro-3-hydroxycyclohexanecarboxylic acid. In a more highly preferred embodiment the starter acid fed is cyclohexanecarboxylic acid.

In a further aspect, the present invention provides a method for generating a library of 17-desmethylrapamycin analogues, said method comprising:

(a) generating a recombinant strain in which the methylmalonyl-CoA specific AT domain of module 10 of the rapamycin PKS has been replaced with a malonyl-CoA specific AT domain,
(b) optionally deleting or inactivating one or more rapamycin auxiliary genes selected from rapI, rapJ, rapK, rapL, rapM, rapN, rapO and rapQ,
(c) optionally re-introducing all or a subset of the rapamycin auxiliary genes in-trans to complement or partially complement the deletion, and,
(d) feeding an array of non-natural starter acids to said recombinant strain to generate a number of 17-desmethylrapamycin analogues;
(e) feeding natural or novel amino acids under suitable conditions for the production of polyketides,
(f) optionally isolating the compounds thus produced, and
(g) optionally performing semi-synthesis on the rapamycin analogues isolated.

The present invention is further illustrated by the following examples, which should in no way be construed as limiting the scope of the invention.

EXAMPLES

Materials

All molecular biology enzymes and reagents were obtained from commercial sources.

Bacterial Strains and Growth Conditions

*Escherichia coli* DH10B (GibcoBRL) was grown in 2×TY medium as described by Sambrook et al., (1989) and *E. coli* ET12567 (pUZ8002) as described in Paget et al. (1999) in 2×TY medium with kanamycin (25 mg/L). The vector pUC18 was obtained from New England Biolabs. Vector pKC1139 is described in Practical *Streptomyces* Genetics, Kieser et al., (2000). *E. coli* transformants were selected for with 100 mg/L ampicillin or 50 mg/L apramycin.

*S. hygroscopicus* MG2-10 (WO 04/007709; Gregory et al., 2004) and its derivatives were maintained on medium 1 agar plates (see below) at 28° C., and cultivated in TSBGM (Tryptic Soy Broth with 1.0% glucose and 100 mM MES, pH 6.0) as described in (Khaw et al., 1998), supplemented with 50 mg/L apramycin when required.

Liquid cultures were grown at 28° C. in Erlenmeyer flasks or falcon tubes with shaking at 300 rpm.

Feeding Methods:

Spore stocks of all strains were prepared after growth on medium 1, preserved in 20% w/v glycerol:10% w/v lactose in distilled water and stored at −80° C. Vegetative cultures were prepared by inoculating 0.1 mL of frozen stock into 50 mL medium 2 (see below) in 250 mL flask. The culture was incubated for 36 to 48 hours at 28° C., 300 rpm.

Feeding procedure: Vegetative cultures were inoculated at 0.5 mL into 7 mL medium 3 in 50 mL tubes. Cultivation was carried out for 7 days, 26° C., 300 rpm. The feeding/addition of the selected carboxylic acids ("non-natural starters" or "natural starters") were carried out at 24 hours after inoculation and were fed at 1 mM unless stated otherwise.

Medium 1:

| component | Source | Catalogue # | Per L |
|---|---|---|---|
| Corn steep powder | Sigma | C-8160 | 2.5 g |
| Yeast extract | Difco | 0127-17 | 3 g |
| Calcium carbonate | Sigma | C5929 | 3 g |
| Iron sulphate | Sigma | F8633 | 0.3 g |
| BACTO agar | | | 20 g |
| Wheat starch | Sigma | S2760 | 10 g |
| Water to | | | 1 L |

The media was then sterilised by autoclaving 121° C., 20 min.

Medium 2: RapV7 Seed medium

| Component | Per L |
|---|---|
| Soy bean flour (Nutrisoy) | 5 g |
| Avedex W80 dextrin (Deymer Ingredients Ltd) | 35 g |
| Corn Steep Solids (Sigma) | 4 g |
| Glucose | 10 g |
| (NH$_4$)$_2$SO$_4$ | 2 g |
| Lactic acid (80%) | 1.6 mL |
| CaCO$_3$(Sigma) | 7 g |

Adjust pH to 7.5 with 1 M NaOH.
The media was then sterilised by autoclaving 121° C., 20 min.
After sterilisation 0.16 mL of 4% glucose is added to each 7 mL of media.

Medium 3: MD6 medium (Fermentation medium)

| Component | Per L |
|---|---|
| Soy bean flour (Nutrisoy) | 30 g |
| Corn starch (Sigma) | 30 g |
| Avedex W80 dextrin (Deymer Ingredients Ltd) | 19 g |
| Yeast (Allinson) | 3 g |
| Corn Steep Solids (Sigma) | 1 g |
| KH$_2$PO$_4$ | 2.5 g |
| K$_2$HPO$_4$ | 2.5 g |
| (NH$_4$)$_2$SO$_4$ | 10 g |
| NaCl | 5 g |
| CaCO$_3$ (Caltec) | 10 g |
| MnCL$_2$4H$_2$O | 10 mg |
| MgSO$_4$7H$_2$O | 2.5 mg |
| FeSO$_4$7H$_2$O | 120 mg |
| ZnSO$_4$7H$_2$O | 50 mg |
| MES (2-morpholinoethane sulphuric acid monohydrate) | 21.2 g | pH is corrected to 6.0 with 1 M NaOH
Before sterilization 0.4 mL of Sigma α-amylase (BAN 250) was added to 1 L of medium.
Medium was sterilised for 20 min at 121° C.
After sterilisation 0.35 mL of sterile 40% fructose and 0.10 mL of L-lysine (140 mg/mL in water, filter-sterilsed) was added to each 7 mL.

Medium 4: RapV7a Seed medium

| Component | Per L |
|---|---|
| Soy bean flour (Nutrisoy) | 5 g |
| Avedex W80 dextrin (Deymer Ingredients Ltd) | 35 g |
| Corn Steep Solids (Sigma) | 4 g |
| (NH$_4$)$_2$SO$_4$ | 2 g |
| Lactic acid (80%) | 1.6 mL |
| CaCO$_3$(Sigma) | 7 g |

Adjust pH to 7.5 with 1 M NaOH.
The media was then sterilised by autoclaving 121° C., 20 min.

| Medium 5: MD6/5-1 medium (Fermentation medium) | |
|---|---|
| Component | Per L |
| Soy bean flour (Nutrisoy) | 15 g |
| Avedex W80 dextrin (Deymer Ingredients Ltd) | 50 g |
| Yeast (Allinson) | 3 g |
| Corn Steep Solids (Sigma) | 1 g |
| $KH_2PO_4$ | 2.5 g |
| $K_2HPO_4$ | 2.5 g |
| $(NH_4)_2SO_4$ | 10 g |
| NaCl | 13 g |
| $CaCO_3$ (Caltec) | 10 g |
| $MnCl_2 4H_2O$ | 3.5 mg |
| $MgSO_4 7H_2O$ | 15 mg |
| $FeSO_4 7H_2O$ | 150 mg |
| $ZnSO_4 7H_2O$ | 60 mg |
| SAG 471 | 0.1 ml |

Medium was sterilised for 30 min at 121° C.
After sterilisation 15 g of Fructose per L was added.

In Vitro Bioassay for Anticancer Activity

In vitro evaluation of compounds for anticancer activity in a panel of 12 human tumour cell lines in a monolayer proliferation assay were carried out at the Oncotest Testing Facility, Institute for Experimental Oncology, Oncotest GmbH, Freiburg. The characteristics of the 12 selected cell lines are summarised in Table 1.

TABLE 1

| Test cell lines | | |
|---|---|---|
| # | Cell line | Characteristics |
| 1 | SF-268 | CNS, NCI standard |
| 2 | GXF 251L | Gastric |
| 3 | NCI-H460 | Lung, NCI standard |
| 4 | MCF-7 | Breast, NCI standard |
| 5 | MEXF 394NL | Melanoma |
| 6 | OVCAR-3 | Ovarian - p85 mutated. AKT amplified. |
| 7 | DU145 | Prostate - PTEN positive |
| 8 | LNCAP | Prostate - PTEN negative |
| 9 | UXF 1138L | Uterus |

The Oncotest cell lines were established from human tumor xenografts as described by Roth et al. 1999. The origin of the donor xenografts was described by Fiebig et al. 1992. Other cell lines were either obtained from the NCI (H460, SF-268, OVCAR-3, DU145, MDA-MB-231, MDA-MB-468) or purchased from DSMZ, Braunschweig, Germany (LNCAP).

All cell lines, unless otherwise specified, are grown at 37° C. in a humidified atmosphere (95% air, 5% $CO_2$) in a 'ready-mix' medium containing RPMI 1640 medium, 10% fetal calf serum, and 0.1 mg/mL gentamicin (PAA, Cölbe, Germany).

Monolayer Assay:

A modified propidium iodide assay was used to assess the effects of the test compound(s) on the growth of twelve human tumor cell lines (Dengler et al., 1995).

Briefly, cells were harvested from exponential phase cultures by trypsinization, counted and plated in 96 well flat-bottomed microtitre plates at a cell density dependent on the cell line (5-10.000 viable cells/well). After 24 h recovery to allow the cells to resume exponential growth, 0.01 mL of culture medium (6 control wells per plate) or culture medium containing 39-desmethoxyrapamycin were added to the wells. Each concentration was plated in triplicate. 39-Desmethoxyrapamycin was applied in two concentrations (0.001 mM and 0.01 mM). Following 4 days of continuous incubation, cell culture medium with or without 39-desmethoxyrapamycin was replaced by 0.2 mL of an aqueous propidium iodide (PI) solution (7 mg/L). To measure the proportion of living cells, cells were permeabilized by freezing the plates. After thawing the plates, fluorescence was measured using the Cytofluor 4000 microplate reader (excitation 530 nm, emission 620 nm), giving a direct relationship to the total number of viable cells.

Growth inhibition was expressed as treated/control×100 (% T/C) and are provided for a selection of cell lines. For active compounds, the average $IC_{50}$ & $IC_{70}$ values across the entire cell line panel examined were estimated by plotting compound concentration versus cell viability and are also provided.

Example 1

Isolation of the Engineered Strain *S. hygroscopicus* MG7-9 i) Generation of Plasmid pALK83

Primers MG308 5'-GTCCTAGGTGATGTCCCGGCAA-CACG-3' (SEQ ID NO: 13) and MG309 5'-CACCTGCAG-GCCCAACTCGGCCAGCTCGCT-3' (SEQ ID NO: 14) were used to amplify a region of homology upstream of the Rapamycin module 10 acyl transferase (rapAT10) (from nt11693 to nt13289 in the rapamycin cluster as described in Schwecke et al., 1995) using cosmid DNA (cos 26, see Schwecke et al., 1995) prepared from *S. hygroscopicus* NRRL5491 as a template. The 1596 bp PCR product (SEQ ID NO: 15) was phosphorylated using T4 polynucleotide kinase and ligated into SmaI digested pUC18 which had been dephosphorylated. After transformation into *E. coli* DH10B, the plasmid pMG255-4 was isolated. The primers MG310 5'-CCTGGCCAGGAAAGACGAACACGATCCT-3' (SEQ ID NO: 16) and MG311 5'-CGAAGCTTGAGCCGCTGGC-GATCGTGGGA-3' (SEQ ID NO: 17) were used to amplify a region of homology downstream of the Rapamycin module 10 AT (from nt14191 to nt15742 in the rapamycin cluster as described in Schwecke et al., 1995) using cosmid DNA (cos 26, see Schwecke et al., 1995) prepared from *S. hygroscopicus* NRRL5491 as a template. The 1551 bp PCR product (SEQ ID NO: 18) was phosphorylated using T4 polynucleotide kinase and ligated into SmaI digested pUC18 which had been dephosphorylated. After transformation into *E. coli* DH10B, the plasmid pMG256-1 was isolated. The integrity of the insert of each plasmid was confirmed by sequence analysis.

Plasmids pCJR26 (Rowe et al., 1998) and pMG256-1 were each transformed into *E. coli* ET12567 and unmethylated (dam⁻, dcm⁻, hsdn⁻) plasmid DNA isolated. The plasmid pMG255-4 was digested with AvrII/HindIII and the approximately 4.3 kbp fragment was isolated; demethylated pCJR26 was digested with MscI/AvrII and the approximately 1 kbp fragment isolated and demethylated pMG256-1 was digested with HindIII, partially digested with MscI and the approximately 1.5 kbp fragment isolated. These three DNA fragments were ligated and used to transform *E. coli* DH10B. The resulting plasmid, pMG291-14 was isolated. This plasmid was digested with HindIII/XbaI and the approximately 4 kbp fragment isolated and ligated into pKC1139 digested with HindIII/XbaI and the DNA was used to transform *E. coli* DH10B. The resulting plasmid, pALK83 contains the rapamycin acyl transferase domain of module 2 flanked with DNA regions to allow homologous recombination into module 10 to effect an AT swap by double recombination.

ii) Isolation of Engineered Strain *S. hygroscopicus* MG7-9

*E. coli* ET12567-harbouring the plasmid pUZ8002 was transformed with pALK83 to generate the *E. coli-donor* strain for conjugation. This was used to transform *S. hygroscopicus* MG2-10 (WO 04/007709; Gregory et al., 2004) by conjugation. An apramycin resistant colony was isolated and patched to media 1 plus 50 mg/L apramycin and 25 mg/L nalidixic acid. This patch was then used to inoculate a flask containing TSBGM with 50 mg/L of apramycin. This culture was incubated for two days at 28° C. followed by two days at 37° C. This culture was streaked to plates of media 1 containing 50 mg/L apramycin and incubated for 7 days at 37° C. Single colonies were re-patched onto plates of media 1 with 50 mg/L apramycin and grown for a further 7 days at 37° C. These patches were used to inoculate flasks of TSBGM with no antibiotic, which were grown for 3 days at 37° C. This culture was streaked to plates of media 1 and single colonies used to patch plates of media 1 with and without apramycin (50 mg/L) to look for sensitivity, representing a second recombination event involving loss of the plasmid backbone. Fourteen apramycin sensitive patches were used to inoculate 14×7 mL of medium 2 (rapV7) and these seed cultures grown for 3 days at 28° C. These were then used to inoculate (0.5 mL into 7 mL) medium 3 (MD6) and cultured for 5 days at 26° C. with feeding of cyclohexanecarboxylic acid to a final concentration of 1 mM after 24 hours. Extracts of these cultures were assessed for production of rapamycin analogues by LCMS. Nine separate cultures were seen to produce a novel compound with the appropriate molecular mass for 17-desmethyl-39-deshydroxypre-rapamycin. One of these cultures was selected on the basis of production level and robustness, to be cultured on a larger scale for isolation of the new compound; this strain was named *S. hygroscopicus* MG7-9.

iii) Analysis of Novel Rapamycin Analogue from *S. hygroscopicus* MG7-9

The observed novel rapamycin analogue was proposed to be the desired 17-desmethyl-39-deshydroxypre-rapamycin on the basis of the following analytical data. The novel rapamycin analogue is more polar (retention time 5.9-6.2 min) than 39-deshydroxypre-rapamycin (retention time 6.35-6.95 min) as would be expected for the loss of a methyl group.

Figure 4:
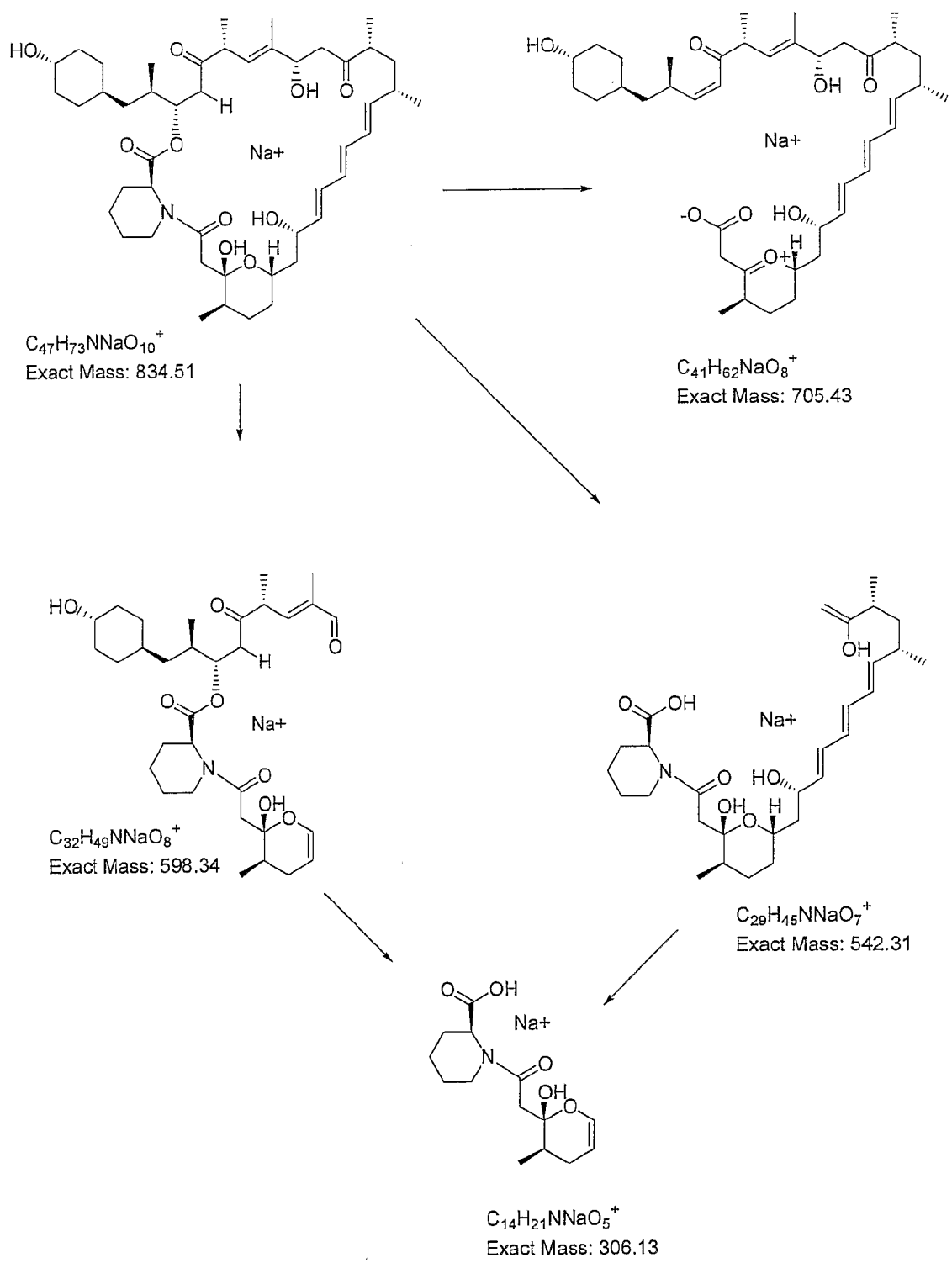
FIG. 4 Fragmentation of 39-desmethoxy-17-desmethyl-pre-rapamycin by mass spectrometry.

LCMS and LCMS$^n$ analysis of MG7-9 extracts showed that the m/z ratio for the novel rapamycin analogue is 14 mass units lower than for 39-deshydroxypre-rapamycin, consistent with the absence of a methyl group. Ions observed: [M-H]$^-$ 810.8, [M+Na]$^+$834.8, [M+K]$^+$850.8. Fragmentation of the sodium adduct gave the predicted ions for 17-desmethyl-39-desmethoxypre-rapamycin following a previously identified fragmentation pathway (FIG. 4) (J. A. Reather, Ph.D. Dissertation, University of Cambridge, 2000). This mass spectrometry fragmentation data narrows the region of the novel rapalogue where the loss of a methyl has occurred in the fragment C16-C27 which in native form contains 3 methyl groups. These methyls are attached at C17 (triene), C23 (1 carbon removed from the triene) and C25 (3 carbons removed from the triene). The UV triene characteristic of rapamycin is observed but the UV maximum of the central peak has shifted (λ=270 nm c.f. λ=278 nm for 39-deshydroxypre-rapamycin). This strongly indicates that there has been a change to the functionality on the triene, as such changes in wavelength are not observed for changes in functionality at C16 (OH/OCH$_3$); the observed change is in keeping with that expected for the loss of a methyl group at C17.

Figure 5:
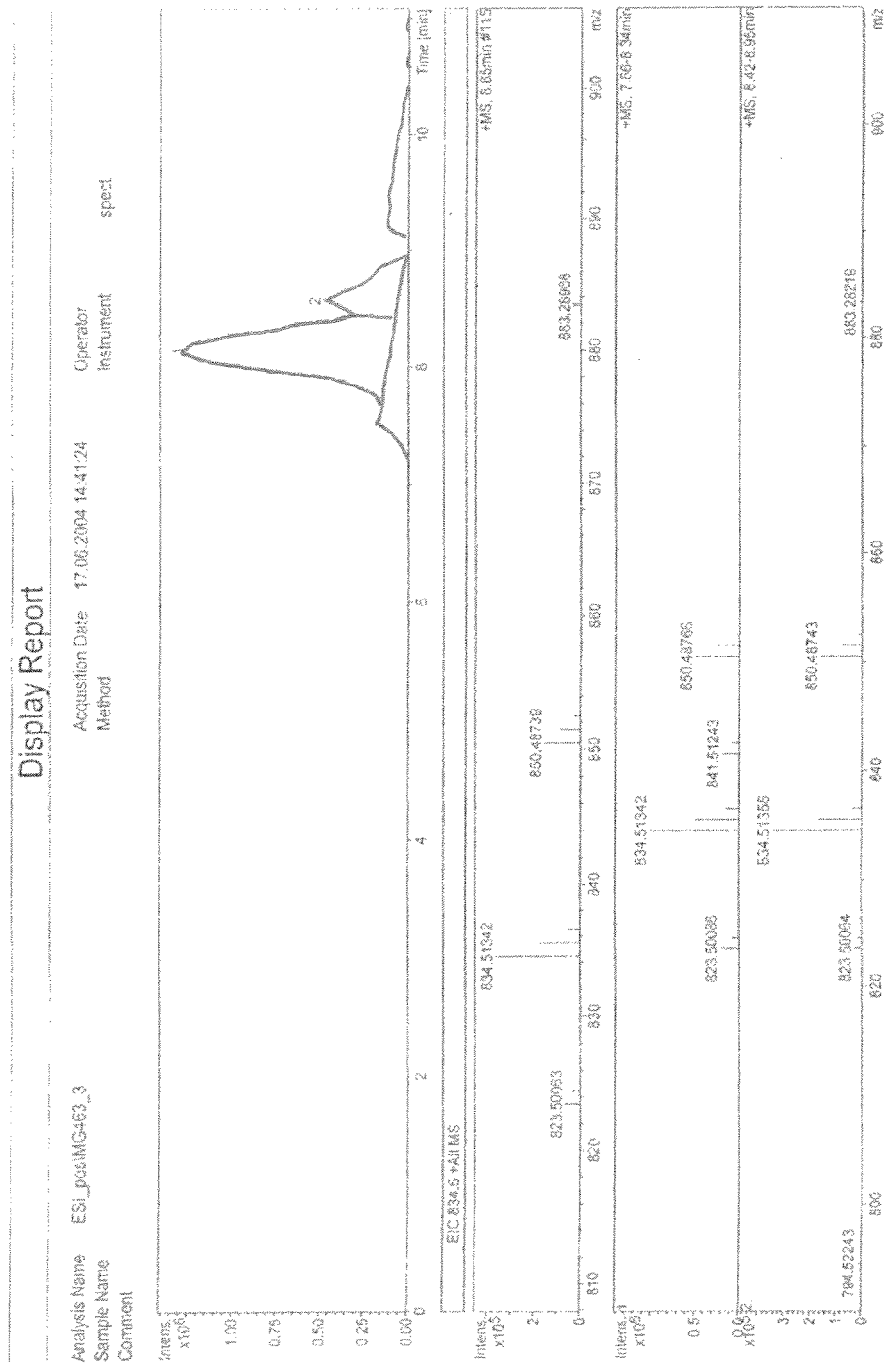
FIG. 5 LC-FT-ICR-MS analysis of 17-desmethyl-39-deshydroxypre-rapamycin.

The accumulated product was also analysed by LC high resolution-Fourier transform-ion cyclotron resonance, mass spectrometry (LC-FT-ICR-MS). Accurate mass data was obtained for the sodium adduct of the parent ion (found: 834.51342 (FIG. 5, A), C$_{47}$H$_{73}$NO$_{10}$Na calculated: 834.51319, deviation 0.28 ppm) and key daughter ions as tabulated below (see attached FIG. 4 for fragmentation pathway).

| Fragment | formula | Found | Calculated | Deviation |
|---|---|---|---|---|
| A | C$_{41}$H$_{62}$O$_8$Na | 705.43403 | 705.43422 | 0.27 ppm |
| B | C$_{40}$H$_{62}$O$_6$Na | 661.44495 | 661.44439 | 0.84 ppm |
| C | C$_{23}$H$_{34}$O$_5$Na | 413.22953 | 413.23038 | 2.05 ppm |

Figure 6:
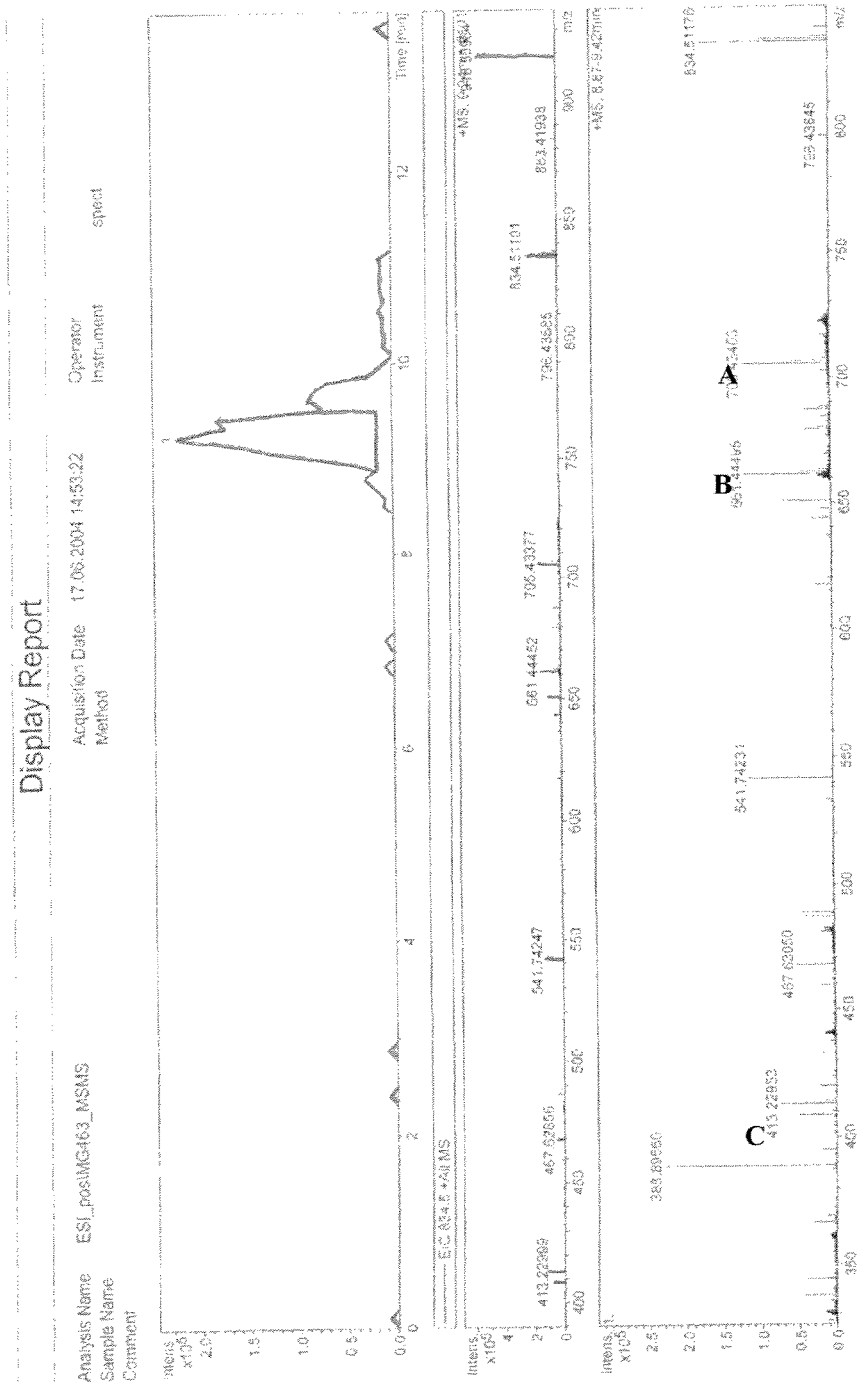
FIG. 6. LC-FT-ICR-MS" analysis of 17-desmethyl-39-deshydroxypre-rapamycin.

(see also FIG. 6)

This mass spectrometry fragmentation data is entirely consistent with 17-desmethyl-39-deshydroxypre-rapamycin.

iv) Fermentation of the Novel Rapamycin Analogue for Isolation

Spore stocks of all strains were prepared after growth on medium 1, preserved in 20% w/v glycerol:10% w/v lactose in distilled water and stored at −80° C. Primary vegetative cultures were prepared by inoculating 0.1 mL of frozen stock into 50 mL medium 4 in a 250 mL flask. The culture was incubated for 48 hours at 28° C. with shaking at 250 rpm. The culture was then subcultured to 400 mL medium 4 in 2000 mL flasks to give the secondary vegetative culture. The culture was incubated for 24 hrs at 28° C., 250 rpm.

Vegetative cultures were inoculated at 7.5% v/v into 15 L of medium 5 (see above) in a 20 L fermentor. Cultivation was carried out for 6 days at 26° C., 0.5 vvm≧30% dissolved oxygen minimum tip speed of 1.18 ms$^{-1}$ maximum tip speed of 2.75 ms$^{-1}$. The feeding of cyclohexanecarboxylic acid was carried out at 24 and 48 hours after inoculation to give a final concentration of 2 mM/L. 48 hours after inoculation 9.5 g of L-lysine was added in 200 mL of water.

v) Extraction and Purification

The fermentation broth (12 L) was stirred with an equal volume of methanol for 2 hours and then centrifuged to pellet the cells (10 min, 3500 rpm). The supernatant was stirred with Diaion® HP20 resin (43 g/L) for 1.5 hours and then filtered. The resin was washed batchwise with acetone (total volume 7.5 L) to strip off the rapalogue and the solvent removed in vacuo. The resulting aqueous concentrate (800 mL) was then diluted to 1 L with water and extracted with EtOAc (3×1 L). The solvent was removed in vacuo to give a sticky brown extract (10.9 g). The extract was dissolved in acetone (ca 20 mL), coated onto silica, applied to a silica column (3×6.5 cm diameter) and eluted with a stepwise gradient of acetone/hexane (20%-40%). The rapalogue-containing fractions were pooled and the solvent removed in vacuo. The residue (840 mg) was further chromatographed over Sephadex LH20, eluting with 10:10:1 chloroform/heptane/ethanol. The semipurified rapalogue (151 mg) was dissolved in acetonitrile (2.7 mL), centrifuged (10 min, 13200 rpm) and purified by reverse phase (C18) preparative HPLC using a Gilson HPLC, eluting a Phenomenex 21.2×250 mm Luna 5 μm C18 BDS column with 21 mL/min of 60% acetonitrile/water. The most pure fractions (identified by analytical HPLC) were combined and the solvent removed in vacuo to give 17-desmethyl-39-deshydroxypre-rapamycin (10 mg).

vi) Characterisation

Figure 7:
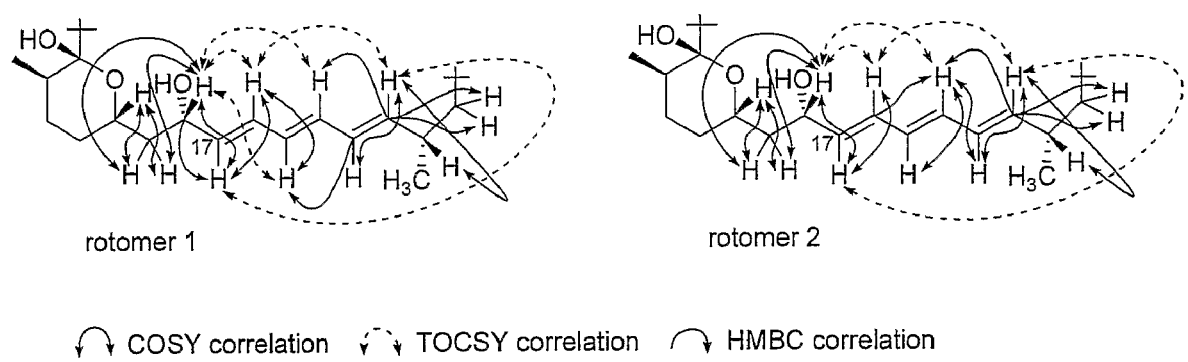
FIG. 7. Significant NMR correlations for 17-desmethyl-39-deshydroxypre-rapamycin.

A range of NMR experiments were performed viz $^1$H, $^{13}$C, APT, COSY, HMQC, HMBC, TOCSY. A thorough and exhaustive review of these data enabled the assignment of the majority of the protons and carbons of both rotomers of 17-desmethyl-39-deshydroxypre-rapamycin. The absence of an olefinic methyl resonance was immediately apparent from the $^1$H NMR spectrum. Correlations between H16 and an olefinic methine (not present in the spectrum of 39-deshydroxypre-rapamycin) could be seen in the COSY spectrum confirming the compound to be lacking a methyl group at C-17. Important NMR correlations are shown in FIG. 7 for the C17 containing portion of each of the known rotamers of the compounds (variation between the two is at the amide portion of the structure which is not shown).

TABLE 2

$^1$H and $^{13}$C NMR data for 17-desmethyl-39-deshydroxypre-rapamycin

| Proton | $\delta_H$ | | multiplicity | | coupling | | $\delta_C$ | |
|---|---|---|---|---|---|---|---|---|
| 1 | | | | | | | 171.6 | 169.0 |
| 2 | 5.38 | 4.37 | | | | | 52.6 | 55.7 |
| 3a | 1.73 | 1.50 | | | | | 26.2 | 26.7 |
| 3b | 2.20 | 2.40 | | | | | | |
| 4a | 1.28 | | | | | | 20.9 | 20.6 |
| 4b | 1.73 | 1.69 | | | | | | |
| 5a | 1.48 | 1.32 | | | | | 25.1 | 24.4 |
| 5b | 1.72 | 1.63 | | | | | | |
| 6a | 3.26 | 2.21 | | | | | 44.5 | 39.0 |
| 6b | 3.82 | 4.50 | br. d | br. d | 12.8 | 10.0 | | |
| 8 | | | | | | | 172.4 | 171.9 |
| 9a | 2.53 | 2.47 | | | | | 40.4 | 39.0 |
| 9b | 2.95 | 2.67 | d | | 13.7 | | | |
| 10 | | | | | | | 98.7 | 98.4 |
| 11 | 1.53 | 1.41 | | | | | 38.6 | 38.5 |
| 12a | | 1.51 | | | | | 27.6 | 27.5 |
| 12b | 1.63 | 1.68 | | | | | | |
| 13a | 1.33 | 1.30 | | | | | 31.9 | 32.1 |
| 13b | 1.51 | 1.55 | | | | | | |
| 14 | 3.99 | 4.25 | | | | | 68.9 | 70.8 |
| 15a | 1.51 | 1.50 | | | | | 43.1 | 40.3 |
| 15b | 1.66 | 1.74 | | | | | | |
| 16 | 4.24 | 4.44 | | | | | 70.3 | 71.3 |
| 17 | 5.60 | 5.86 | dd | m | 15.1, 4.8 | | 135.7 | 137.1 |
| 18 | 6.39 | 6.13 | ddd | | 15.1, 10.1, 1.5 | | 129.2$^a$ | 127.9 |
| 19 | 6.07 | 6.13 | | | | | 131.4$^b$ | 132.1$^c$ |
| 20 | 6.11 | 6.06 | | | | | 131.9$^c$ | 131.6$^b$ |
| 21 | 5.98 | 5.96 | dd | dd | 15.0, 9.9 | 14.9, 10.0 | 129.9 | 129.1$^a$ |
| 22 | 5.28 | 5.24 | dd | dd | 15.0, 9.6 | 14.9, 9.8 | 139.7 | 140.6 |
| 23 | 2.16 | 2.10 | | | | | 38.0 | 39.8 |
| 24a | 1.31 | 1.35 | | | | | 40.0 | 40.6 |
| 24b | 1.75 | 1.98 | | | | | | |
| 25 | 2.41 | 2.44 | | | | | 45.9 | 46.6 |
| 26 | | | | | | | 215.7 | 216.6 |
| 27a | 2.50 | 2.39 | | | | | 46.7 | 48.2 |
| 27b | 2.68 | 2.63 | | | | | | |
| 28 | 4.32 | 4.36 | dd | | 8.5, 2.2 | | 71.5 | 71.9 |
| 29 | | | | | | | 139.1 | 139.4 |
| 30 | 5.34 | 5.50 | | | | | 123.7 | 125.0 |
| 31 | 3.30 | 3.37 | dq | dq | 9.7, 6.7 | 10.0, 6.7 | 46.4 | 45.9 |
| 32 | | | | | | | 208.8 | 209.1 |
| 33a | 2.62 | 2.65 | | | | | 41.1 | 39.5 |
| 33b | 2.62 | 2.76 | | dd | | 18.1, 9.8 | | |
| 34 | 5.14 | 5.34 | | | | | 76.3 | 74.6 |
| 35 | 1.88 | 1.94 | | | | | 32.9 | 32.9 |
| 36a | 0.99 | 0.97 | | | | | 37.9 | 40.0 |
| 36b | 1.11 | 1.10 | | | | | | |
| 37 | 1.23 | | | | | | 33.7 | 33.8 |
| 38a | 0.79 | 0.88 | | | | | 30.2 | 30.8 |
| 38b | 1.72 | 1.76 | | | | | | |
| 39a | 1.17 | 1.20 | | | | | 35.2 | 35.3 |
| 39b | 1.94 | | | | | | | |
| 40 | 3.53 | 3.53 | | | | | 71.0 | 71.0 |
| 41a | 1.28$^e$ | 1.26$^e$ | | | | | 35.5 | 35.5 |
| 41b | | | | | | | | |
| 42a | | | | | | | 32.5 | 31.9 |
| 42b | | | | | | | | |
| 43 | 0.95 | 0.94 | d | d | 6.4 | 6.7 | 16.7 | 16.9 |
| 44 | 1.02 | 1.00 | d | d | 6.4 | 6.7 | 21.7$^d$ | 21.6$^d$ |
| 45 | 1.00 | 1.03 | d | d | 6.7 | 7.0 | 17.1 | 19.3 |
| 46 | 1.61 | 1.51 | d | d | 1.0 | 0.9 | 13.5 | 12.1 |
| 47 | 1.07 | 1.04 | d | d | 6.8 | 6.7 | 16.0 | 14.5 |
| 48 | 0.87 | 0.88 | d | d | 7.2 | 7.4 | 16.1 | 15.0 |

$^{a,b,c,d,e}$these assignments may be interchanged
NMR data obtained in CDCl$_3$ at 500 MHz for $^1$H-NMR and 125 for $^{13}$C-NMR.

Example 2

Array Feed of Starter Acids to *S. hygroscopicus* MG7-9

TABLE 3

Sources of acids for use in the array feeding experiment

| Acid | Company | Stock number | synthesis |
|---|---|---|---|
| cyclohexanecarboxylic acid | Aldrich | 10,183-4 | |
| (1R*,3R*,4R*)-3,4-dihydroxycyclohexanecarboxylic acid | | | in house by method A |
| 1-cyclohexenecarboxylic acid | Aldrich | 32,836-7 | |
| 3-cyclohexenecarboxylic acid | Aldrich | 45,375-7 | |
| cycloheptanecarboxylic acid | Aldrich | C9,850-0 | |
| ethyl (1R*,5R*)-5-hydroxycyclohex-3-enecarboxylate | | | in house by method B |
| ethyl (1R*,4R*)-3-fluoro-4-hydroxycyclohexane carboxylate | | | in house by method C |
| 3-(cis/trans)-methylcyclohexanecarboxylic acid | Aldrich | 33,061-2 | |

Method A: Synthesis of (1R*,3R*,4R*)-3,4-dihydroxycyclohexanecarboxylic acid

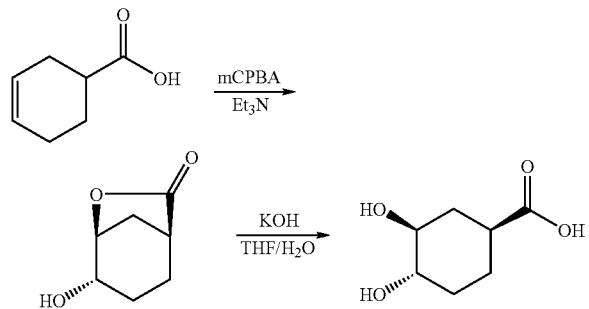

(1R*,3R*,4R*)-3,4-Dihydroxycyclohexanecarboxylic acid was readily attainable from commercially available racemic 3-cyclohexene carboxylic acid. This acid was epoxidised through treatment with meta-chloroperbenzoic acid and converted to the (1R*,3R*,4R*)-4-hydroxycyclohexane-1,3-carbolactone in situ by the addition of base (triethylamine), thus setting up the relative stereochemistries. This lactone was then hydrolysed by the action of aqueous potassium hydroxide, and the final product purified over ion exchange resin (Corey, E. J. and Huang, H.1989).

Method B: Synthesis of ethyl (1R*,5R*)5-hydroxycyclohex-3-ene carboxylate

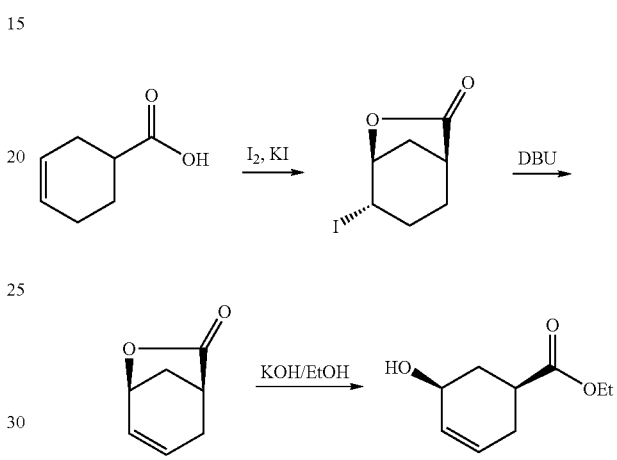

The title compound was prepared, in racemic form, by generating (1R*,3R*,4R*)-4-iodocyclohexane-1,3-carbolactone from cyclohex-3-ene carboxylic acid, which was then treated with the base DBU (1,8-diazabicyclo[5.4.0]undec-7-ene) to eliminate HI. The resultant (1R*,5S*)-cyclohex-3-ene-1,5-carbolactone was then treated with potassium hydroxide dissolved in ethanol to yield the title compound (Marshall, J. A., and Shiping, X., 1995)

Method C: Synthesis of ethyl (1R*,4R*)-3-fluoro-4-hydroxycyclohexane carboxylate

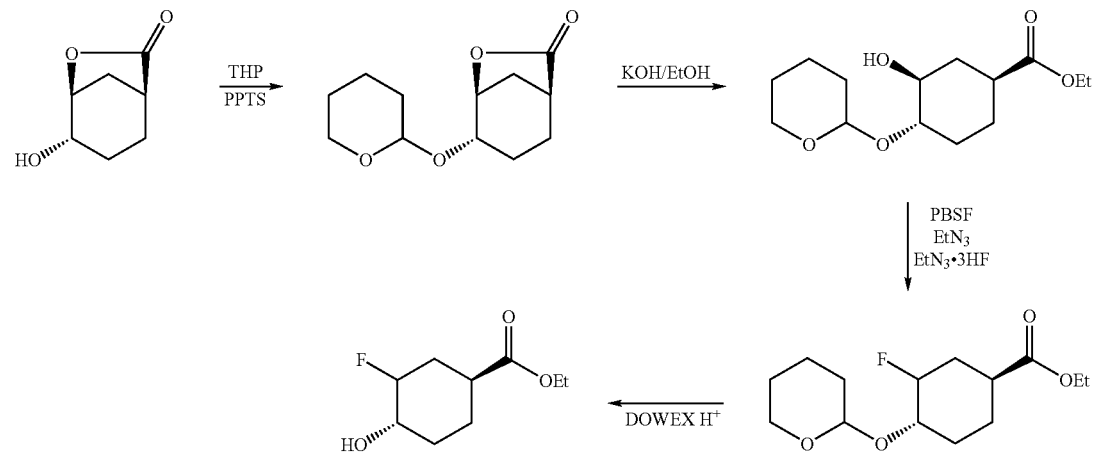

(1R*,3R*,4R*)-4-Hydroxycyclohexane-1,3-carbolactone, prepared as in method A, was protected as (1R*,3R*,4R*)-4-(1-tetrahydropyranyl)oxycyclohexane-1,3-carbolactone, which was treated with potassium hydroxide in ethanol to yield ethyl (1R*,3R*,4R*)-3-hydroxy-4-(1-tetrahydropyranyl)oxycyclohexane carboxylate. Fluorine was introduced into the 3 position, via an activation-substitution method (Yin et al., 2004), and the 4-(1-tetrahydropyranyl) group removed with acidic DOWEX resin.

i) Array Feeding Experiment

*S. hygroscopicus* MG7-9 was grown on media 1 for 14 days at 28° C. until sporulation had occurred. A 0.5 cm diameter section of agar, mycelia and spores was taken from the plate and transferred into 7 mL of media 2 (rapV7) in a 50 mL falcon tube with a foam bung and grown at 28° C. for 48 hours with shaking at 300 rpm. 0.5 mL of this seed culture was then transferred to 7 mL of media 3 (MD6) in a 50 mL falcon tube with a foam bung and grown for 24 hours at 26° C. with shaking at 300 rpm. Each starter acid, dissolved in 0.05 mL of methanol, was fed to appropriate cultures to a final concentration of 2 mM (see table 1 for list of starter acids). The cultures were then grown for a further 4 days at 26° C. 1 mL of culture was then removed from each flask, and added to 1 mL of acetonitrile in a 2 mL eppendorf, agitated for 1 hour at room temperature, and then centrifuged for 15 minutes in a microfuge at 13,000 rpm. 0.2 mL of the top layer was removed into HPLC tubes and analysed by HPLC using UV and LCMS detection.

TABLE 4

Analysis of extracts

| Starter acid feed | Product molecular mass | Product Structure |
|---|---|---|
| (cyclohexane-CO₂H) | 811.52 | Structure A as shown below |
| (3,4-dihydroxycyclohexane-CO₂H) | 827.52 | Structure B as shown below |
| (cyclohexene-CO₂H) | 811.52 | Structure C as shown below |
| (cyclohexadiene-CO₂H) | 809.51 / 827.52 | Structure G as shown below*, unknown additional minor rapalogue |
| (cycloheptane-CO₂H) | 825.54 / 841.53 | Structure D as shown below* unknown additional minor rapalogue |
| (3-hydroxycyclohexene-CO₂H) | 809.51 / 825.50 | Structure H as shown below unknown additional minor rapalogue |

TABLE 4-continued

Analysis of extracts

| Starter acid feed | Product molecular mass | Product Structure |
|---|---|---|
| (4-hydroxy-3-fluorocyclohexane-CO₂H) | 829.51 / 845.51 | Structure E as shown below* unknown additional minor rapalogue |
| (3-methylcyclohexane-CO₂H) | 825.54 / 841.53 | Structure F as shown below* unknown additional minor rapalogue |

*= the regiochemistry and/or stereochemistry of the hydroxyl or fluorine group in the incorporated starter acid has not been determined; this is reflected in the structure diagram below. However, it should be noted that this diagram is intended to reflect the single product obtained, a person of skill in the art will, after following the example above, be able to isolate and characterise this product if desired.

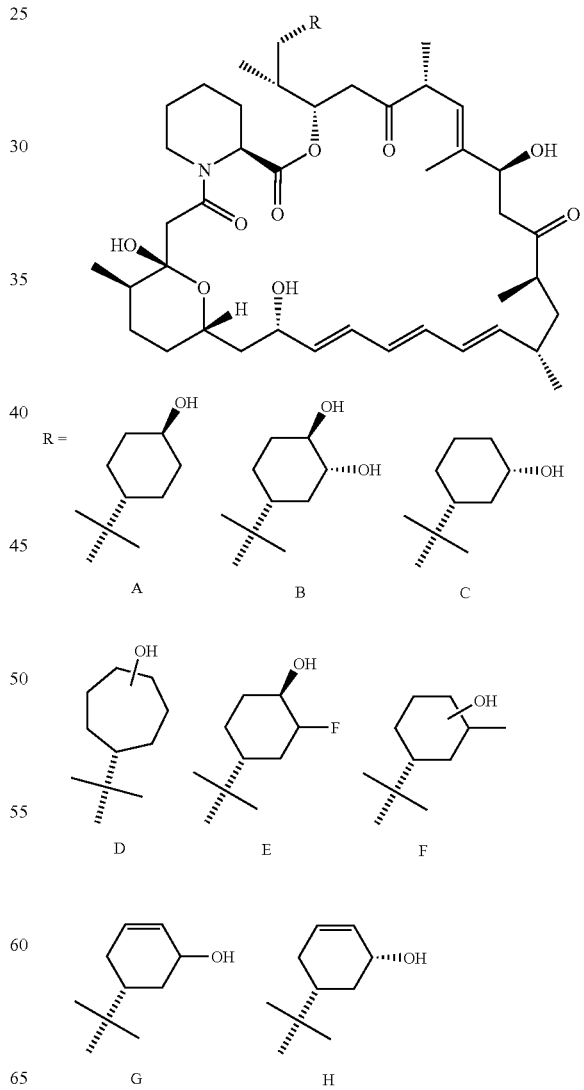

Example 3

Construction of Conjugative Vector pLL150

Figure 8:
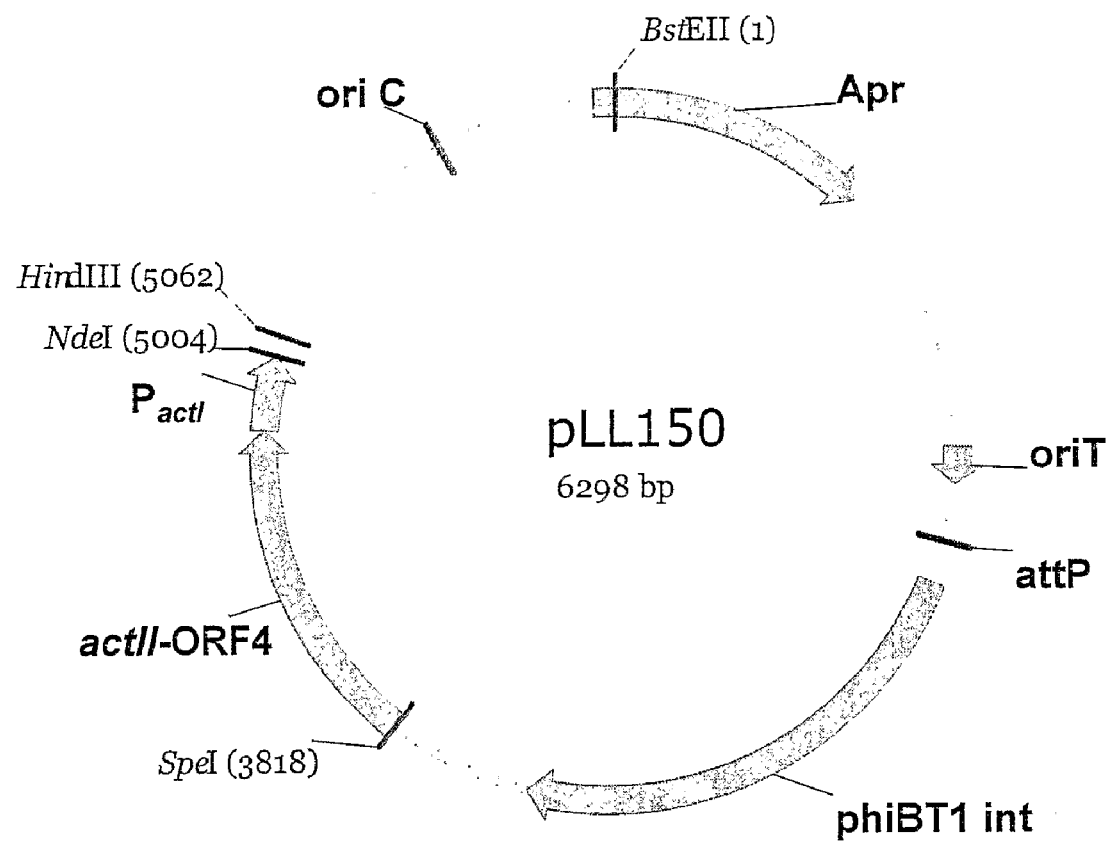
FIG. 8 Diagram of plasmid pLL150.

Plasmid pSGset1 (WO 04/007709) was digested using SpeI and BstEII and the 2.481 kbp fragment was isolated and ligated with vector pRT801 (Gregory et al., 2003) similarly digested with SpeI and BstEII. After transformation into *E. coli* DH10B, colonies were screened by restriction enzyme digestion and the final plasmid pLL150 was isolated. See FIG. 8.

Example 4

Isolation of 17-desmethylrapamycin by complementation of *S. hygroscopicus* MG7-9 with a cassette of auxiliary genes i) Generation of Complementation Plasmid pLL158 Containing the Rapamycin Auxiliary Genes rapK, rapI, rapJ rapN, rapO, rapM, rapQ and rapL (rap KIJN/OMQL)

Plasmid pSGsetrapKIJN/OMQL (WO 04/007709) was digested using SpeI and HindIII and the 8.516 kbp fragment (containing rap KIJN/OMQL) was isolated and ligated with conjugative vector pLL150 similarly digested with SpeI and HindIII. After transformation into *E. coli* DH10B, the final plasmid pLL158 was identified and confirmed by restriction enzyme digestion.

ii) Isolation of Strain *S. hygroscopicus* MG7-9 (pLL158)

*E. coli* ET12567, harbouring the plasmid pUZ8002 was transformed with pLL158 to generate the *E. coli* donor strain for conjugation. This was used to transform *S. hygroscopicus* MG7-9 by conjugation. Apramycin resistant colonies were isolated on media 1 (with 50 mg/L apramycin and 25 mg/L nalidixic acid) and patched to media 1 with 50 mg/L apramycin and 25 mg/L nalidixic acid. These patches were grown at 28° C. before secondary patching onto media ISP3 plus 50 mg/L apramycin and grown for 14-21 days at 28° C. A plug from each patch was used to inoculate individual falcon tubes containing 7 mL media 2 (RapV7) plus 50 mg/L apramycin. These seed cultures were incubated for 2 days at 28° C., 300 rpm. These were then used to inoculate (0.5 mL into 7 mL) medium 3 (MD6) and cultured for 6 days at 26° C., 300 rpm. Secondary metabolites were extracted from these cultures by the addition of an equal volume of acetonitrile. Cell debris was removed by centrifugation. Samples were then assessed for production of 17-desmethyl rapamycin by LC-MS.

iii) Analysis of 17-desmethylrapamycin

The observed novel rapalogue was proposed to be 17-desmethylrapamycin on the basis of LCMS data. These data showed that the novel rapalogue is 14 mass units smaller than rapamycin, consistent with the absence of a methyl group. Ions observed: [M-H] 898.7, [M+Na]$^+$ 922.7, [M+K]$^+$ 938.6. The UV triene characteristic of rapamycin was observed but the UV maximum of the central peak has shifted ($\lambda$=270 nm c.f. $\lambda$=278 nm for rapamycin).

iv) Fermentation of 17-desmethylrapamycin for isolation

Primary vegetative cultures were prepared by inoculating 0.1 mL of frozen stock into 50 mL medium 4 in a 250 mL flask. The culture was incubated for 48 hours at 28° C. with shaking at 250 rpm. The culture was then subcultured to 400 mL medium 4 in 2000 mL flasks to give the secondary vegetative culture. The culture was incubated for 24 hrs at 28° C., 250 rpm.

Vegetative cultures were inoculated at 7.5% v/v into 15 L of medium 5 (see above) in a 20 L fermentor. Cultivation was carried out for 6 days at 26° C., 0.5 vvm≧30% dissolved oxygen minimum tip speed of 1.18 ms$^{-1}$ maximum tip speed of 2.75 ms$^{-1}$. 48 hours after inoculation 9.5 g of L-lysine was added in 200 mL of water.

v) Extraction and Purification

The fermentation broth (12 L) was stirred with an equal volume of methanol for 2 hours and then centrifuged to pellet the cells (10 min, 3500 rpm). The supernatant was stirred with Diaion® HP20 resin (43 g/L) for 1.5 hours and then filtered. The resin was washed batchwise with acetone (total volume 7.5 L) to strip off the rapalogue and the solvent removed in vacuo. The resulting aqueous concentrate (~800 mL) was diluted to 1 L with water and extracted with EtOAc (3×1 L). The solvent was removed in vacuo to give a sticky brown extract.

The extract was dissolved in acetone (ca 20 mL), coated onto silica, applied to a silica column (3×6.5 cm diameter) and eluted with a stepwise gradient of acetone/hexane (20%-40%). The rapalogue-containing fractions were pooled and the solvent removed in vacuo. The residue was further chromatographed over Sephadex LH20, eluting with 10:10:1 chloroform/heptane/ethanol. The semipurified rapalogue was dissolved in acetonitrile (2.7 mL), centrifuged (10 min, 13200 rpm) and purified by reverse phase (C18) preparative HPLC using a Gilson HPLC, eluting a Phenomenex 21.2×250 mm Luna 5 μm C18 BDS column with 21 mL/min of 60% acetonitrile/water. The most pure fractions (identified by analytical HPLC) were combined and the solvent removed in vacuo to give 17-desmethylrapamycin (133 mg).

vi) Characterisation

The isolated product was subjected to LCMS$^n$ analysis and fragmentation of the sodium adduct gave the predicted ions for 17-desmethylrapamycin based on the identified fragmentation pathway (J. A. Reather, Ph.D. Dissertation, University of Cambridge, 2000). This mass spectrometry fragmentation data narrowed the region of the novel rapalogue where the loss of a methyl occurred to the fragment C16-C27. A range of NMR experiments were performed viz $^1$H, $^{13}$C, APT, COSY, HMQC, HMBC, TOCSY. A thorough and exhaustive review of these data enabled the assignment of 17-desmethylrapamycin. The absence of an olefinic methyl resonance was particularly informative and important correlations were observed and described in Table 5 below.

TABLE 5

$^1$H and $^{13}$C NMR data for 17-desmethylrapamycin

| Position | $^1$H-NMR | | | $^{13}$C-NMR δ | HMBC correlations |
| | δ ppm | Multiplicity, Hz | COSY | ppm | $^1$H to $^{13}$C |
|---|---|---|---|---|---|
| 1 | — | — | | 169.3 | — |
| 2 | 5.23 | br. d, 5 | H-3 | 51.5 | C-1, C-3, C-4, C-6 & C-8 |
| 3 | 2.35 | m, complex | H-2, H-4 | 27.1 | C-1, C-2, C-4 & C-5 |

TABLE 5-continued

¹H and ¹³C NMR data for 17-desmethylrapamycin

| Position | ¹H-NMR δ ppm | Multiplicity, Hz | COSY | ¹³C-NMR δ ppm | HMBC correlations ¹H to ¹³C |
|---|---|---|---|---|---|
| 4 | 1.80 | m, complex | H-3, H-5 | 20.6 | C-2, C-3, C-5, & C-6 |
|  | 1.46 | m, complex |  |  |  |
| 5 | 1.75 | m, complex | H-4, H-6 | 25.2 | C-3, C-4, & C-6 |
|  | 1.45 | m, complex |  |  |  |
| 6 | 2.67 | ddd, 16, 10.5, 5 | H-5 | 44.2 | C-2, C-4, C-5, & C-8 |
|  | 2.58 | ddd, 16, 9.5, 6 |  |  |  |
| 7 | — | — | — | N | — |
| 8 | — | — | — | 166.5 | — |
| 9 | — | — | — | 193.2 | — |
| 10 | — | — | — | 98.6 | — |
| 10-OH | 4.68 | br. s | — | O | C-10 & C-11 |
| 11 | 1.69 | ddq, 11.5, 4, 6.5 | H-11CH₃, H-12 | 33.2 | C-9, C-10, C-12, C-13 & 11-CH₃ |
| 11-CH₃ | 1.02 | d, 6.5 | H-11 | 16.2 | C-10, C-11, & C-12 |
| 12 | 1.42 | m, complex | H-11, H-13 | 26.9 | C-10, C-11, C-13, C-14 & 11-CH₃ |
| 13 | 2.01 | m, complex | H-12, H-14 | 31.1 | C-1, C-3, C-4, C-6 & C-8 |
|  | 1.65 | m, complex |  |  |  |
| 14 | 4.05 | m, complex | H-13, H-15 | 67.0 | C-11, C-12, C-14 & C-15 |
| 15 | 1.15 | ddd, 16, 10.5, 11 | H-14, H-16 | 39.9 | C-13, C-14, C-16, & C-17 |
|  | 1.44 | ddd, 16, 5.5, 6 |  |  |  |
| 16 | 4.00 | ddd, 8, 5.5, 5.5 | H-15, H-17 | 84.4 | C-1, C-3, C-4, C-6 & C-8 |
| 16-OCH₃ | 3.34 | s | — | 55.4 | C-16, C-15 & C-17 |
| 17 | 5.50 | dd, 10.5, 8 | H-16, H-18 | 134.7 | — |
| 18 | 6.21 | dd, 11, 10.5 | H-17, H-19 | 132.2 | C-16, C-17, C-19, C-20 & 17-CH₃ |
| 19 | 6.25 | dd, 14.5, 11 | H-18, H-20 | 133.2 | C-17, C-18, C-20 & C-21 |
| 20 | 6.18 | dd, 14.5, 10.5 | H-19, H-21 | 126.5 | C-18, C-19, C-21 & C-22 |
| 21 | 6.06 | dd, 15, 10.5 | H-20, H-22 | 129.8 | C-19, C-20, C-22 & C-23 |
| 22 | 5.45 | dd, 15, 8 | H-21, H-23 | 140.5 | C-20, C-21, C-23, C-24 & 23-CH₃ |
| 23 | 2.30 | m, complex | H-22, 23-CH₃, H-24 | 35.4 | C-21, C-22, C-24, C-25 & 23-CH₃ |
| 23-CH₃ | 0.96 | d, 6.5 | H-23 | 21.5 | C-22, C-23 & C-24 |
| 24 | 1.45 | m, complex | H-23, H-25 | 40.5 | C-22, C-23, C-25, C-26, 23-CH₃ & 25-CH₃ |
|  | 1.15 | m, complex |  |  |  |
| 25 | 1.89 | ddq, 10.5, 6.5, 4 | H-24, 25-CH₃ | 41.1 | C-23, C-24, C-26, C-27 & 25-CH₃ |
| 25-CH₃ | 0.91 | d, 6.5 | H-25 | 13.7 | C-24, C-25 & C-26 |
| 26 | — | — | — | 214.5 | — |
| 27 | 3.77 | d, 4 | H-28 | 84.9 | C-25, C-26, C-28, C-29 & 27-OCH₃ |
| 27-OCH₃ | 3.28 | s | — | 58.3 | C-27 |
| 28 | 4.18 | d, 4 | H-27 | 75.3 | C-26, C-27, C-29, C-30 & 29-CH₃ |
| 28-OH | 3.54 | br. s | — | O | C-27, C-28 & C-29 |
| 29 | — | — | — | 135.8 | — |
| 29-CH₃ | 1.73 | s | — | 13.2 | C-28, C-29 & C-30 |
| 30 | 5.41 | d, 11 | H-31 | 129.9 | C-28, C-29, C-31, C-32, 29-CH₃ & 31-CH₃ |
| 31 | 3.25 | dq, 11, 6.5 | H-30, 31-CH₃ | 46.4 | C-29, C-30, C-32, C-33 & 31-CH₃ |
| 31-CH₃ | 1.07 | d, 6.5 | H-31 | 15.8 | C-30, C-31 & C-32 |
| 32 | — | — | — | 207.9 | — |
| 33 | 2.74 | dd, 17.5, 5.5 | H-34 | 41.5 | C-31, C-32, C-34 & C-35 |
|  | 2.52 | dd, 17.5, 4 |  |  |  |
| 34 | 5.21 | ddd, 7, 5.5, 4 | H-33, H-35 | 73.9 | C-1, C-32, C-33, C-35, C-36 & 35-CH₃ |
| 35 | 1.60 | m, complex | H-34, 35-CH₃, H-36 | 31.1 | C-33, C-34, C-36, C-37 & 35-CH₃ |
| 35-CH₃ | 0.89 | d, 6.5 | H-35 | 15.7 | C-34, C-35 & C-36 |
| 36 | 1.60 | m, complex | H-35, H-37 | 38.5 | C-34, C-35, C-37, C-38, C-42 & 35-CH₃ |
| 37 | 1.67 | m, complex | H-36, H-38, H-42 | 34.0 | C-35, C-36, C-38, C-39, C-41 & C-42 |

TABLE 5-continued 1H and 13C NMR data for 17-desmethylrapamycin

| Position | 1H-NMR | | | 13C-NMR δ | HMBC correlations |
|---|---|---|---|---|---|
| | δ ppm | Multiplicity, Hz | COSY | ppm | 1H to 13C |
| 38 | 2.11 | ddd, 16.5, 5, 4 | H-37, H-39 | 34.2 | C-36, C-37, C-39, C-40 & C-42 |
| | 1.98 | ddd, 16.5, 10, 13.5 | | | |
| 39 | 2.94 | ddd, 13.5, 12.5, 5 | H-38, H-40 | 84.3 | C-37, C-38, C-40 & C-41 |
| 39-OCH3 | 3.20 | s | — | 55.2 | C-39 |
| 40 | 3.30 | ddd, 14.4, 12.5, 6 | H-39, H-41 | 73.9 | C-38, C-39, C-41 & C-42 |
| 40-OH | 3.57 | br. s | — | 0 | C-39, C-40 & C-41 |
| 41 | 1.60 | m, complex | H-40, H-42 | 31.2 | C-37, C-39, C-37, C-40 & C-42 |
| 42 | 1.78 | m, complex | H-41, H-37 | 31.5 | C-36, C-37, C-38, C-40 & C-41 |
| | 1.58 | m, complex | | | |

NMR data obtained in CDCl3 at 500 MHz for 1H-NMR and 125 for 13C-NMR

Example 5

Isolation of 9-deoxo-17-desmethyl-27-O-desmethyl-39-O-desmethyl rapamycin by complementation of *S. hygroscopicus* MG7-9 with a cassette of auxiliary genes i) Generation of Complementation Plasmid pLL174 Containing the Rapamycin Auxiliary Genes rapK, rapN, rapO, rapM and rapL (rap KN/OML)

Plasmid pSGsetrapKN/OML (WO 04/007709) was digested using SpeI and HindIII and the 5.795 kbp fragment (containing rap KN/OML) was isolated and ligated with conjugative vector pLL150 similarly digested with SpeI and HindIII. After transformation into *E. coli* DH10B, the final plasmid pLL174 was identified and confirmed by restriction enzyme digestion.

ii) Isolation of Strain *S. hygroscopicus* MG7-9 (pLL74)

*E. coli* ET12567, harbouring the plasmid pUZ8002 was transformed with pLL174 to generate the *E. coli* donor strain for conjugation. This was used to transform *S. hygroscopicus* MG7-9 by conjugation. Apramycin resistant colonies were isolated and patched to media 1 plus 50 mg/L apramycin and 25 mg/L nalidixic acid. These patches were grown at 28° C. before secondary patching onto media ISP3 plus 50 mg/L apramycin and grown for 14-21 days at 28° C. A plug from each patch was used to inoculate individual falcon tubes containing 7 mL media 2 (RapV7) plus 50 mg/L apramycin. These seed cultures were incubated for 2 days at 28° C., 300 rpm. These were then used to inoculate (0.5 mL into 7 mL) medium 3 (MD6) and cultured for 6 days at 26° C., 300 rpm.

Secondary metabolites were extracted from these cultures by the addition of an equal volume of acetonitrile. Cell debris was removed by centrifugation. These cultures were assessed for production of 9-deoxo-17-desmethyl-27-O-desmethyl-39-O-desmethyl rapamycin by LCMS.

iii) Analysis of 9-deoxo-17-desmethyl-27-O-desmethyl-39-O-desmethyl rapamycin

The observed novel rapalogue was proposed to be 9-deoxo-17-desmethyl-27-O-desmethyl-39-O-desmethylrapamycin on the basis of LCMS data. These data showed that the novel rapalogue is 42 mass units smaller than 17-desmethylrapamycin, consistent with the absence of 3 methyl groups. Ions observed: [M-H] 856.8, [M+Na]+ 880.7, [M+K]+896.6.

Example 6

Isolation of 9-deoxo-16-O-desmethyl-17-desmethyl-27-O-desmethyl rapamycin by complementation of *S. hygroscopicus* MG7-9 with a cassette of auxiliary genes i) Generation of Complementation Plasmid pLL173 Containing the Rapamycin Auxiliary Genes rapK, rapI, rapN, rapO and rapL (rap KIN/OL)

Plasmid pSGsetrapKIN/OL (WO 04/007709) was digested using SpeI and HindIII and the 5.624 kbp fragment (containing rap KIN/OL) was isolated and ligated with conjugative vector pLL150 similarly digested with SpeI and HindIII. After transformation into *E. coli* DH10B, the final plasmid pLL173 was identified and confirmed by restriction enzyme digestion.

ii) Isolation of Strain *S. hygroscopicus* MG7-9 (pLL173)

*E. coli* ET12567, harbouring the plasmid pUZ8002 was transformed with pLL173 to generate the *E. coli* donor strain for conjugation. This was used to transform *S. hygroscopicus* MG7-9 by conjugation. Apramycin resistant colonies were isolated and patched to media 1 plus 50 mg/L apramycin and 25 mg/L nalidixic acid. These patches were grown at 28° C. before secondary patching onto media ISP3 plus 50 mg/L apramycin and grown for 14-21 days at 28° C. A plug from each patch was used to inoculate individual falcon tubes containing 7 mL media 2 (RapV7) plus 50 mg/L apramycin. These seed cultures were incubated for 2 days at 28° C., 300 rpm. These were then used to inoculate (0.5 mL into 7 mL) medium 3 (MD6) and cultured for 6 days at 26° C., 300 rpm.

Secondary metabolites were extracted from these cultures by the addition of an equal volume of acetonitrile. Cell debris was removed by centrifugation. These cultures were assessed for production of 9-deoxo-16-O-desmethyl-17-desmethyl-27-O-desmethyl rapamycin by LCMS.

iii) Analysis of 9-deoxo-16-O-desmethyl-17-desmethyl-27-O-desmethyl rapamycin

The observed novel rapalogue was proposed to be 9-deoxo-16-O-desmethyl-17-desmethyl-27-O-desmethylrapamycin on the basis of LCMS data. These data showed that the novel rapalogue is 42 mass units smaller than 17-desmethylrapamycin, consistent with the absence of 3 methyl groups. Ions observed: [M-H] 856.8, [M+Na]+ 880.7, [M+K]+896.6.

Example 7

Isolation of 17-desmethyl-39-desmethoxy rapamycin by complementation of S. hygroscopicus MG7-9 with a cassette of auxiliary genes and supplementing the production media with starter acid i) Generation of Complementation Plasmid pLL178 Containing the Rapamycin Auxiliary Genes rapI, rapJ, rapN, rapO, rapM, rapQ and rapL (rap IJN/OMQL)

Plasmid pMG262 (WO 04/007709) (expressing genes rapI, rapJ, rapN, rapO, rapM, rapQ and rapL) was digested using SpeI and HindIII and the 7.259 kbp fragment (containing rap IJN/OMQL) was isolated and ligated with conjugative vector pLL150 similarly digested with SpeI and HindIII. After transformation into E. coli DH10B, the final plasmid pLL178 was identified and confirmed by restriction enzyme digestion.

ii) Isolation of Strain S. hygroscopicus MG7-9 (pLL178)

E. coli ET12567, harbouring the plasmid pUZ8002 was transformed with pLL178 to generate the E. coli donor strain for conjugation. This was used to transform S. hygroscopicus MG7-9 by conjugation. Apramycin resistant colonies were isolated and patched to media 1 plus 50 mg/L apramycin and 25 mg/L nalidixic acid. These patches were grown at 28° C. before secondary patching onto media ISP3 plus 50 mg/L apramycin and grown for 14-21 days at 28° C. A plug from each patch was used to inoculate individual falcon tubes containing 7 mL media 2 (RapV7) plus 50 mg/L apramycin. These seed cultures were incubated for 2 days at 28° C., 300 rpm. These were then used to inoculate (0.5 mL into 7 mL) medium 3 (MD6) and cultured for 6 days at 26° C., 300 rpm. After 24 hours of growth in medium 3, the cultures were fed with cyclohexane carboxylic acid to a final concentration of 1 mM.

Secondary metabolites were extracted from these cultures by the addition of an equal volume of acetonitrile. Cell debris was removed by centrifugation. These cultures were assessed for production of 17-desmethyl-39-desmethoxy rapamycin by LCMS.

iii) Analysis of 17-desmethyl-39-desmethoxyrapamycin

The observed novel rapalogue was proposed to be 17-desmethyl-39-desmethoxyrapamycin on the basis of LCMS data. These data showed that the novel rapalogue is 30 mass units smaller than 17-desmethylrapamycin, consistent with the absence of 1 methoxy group. Ions observed: [M-H] 868.3, [M+Na]+ 892.3, [M+K]+908.3. The UV triene characteristic of rapamycin was observed but the UV maximum of the central peak has shifted ($\lambda$=270 nm c.f. $\lambda$=278 nm for rapamycin).

iv) Fermentation 17-desmethyl-39-desmethoxyrapamycin for isolation

Primary vegetative cultures were prepared by inoculating 0.1 mL of frozen stock into 50 mL medium 4 in a 250 mL flask. The culture was incubated for 48 hours at 28° C. with shaking at 250 rpm. The culture was then subcultured to 400 mL medium 4 in 2000 mL flasks to give the secondary vegetative culture. The culture was incubated for 24 hrs at 28° C., 250 rpm.

Vegetative cultures were inoculated at 7.5% v/v into 15 L of medium 5 (see above) in a 20 L fermentor. Cultivation was carried out for 6 days at 26° C., 0.5 vvm≧30% dissolved oxygen minimum tip speed of 1.18 ms$^{-1}$ maximum tip speed of 2.75 ms$^{-1}$. 48 hours after inoculation 9.5 g of L-lysine was added in 200 mL of water.

v) Extraction and Purification

The fermentation broth (12 L) was stirred with an equal volume of methanol for 2 hours and then centrifuged to pellet the cells (10 min, 3500 rpm). The supernatant was stirred with Diaion® HP20 resin (43 g/L) for 1.5 hours and then filtered. The resin was washed batchwise with acetone (total volume 7.5 L) to strip off the rapalogue and the solvent removed in vacuo. The resulting aqueous concentrate (~800 mL) was diluted to 1 L with water and extracted with EtOAc (3×1 L). The solvent was removed in vacuo to give a sticky brown extract.

The extract was dissolved in acetone (ca 20 mL), coated onto silica, applied to a silica column (3×6.5 cm diameter) and eluted with a stepwise gradient of acetone/hexane (20%-40%). The rapalogue-containing fractions were pooled and the solvent removed in vacuo. The residue was further chromatographed over Sephadex LH20, eluting with 10:10:1 chloroform/heptane/ethanol. The semipurified rapalogue was dissolved in acetonitrile (2.7 mL), centrifuged (10 min, 13200 rpm) and purified by reverse phase (C18) preparative HPLC using a Gilson HPLC, eluting a Phenomenex 21.2×250 mm Luna 5 μm C18 BDS column with 21 mL/min of 60% acetonitrile/water. The most pure fractions (identified by analytical HPLC) were combined and the solvent removed in vacuo to give 17-desmethyl-39-desmethoxyrapamycin (30 mg).

vi) Characterisation

The isolated product was subjected to LCMS$^n$ analysis and fragmentation of the sodium adduct gave the predicted ions for 17-desmethyl-39-desmethoxyrapamycin based on the identified fragmentation pathway (J. A. Reather, Ph.D. Dissertation, University of Cambridge, 2000). This mass spectrometry fragmentation data narrowed the region of the novel rapalogue where the loss of a methyl occurred to the fragment C16-C27 and of a methoxy group to the fragment C28-C44. A range of NMR experiments were performed viz $^1$H, $^{13}$C, APT, COSY, HMQC, HMBC, TOCSY. A thorough and exhaustive review of these data enabled the assignment of 17-desmethyl-39-desmethoxyrapamycin. The absence of an olefinic methyl resonance was particularly informative and the proton NMR assignments are described in Table 6 below.

TABLE 6

$^1$H NMR data for 17-desmethyl-39-desmethoxyrapamycin
1H NMR

| Position | δ ppm | Multiplicity, Hz |
|---|---|---|
| 1 | — | — |
| 2 | 5.20 | br. d, 5 |
| 3 | 2.35 | m, complex |
| 4 | 1.88 | m, complex |
|   | 1.46 | m, complex |
| 5 | 1.70 | m, complex |
|   | 1.55 | m, complex |
| 6 | 2.65 | ddd, 16, 10.5, 5 |
|   | 2.51 | ddd, 16, 9.5, 6 |
| 7 | — | — |
| 8 | — | — |
| 9 | — | — |
| 10 | — | — |
| 10-OH | 4.70 | br. s |
| 11 | 1.59 | ddq, 11.5, 4, 6.5 |

TABLE 6-continued

1H NMR data for 17-desmethyl-39-desmethoxyrapamycin
1H NMR

| Position | δ ppm | Multiplicity, Hz |
|---|---|---|
| 11-CH$_3$ | 1.02 | d, 6.5 |
| 12 | 1.50 | m, complex |
| 13 | 1.97 | m, complex |
|  | 1.67 | m, complex |
| 14 | 4.15 | m, complex |
| 15 | 1.48 | ddd, 16, 10.5, 11 |
|  | 1.11 | ddd, 16, 5.5, 6 |
| 16 | 3.90 | ddd, 8, 5.5, 5.5 |
| 16-OCH$_3$ | 3.29 | s |
| 17 | 5.43 | dd, 10.5, 8 |
| 18 | 6.15 | dd, 11, 10.5 |
| 19 | 6.21 | dd, 14.5, 11 |
| 20 | 6.09 | dd, 14.5, 10.5 |
| 21 | 6.06 | dd, 15, 10.5 |
| 22 | 5.33 | dd, 15, 8 |
| 23 | 2.31 | m, complex |
| 23-CH$_3$ | 0.94 | d, 6.5 |
| 24 | 1.45 | m, complex |
|  | 1.15 | m, complex |
| 25 | 1.99 | ddq, 10.5, 6.5, 4 |
| 25-CH$_3$ | 0.90 | d, 6.5 |
| 26 | — | — |
| 27 | 3.65 | d, 4 |
| 27-OCH$_3$ | 3.19 | s |
| 28 | 4.13 | d, 4 |
| 28-OH | 4.52 | br. s |
| 29 | — | — |
| 29-CH$_3$ | 1.73 | s |
| 30 | 5.40 | d, 11 |
| 31 | 2.74 | dq, 11, 6.5 |
| 31-CH$_3$ | 1.12 | d, 6.5 |
| 32 | — | — |
| 33 | 2.74 | dd, 17.5, 5.5 |
|  | 2.52 | dd, 17.5, 4 |
| 34 | 5.13 | ddd, 7, 5.5, 4 |
| 35 | 1.60 | m, complex |
| 35-CH$_3$ | 0.84 | d, 6.5 |
| 36 | 1.60 | m, complex |
| 37 | 1.67 | m, complex |
| 38 | 2.03-1.11 | m, complex |
| 39 | 2.03-1.11 | m, complex |
| 40 | 3.90 | m, complex |
| 40-OH | 4.28 | br. s |
| 41 | 2.03-1.11 | m, complex |
| 42 | 2.03-1.11 | m, complex |

NMR data in CDCl$_3$ at 400 MHz

Example 8

Isolation of
16-O-desmethyl-17-desmethyl-39-desmethoxy
rapamycin by complementation of *S. hygroscopicus*
MG7-9 with a cassette of auxiliary genes and
supplementing the production media with starter acid i) Generation of Complementation Plasmid pLL184 Containing the Rapamycin Auxiliary Genes, rapI, rapJ, rap N/O, rapQ and rapL (rap IJN/OQL)

Plasmid pMG260 (WO 04/007709) (expressing genes rapI, rapJ, rapN, rapO, rapQ and rapL) was digested using SpeI and HindIII and the 6.3 kbp fragment (containing rap IJN/OQL) was isolated and ligated with conjugative vector pLL150 similarly digested with SpeI and HindIII. After transformation into *E. coli* DH10B, the final plasmid pLL184 was identified and confirmed by restriction enzyme digestion.

ii) Isolation of Strain *S. hygroscopicus* MG7-9 (pLL184)

*E. coli* ET12567, harbouring the plasmid pUZ8002 was transformed with pLL184 to generate the *E. coli* donor strain for conjugation. This was used to transform *S. hygroscopicus* MG7-9 by conjugation. Apramycin resistant colonies were isolated and patched to media 1 plus 50 mg/L apramycin and 25 mg/L nalidixic acid. These patches were grown at 28° C. before secondary patching onto media ISP3 plus 50 mg/L apramycin and grown for 14-21 days at 28° C. A plug from each patch was used to inoculate individual falcon tubes containing 7 mL media 2 (RapV7) plus 50 mg/L apramycin. These seed cultures were incubated for 2 days at 28° C., 300 rpm. These were then used to inoculate (0.5 mL into 7 mL) medium 3 (MD6) and cultured for 6 days at 26° C., 300 rpm. After 24 hours of growth in media 3, the cultures were fed with cyclohexane carboxylic acid to a final concentration of 1 mM.

Secondary metabolites were extracted from these cultures by the addition of an equal volume of acetonitrile. Cell debris was removed by centrifugation. These cultures were assessed for production of 16-O-desmethyl-17-desmethyl-39-desmethoxy rapamycin by LCMS.

iii) Analysis of 16-O-desmethyl-17-desmethyl-39-desmethoxy rapamycin

The observed novel rapalogue was proposed to be 16-O-desmethyl-17-desmethyl-39-desmethoxyrapamycin on the basis of LCMS data. These data showed that the novel rapalogue is 44 mass units smaller than 17-desmethylrapamycin, consistent with the absence of 1 methoxy group and 1 methyl group. Ions observed: [M-H]$^-$ 854.2, [M+Na]$^+$ 878.3, [M+K]$^+$ 894.3.

Example 9

Isolation of
16-O-desmethyl-17-desmethyl-39-desmethoxy
rapamycin by complementation of *S. hygroscopicus*
MG7-9 with a cassette of auxiliary genes and
supplementing the production media with starter acid i) Generation of Complementation Plasmid pLSS249 Containing the Rapamycin Auxiliary Genes rapJ rap N/O, rapQ and rapL (rap JN/OQL)

Plasmid pSGsetrapKIJN/OQL (WO 04/007709) was digested with EcoRI and BglII and the 3.774 kbp fragment was isolated (containing rap JN/OQL) and ligated with similarly digested pSGsetrapJ (WO 04/007709). After transformation into *E. coli* DH10B, plasmid pLSS238 was identified by restriction enzyme digestion. Plasmid pLSS238 was further digested with SpeI and HindIII and the 7.311 kbp fragment isolated (containing rap JN/OQL) and ligated with conjugative vector pLL150 that was similarly digested with SpeI and HindIII. After transformation into *E. coli* DH10B, the final plasmid pLSS249 was identified and confirmed by restriction enzyme digestion.

ii) Isolation of Strain *S. hygroscopicus* MG7-9 (pLSS249)

*E. coli* ET12567, harbouring the plasmid pUZ8002 was transformed with pLSS249 to generate the *E. coli* donor strain for conjugation. This was used to transform *S. hygroscopicus* MG7-9 by conjugation. Apramycin resistant colonies were isolated and patched to media 1 plus 50 mg/L apramycin and 25 mg/L nalidixic acid. These patches were grown at 28° C. before secondary patching onto media ISP3 plus 50 mg/L apramycin and grown for 14-21 days at 28° C. A plug from each patch was used to inoculate individual falcon tubes containing 7 mL media 2 (RapV7) plus 50 mg/L apramycin. These seed cultures were incubated for 2 days at 28° C., 300 rpm. These were then used to inoculate (0.5 mL into 7 mL) medium 3 (MD6) and cultured for 6 days at 26° C., 300 rpm. After 24 hours of growth in media 3, the cultures were fed with cyclohexane carboxylic acid to a final concentration of 1 mM.

Secondary metabolites were extracted from these cultures by the addition of an equal volume of acetonitrile. Cell debris was removed by centrifugation. These cultures were assessed for production of 16-O-desmethyl-17-desmethyl-39-desmethoxy rapamycin by LCMS.

iii) Analysis of 16-O-desmethyl-17-desmethyl-39-desmethoxy rapamycin

LCMS of the novel rapalogue showed it had the same mass and retention time as the rapalogue described in Example 8.

Example 10

Isolation of 9-deoxo-17-desmethyl-27-O-desmethyl-39-desmethoxy-rapamycin by complementation of *S. hygroscopicus* MG7-9 with a cassette of auxiliary genes and supplementing the production media with starter acid i) Generation of Complementation Plasmid pLL191 Containing the Rapamycin Auxiliary Genes rapM, rapN rapO and rapL (rap MN/OL)

Isolation of plasmid pMG237: Plasmid pSGsetrapKJMN/O is a pSET152-derived plasmid in which the genes rapK, rapJ, rapM, rapN and rapO are placed under the actI promoter which is itself controlled by actII-ORF4 which is also present on the plasmid. This is an analogous situation to the other cassette-containing plasmids used in this work. Plasmid pSGsetrapKJMN/O was digested using BglII/XbaI and the isolated vector fragment was ligated with the 1 kb XbaI/BglII fragment of pSGLitrapL$_{his}$. Plasmid pMG237 (expressing rapK, rapJ, rapM, rapN, rapO, and rapL) was isolated.

Plasmid pMG237 (expressing genes rapK, rapJ, rapM, rapN, rapO and rapL) was digested using restriction enzymes SpeI and HindIII and the 6.841 kbp fragment isolated and ligated with conjugative vector pLL150 similarly digested with SpeI and HindIII. After transformation into *E. coli* DH10B, plasmid pLL171 was identified by restriction enzyme digestion. Plasmid pLL171 was digested with AsiSI and NheI and the 5.293 kbp (containing rap MN/OL) was isolated and ligated with pSGsetrapM (WO 04/007709) similarly digested with AsiSI and NheI. After transformation into *E. coli* DH10B, plasmid pLL180 was identified by restriction digestion. Plasmid pLL180 expresses genes rapM, rap N/O and rapL. These were transferred into conjugative vector pLL150 by digestion with SpeI and HindIII. The 4.785 kbp SpeI/HindIII fragment from pLL180 was isolated and ligated with similarly digested pLL150. After transformation into *E. coli* DH10B, the final plasmid pLL191 was identified and confirmed by restriction enzyme digestion.

ii) Isolation of Strain *S. hygroscopicus* MG7-9 (pLL191)

*E. coli* ET12567, harbouring the plasmid pUZ8002 was transformed with pLL191 to generate the *E. coli* donor strain for conjugation. This was used to transform *S. hygroscopicus* MG7-9 by conjugation. Apramycin resistant colonies were isolated and patched to media 1 plus 50 mg/L apramycin and 25 mg/L nalidixic acid. These patches were grown at 28° C. before secondary patching onto media ISP3 plus 50 mg/L apramycin and grown for 14-21 days at 28° C. A plug from each patch was used to inoculate individual falcon tubes containing 7 mL media 2 (RapV7) plus 50 mg/L apramycin. These seed cultures were incubated for 2 days at 28° C., 300 rpm. These were then used to inoculate (0.5 mL into 7 mL) medium 3 (MD6) and cultured for 6 days at 26° C., 300 rpm. After 24 hours of growth in media 3 the cultures were fed with cyclohexane carboxylic acid to a final concentration of 1 mM.

Secondary metabolites were extracted from these cultures by the addition of an equal volume of acetonitrile. Cell debris was removed by centrifugation. These cultures were assessed for production of 9-deoxo-17-desmethyl-27-O-desmethyl-39-desmethoxy-rapamycin by LCMS.

iii) Analysis of 9-deoxo-17-desmethyl-27-O-desmethyl-39-desmethoxy-rapamycin

The observed novel rapalogue was proposed to be 9-deoxo-17-desmethyl-27-O-desmethyl-39-desmethoxyrapamycin on the basis of LCMS data. These data showed that the novel rapalogue is 30 mass units larger than 17-desmethyl-39-deshydroxypre-rapamycin, consistent with the addition of 1 methyl group and 1 hydroxy group. Ions observed: [M-H]$^-$ 840.6, [M+Na]$^+$ 864.6, [M+K]$^+$880.6.

Example 11

Isolation of 9-deoxo-16-O-desmethyl-17-desmethyl-27-O-desmethyl-39-desmethoxy rapamycin by complementation of *S. hygroscopicus* MG7-9 with a cassette of auxiliary genes and supplementing the production media with starter acid i) Generation of Complementation Plasmid pLL190 Containing the Rapamycin Auxiliary Genes rapI, rap N/O and rapL (rap IN/OL)

Plasmid pSGsetKIN/OL was digested with BglII and the 3.272 kbp fragment (containing rap IN/OL) was isolated and ligated with plasmid pSGsetrapI (WO 04/007709) digested with BglII and treated with alkaline phosphatase. After transformation into *E. coli* DH10B plasmid pLL177 was identified by restriction enzyme digestion. Plasmid pLL177 was further digested with using SpeI and HindIII and the 5.624 kbp fragment (containing rap IN/OL) was isolated and ligated with conjugative vector pLL150 similarly digested with SpeI and HindIII. After transformation into *E. coli* DH10B, the final plasmid pLL190 was identified and confirmed by restriction enzyme digestion.

ii) Isolation of Strain *S. hygroscopicus* MG7-9 (pLL190)

*E. coli* ET12567, harbouring the plasmid pUZ8002 was transformed with pLL190 to generate the *E. coli* donor strain for conjugation. This was used to transform *S. hygroscopicus* MG7-9 by conjugation. Apramycin resistant colonies were isolated and patched to media 1 plus 50 mg/L apramycin and 25 mg/L nalidixic acid. These patches were grown at 28° C. before secondary patching onto media ISP3 plus 50 mg/L apramycin and grown for 14-21 days at 28° C. A plug from each patch was used to inoculate individual falcon tubes containing 7 mL media 2 (RapV7) plus 50 mg/L apramycin. These seed cultures were incubated for 2 days at 28° C., 300 rpm. These were then used to inoculate (0.5 mL into 7 mL) medium 3 (MD6) and cultured for 6 days at 26° C., 300 rpm. After 24 hours of growth in media 3, the cultures were fed with cyclohexane carboxylic acid to a final concentration of 1 mM.

Secondary metabolites were extracted from these cultures by the addition of an equal volume of acetonitrile. Cell debris was removed by centrifugation. These cultures were assessed for production of 9-deoxo-16-O-desmethyl-17-desmethyl-27-O-desmethyl-39-desmethoxy rapamycin LCMS.

iii) Analysis of 9-deoxo-16-O-desmethyl-17-desmethyl-27-O-desmethyl-39-desmethoxy rapamycin The observed novel rapalogue was proposed to be 9-deoxo-16-O-desmethyl-17-desmethyl-27-O-desmethyl-39-desmethoxyrapamycin on the basis of LCMS data. These data showed that the novel rapalogue is 16 mass units larger than 17-desmethyl-39-deshydroxypre-rapamycin, consistent with the addition of 1 hydroxy group. Ions observed: [M-H] 826.7, [M+Na]$^+$ 850.6, [M+K]$^+$ 866.6.

Example 12

In Vitro Bioassays for Anticancer Activity

In vitro evaluation of 17-desmethyl-39-desmethoxyrapamycin for anticancer activity in a panel of 12 human tumour cell lines in a monolayer proliferation assay was carried out as described above using a modified propidium iodide assay.

The results are displayed in Table 7 below, each result represents the mean of duplicate experiments. Table 8 shows the IC$_{50}$ and IC$_{70}$ for the test compound and rapamycin across the cell lines tested.

TABLE 7

| | Test/Control (%) at drug concentration | | | | |
|---|---|---|---|---|---|
| | Rapamycin | | 17-desmethyl-39-desmethoxyrapamycin | | |
| Cell line | 1 µM | 10 µM | 1 µM | 10 µM | 100 µM |
| SF268 | 53.5 | 46 | 57 | 37 | 4 |
| 251L | 75.5 | 40 | 85 | 89 | 16 |
| H460 | 67 | 66 | 82 | 76 | 3 |
| MCF7 | 68.5 | 26.5 | 59 | 52 | 8 |
| 394NL | 45 | 44 | 66 | 61 | 4 |
| OVCAR3 | 69 | 69.5 | 84 | 61 | 8 |
| DU145 | 50.5 | 54 | 69 | 66 | 5 |
| LNCAP | 61 | 34 | 59 | 43 | 15 |
| 1138L | 42 | 21.5 | 59 | 46 | 5 |

TABLE 8

| | Rapamycin | 17-desmethyl-39-desmethoxyrapamycin |
|---|---|---|
| Mean IC$_{50}$ (microM) | 3.5 | 13.3 |
| Mean IC$_{70}$ (microM) | 9.1 | 38.2 |

REFERENCES

Alarcon, C. M., Heitman, J., and Cardenas, M. E. (1999) Protein kinase activity and identification of a toxic effector domain of the target of rapamycin TOR proteins in yeast. *Molecular Biology of the Cell* 10: 2531-2546.

Aparicio, J. F., Molnár, I., Schwecke, T., König, A., Haydock, S. F., Khaw, L. E., Staunton, J., and Leadlay, P. F. (1996) Organization of the biosynthetic gene cluster for rapamycin in *Streptomyces hygroscopicus*: analysis of the enzymatic domains in the modular polyketide synthase. *Gene* 169: 9-16.

Baker, H., Sidorowicz, A., Sehgal, S. N., and Vézina, C. (1978) Rapamycin (AY-22,989), a new antifungal antibiotic. III. In vitro and in vivo evaluation. *Journal of Antibiotics* 31: 539-545.

Bierman, M., Logan, R., O'Brien, K., Seno, E. T., Nagaraja Rao, R., and Schoner, B. E. (1992) Plasmid cloning vectors for the conjugal transfer of DNA from *Escherichia coli* to *Streptomyces* spp. *Gene* 116: 43-49.

Bisang, C., Long, P. F., Cortés, J., Westcott, J., Crosby, J., Matharu, A.-L., Cox, R. L., Simpson, T. J., Staunton, J. and Leadlay, P. F. (1999) A chain initiation factor common to both modular and aromatic polyketide synthases. *Nature* 401: 502-505.

Böhm, I., Holzbaur, I. E., Hanefeld, U., Cortés, J., Staunton, J. and Leadlay, P. F. (1998) Engineering of a minimal modular polyketide synthase, and targeted alteration of the stereospecificity of polyketide chain extension. *Chemistry & Biology* 5:407-412.

Box, S. J., Shelley, P. R., Tyler, J. W., Verrall, M. S., Warr, S. R. C., Badger, A. M., Levy, M. A., and Banks, R. M. (1995) 27-O-Demethylrapamycin, an immunosuppressant compound produced by a new strain of *Streptomyces hygroscopicus*. *Journal of Antibiotics* 48: 1347-1349.

Brown, E. J., Albers, M. W., Shin, T. B., Ichikawa, K., Keith, C. T., Lane, W. S., and Schreiber, S. L. (1994) A mammalian protein targeted by G1-arresting rapamycin-receptor complex. *Nature* 369: 756-758.

Brunn, G. J., Williams, J., Sabers, C., Wiederrecht, G., Lawrence, J. C., and Abraham, R. T. (1996) Direct inhibition of the signalling functions of the mammalian target of rapamycin by the phosphoinositide 3-kinase inhibitors, wortmannin and LY294002. *EMBO Journal* 15: 5256-5267.

Carlson, R. P., Hartman, D. A., Tomchek, L. A., Walter, T. L., Lugay, J. R., Calhoun, W., Sehgal, S. N., Chang, J. Y. (1993) Rapamycin, a potential disease-modifying antiarthritic drug. *J. Pharmacol. Exp. Ther.* 266 (2):1125-38.

Chambraud, B., Radanyi, C., Camonis, J. H., Shazand, K., Rajkowski, K., and Baulieu, E. E. (1996) FAP48, a new protein that forms specific complexes with both immunophilins FKBP59 and FKBP12. Prevention by the immunosuppressant drugs FK506 and rapamycin. *Journal of Biological Chemistry* 271: 32923-32929.

Chen, J., Zheng, X. F., Brown, E. J., and Schreiber, S. L. (1995) Identification of an 11-kDa FKBP12-rapamycin-binding domain within the 289-kDa FKBP12-rapamycin-associated protein and characterization of a critical serine residue. *Proceedings of the National Academy of Sciences of the United States of America* 92: 4947-4951.

Choi, J. W., Chen, J., Schreiber, S. L., and Clardy, J. (1996) Structure of the FKBP12-rapamycin complex interacting with the binding domain of human FRAP. *Science* 273: 239-242.

Chung, L., Liu, L., Patel, S., Carney, J. R., and Reeves, C. D. (2001) Deletion of rapQNML from the rapamycin gene cluster of *Streptomyces hygroscopicus* gives production of the 16-O-desmethyl-27-desmethoxy analog. *Journal of Antibiotics* 54: 250-256.

Corey, E. J. and Huang, H., (1989) *Tetrahedron Letters*, 30, 5235-5238.

Cortés, J., Wiesmann, K. E. H., Roberts, G. A., Brown, M. J. B., Staunton, J. and Leadlay, P. F. (1995) Repositioning of a domain in a modular polyketide synthase to promote specific chain cleavage. *Science* 268: 1487-1489.

Del Vecchio, F., Petkovic H., Kendrew, S. G., Low, L., Wilkinson, B., Lill, R. E. Cortés, J., Rudd, B. A. M., Staunton, J. and Leadlay, P. F. (2003) Active-site residue, domain and module swaps in modular polyketide synthases. *Journal of Industrial Microbiology and Biotechnology* 8: 489-494.

Dengler W. A., Schulte J., Berger D. P., Mertelsmann R. and Fiebig H H. (1995) Development of a propidium iodide fluorescence assay for proliferation and cytotoxicity assay. *Anti-Cancer Drugs*, 6:522-532.

DiLella, A. G., and Craig, R. J. (1991) Exon organization of the human FKBP-12 gene: correlation with structural and functional protein domains. *Biochemistry* 30: 8512-8517.

Donadio, S., Staver, M. J., McAlpine, J. B., Swanson, S. J. and Katz, L. (1991) Modular organization of genes required for complex polyketide biosynthesis *Science* 252: 675-679.

Donadio, S., McAlpine, J. B., Sheldon, P. J., Jackson, M. and Katz, L. (1993) An erythromycin analog produced by reprogramming of polyketide synthesis. *Proceedings of the National Academy of Sciences of the United States of America* 90: 7199-7123.

Dudkin, L., Dilling, M. B., Cheshire, P. J., Harwood, F. C., Hollingshead, M., Arbuck, S. G., Travis, R., Sausville, E. A. and Houghton, P. J. (2001). Biochemical correlates of mTOR inhibition by the rapamycin ester CCI-779 and tumor growth inhibition. *Clin. Cancer Res.* 7 (6):1758-64

Dutton, C. J., Gibson, S. P., Goudie, A. C., Holdom, K. S., Pacey, M. S., Ruddock, J. C., Bu'Lock, J. D. and Richards, M. K. (1991) Novel avermectins produced by mutational biosynthesis. Journal of Antibiotics 44: 357-365.

Fehr, T., Sanglier, J-J., Schuler, W., Gschwind, L., Ponelle, M., Schilling, W., Wioland, C. (1996). Antascomicinc A, B, C, D and E: Novel FKBP12 binding compounds from a *Micromonospora* strain. *Journal of Antibiotics* 49 (3): 230-233.

Fiebig H. H., Dengler W. A. and Roth T. (1999) Human tumor xenografts: Predictivity, characterization, and discovery of new anticancer agents. In: Fiebig H H, Burger A M (eds). Relevance of Tumor Models for Anticancer Drug Development. *Contrib. Oncol.*, 54: 29-50.

Ferrari, S., Pearson, R. B., Siegmann, M., Kozma, S. C., and Thomas, G. (1993) The immunosuppressant rapamycin induces inactivation of $P70^{s6k}$ through dephosphorylation of a novel set of sites. *Journal of Biological Chemistry* 268: 16091-16094.

Findlay J. A, and Radics, L. (1980) *Canadian Journal of Chemistry* 58:579.

Fishbein, T. M., Florman, S., Gondolesi, G., Schiano, T., LeLeiko, N., Tschernia, A. and Kaufman, S. (2002). Intestinal transplantation before and after the introduction of sirolimus. *Transplantation* 73 (10):1538-42.

Foey, A., Green, P., Foxwell, B., Feldmann, M. and Brennan, F. (2002). Cytokine-stimulated T cells induce macrophage IL-10 production dependent on phosphatidylinositol 3-kinase and p70S6K: implications for rheumatoid arthritis. Arthritis Res. 4 (1):64-70. Epub 2001 Oct. 10.

Galat, A. (2000) Sequence diversification of the FK506-binding proteins in several different genomes. *European Journal of Biochemistry* 267: 4945-4959.

Graziani, E. I., Ritacco, F. V., Summers, M. Y., Zabriskie, M., Yu, K., Mernan. V. S., Greenstein, M. and Carter, G. T. (2003) Novel sulphur-containing rapamycin analogs prepared by precursor-directed biosynthesis. *Organic Letters* 5: 2385-2388.

Gregory, C. R., Huie, P., Billingham, M. E. and Morris, R. E. (1993) Rapamycin inhibits arterial intimal thickening caused by both alloimmune and mechanical injury. Its effect on cellular, growth factor and cytokine response in injured vessels. *Transplantation* 55 (6):1409-1418.

Gregory, M. A., Till R, and Smith M. C. M. (2003) Integration site for *Streptomyces* phage ΦBT1 and the development of site-specific integrating vectors. *Journal of Bacteriology* 185: 5320-5323.

Gregory, M. A., Gaisser, S., Lill, R. E., Hong, H., Sheridan, R. M., Wilkinson, B., Petkovic, H., Weston, A. J., Carletti, I., Lee, H.-L., Staunton, J. and Leadlay, P. F. (2004) Isolation and characterization of pre-rapamycin, the first macrocyclic intermediate in the biosynthesis of the immunosuppressant rapamycin by *S. hygroscopicus*. *Angewandte Chemie—International Edition* 43: 2551-2553.

Guba, M., von Breitenbuch, P., Steinbauer, M., Koehl, G., Flegel, S., Hornung, M., Bruns, C. J., Zuelke, C., Farkas, S., Anthuber, M., Jauch, K. W., and Geissler, E. K. (2002) Rapamycin inhibits primary and metastatic tumor growth by antiangiogenesis: involvement of vascular endothelial growth factor. *Nature Medicine* 8: 128-135.

Hamilton, G. S., and Steiner, J. P. (1998) Immunophilins: Beyond immunosuppression. *Journal of Medicinal Chemistry* 41: 5119-5143.

Hara, K., Yonezawa, K., Kozlowski, M. T., Sugimoto, T., Andrabi, K., Weng, Q. P., Kasuga, M., Nishimoto, I., and Avruch, J. (1997) Regulation of eIF-4E BP1 phosphorylation by mTOR. *Journal of Biological Chemistry* 272: 26457-26463.

Hardwick, J. S., Kuruvilla, F. G., Tong, J. K., Shamji, A. F., and Schreiber, S. L. (1999) Rapamycin-modulated transcription defines the subset of nutrient-sensitive signalling pathways directly controlled by the Tor proteins. *Proceedings of the National Academy of Sciences of the United States of America* 96: 14866-14870.

Hatanaka, H., Kino, T., Miyata, S., Inamura, N., Kuroda, A., Goto, T., Tanaka, H., Okuhara, M. (1988). FR-900520 and FR-900523, novel immunosuppressants isolated from a *Streptomyces*. II. Fermentation, isolation and physicochemical and biological characteristics. *Journal of Antibiotics* (Tokyo). 41 (11):1592-601.

Hatanaka H, Kino T, Asano M, Goto T, Tanaka H, Okuhara M. (1989). FK506 related compounds produced by *Streptomyces tsukubaensis* No. 9993. *Journal of Antibiotics* (Tokyo). 42 (4):620-2.

Hendrickson, B. A., Zhang, W., Craig, R. J., Jin, Y. J., Bierer, B. E., Burakoff, S., and DiLella, A. G. (1993) Structural organization of the genes encoding human and murine FK506-binding protein (FKBP)13 and comparison to FKBP1. *Gene* 134: 271-275.

Hentges, K. E., Sirry, B., Gingeras, A. C., Sarbassov, D., Sonenberg, N., Sabatini, D., and Peterson, A. S. (2001) FRAP/mTOR is required for proliferation and patterning during embryonic development in the mouse. *Proceedings of the National Academy of Sciences of the United States of America* 98: 13796-13801.

Hung, D. T., and Schreiber, S. L. (1992) cDNA cloning of a human 25 kDa FK506 and rapamycin binding protein. *Biochemical and Biophysical Research Communications* 184: 733-738.

Hung, D. T., Jamison, T. F., and Schreiber, S. L. (1996) Understanding and controlling the cell cycle with natural products. *Chemistry & Biology* 3: 623-639.

Hunziker, D., Yu, T. W., Hutchinson, C. R., Floss, H. G. and Khosla, C. (1998) Primer unit specificity in rifamycin biosynthesis principally resides in the later stages of the biosynthetic pathway. *J. Am. Chem. Soc.* 12: 1092-1093.

Jain, S., Bicknell, G. R., Whiting, P. H. and Nicholson, M. L. (2001). Rapamycin reduces expression of fibrosis-associated genes in an experimental model of renal ischaemia reperfusion injury. Transplant Proc. 33 (1-2):556-8.

Jin, Y. J., Burakoff, S. J., and Bierer, B. E. (1992) Molecular cloning of a 25-kDa high affinity rapamycin binding protein, FKBP25. *Journal of Biological Chemistry* 267: 10942-10945.

Kahan, B. D., Chang, J. Y., and Sehgal, S. N. (1991) Preclinical evaluation of a new potent immunosuppressive agent, rapamycin. *Transplantation* 52: 185-191.

Kahan, B. D., and Camardo, J. S. (2001) Rapamycin: Clinical results and future opportunities. *Transplantation* 72:1181-1193.

Kallen, J. A., Sedrani, R., and Cottens S. (1996) X-ray crystal structure of 28-O-methylrapamycin complexed with FKBP12: Is the cyclohexyl moiety part of the effector domain of rapamycin? *Journal of the American Chemical Society* 118: 5857-5861.

Kao, C. M., Luo, G. L., Katz, L., Cane, D. E. and Khosla, C. (1994) Engineered biosynthesis of a triketide lactone from an incomplete modular polyketide synthase. *Journal of the American Chemical Society* 116: 11612-11613.

Kao, C. M., Luo, G. L., Katz, L., Cane, D. E. and Khosla, C. (1995) Manipulation of macrolide ring size by directed mutagenesis of a modular polyketide synthase. *Journal of the American Chemical Society* 117: 9105-9106.

Kao, C. M., Luo, G. L., Katz, L., Cane, D. E. and Khosla, C. (1996) Engineered biosynthesis of structurally diverse tetraketides by a trimodular polyketide synthase. *Journal of the American Chemical Society* 118: 9184-9185.

Kao, C. M., McPherson, M., McDaniel, R. N., Fu, H., Cane, D. E. and Khosla, C. (1997) Gain of function mutagenesis of the erythromycin polyketide synthase. 2. Engineered biosynthesis of eight-membered ring tetraketide lactone. *Journal of the American Chemical Society* 119: 11339-11340.

Kawasome, H., Papst, P., Webb, S., Keller, G. M., Johnson, G. L., Gelfand, E. W., and Terada, N. (1998) Targeted disruption of p70$^{s6k}$ defines its role in protein synthesis and rapamycin sensitivity. *Proceedings of the National Academy of Sciences of the United States of America* 95: 5033-5038.

Khaw, L. E., Böhm, G. A., Metcalfe, S., Staunton, J., and Leadlay, P. F. (1998) Mutational biosynthesis of novel rapamycins by a strain of *Streptomyces hygroscopicus* NRRL 5491 disrupted in rapL, encoding a putative lysine cyclodeaminase. *Journal of Bacteriology* 180: 809-814.

Kieser, T., Bibb, M. J., Buttner, M. J., Chater, K. F., and Hopwood, D. A. (2000) Practical *Streptomyces* Genetics, John Innes Foundation, Norwich.

Kirby, B., and Griffiths, C. E. M. (2001) Psoriasis: the future. *British Journal of Dermatology* 144:37-43.

Kirchner, G. I., Winkler, M., Mueller L., Vidal, C., Jacobsen, W., Franzke, A., Wagner, S., Blick, S., Manns M. P., and Sewing K.-F. (2000) Pharmacokinetics of SDZ RAD and cyclosporin including their metabolites in seven kidney graft patients after the first dose of SDZ RAD. *British Journal of Clinical Pharmacology* 50:449-454.

König, A., Schwecke, T., Molnár, I., Böhm, G., Lowden, P. A. S., Staunton, J., and Leadlay, P. F. (1997) The pipecolate-incorporating enzyme for the biosynthesis of the immunosuppressant rapamycin. Nucleotide sequence analysis, disruption and heterologous expression of rapP from *Streptomyces hygroscopicus*. *European Journal of Biochemistry* 247: 526-534.

Kuhstoss, S., Huber, M., Turner, J. R., Paschal, J. W. and Rao, R. N. (1996) Production of a novel polyketide through the construction of a hybrid polyketide synthase. *Gene* 183: 231-236.

Kunz, J., Loeschmann, A., Deuter-Reinhard, M., and Hall, M. N. (2000) FAP1, a homologue of human transcription factor NF-X1, competes with rapamycin for binding to FKBP12 in yeast. *Molecular Microbiology* 37: 1480-1493.

Kuo, C. J., Chung, J. K., Fiorentino, D. F., Flanagan, W. M., Blenis, J., and Crabtree, G. R. (1992) Rapamycin selectively inhibits interleukin-2 activation of p70 S6 kinase. *Nature* 358: 70-73.

Lee M H, Pascopella L, Jacobs W R Jr, Hatfull G F. (1991), Site-specific integration of mycobacteriophage L5: integration-proficient vectors for *Mycobacterium smegmatis, Mycobacterium tuberculosis,* and bacille Calmette-Guerin. *Proc Natl Acad Sci USA.;* 88:3111-5.

Liang, J., Choi, J., and Clardy, J. (1999) Refined structure of the FKBP12-rapamycin-FRB ternary complex at 2.2 Å resolution. *Acta Crystallographica Section D-Biological Crystallography* 55: 736-744.

Lomovskaya, N., Fonstein, L., Ruan, X., Stassi, D., Katz, L., and Hutchinson, C. R. (1997) Gene disruption and replacement in the rapamycin-producing *Streptomyces hygroscopicus* strain ATCC 29253. *Microbiology-Uk* 143: 875-883.

Lowden, P. A. S., (1997) Ph.D. Dissertation, University of Cambridge. "Studies on the biosynthesis of rapamycin".

Lowden, P. A. S., B. Wilkinson, et al. (2001). "Origin and true nature of the starter unit for the rapamycin polyketide synthase." Angewandte Chemie-International Edition 40 (4): 777-779.

Lowden, P. A., Bohm, G. A., Metcalfe, S., Staunton, J. and Leadlay, P. F. (2004) New rapamycin derivatives by precursor-directed biosynthesis. *Chem Bio Chem* 5: 535-538.

Luengo, J. I., Yamashita, D. S., Dunnington, D., Beck, A. K., Rozamus, L. W., Yen, H. K., Bossard, M. J., Levy, M. A., Hand, A., Newmantarr, T., Badger, A., Faucette, L., Johnson, R. K., Dalessio, K., Porter, T., Shu, A. Y. L., Heys, R., Choi, J. W., Kongsaeree, P., Clardy, J., and Holt, D. A. (1995) Structure-Activity Studies of Rapamycin Analogs—Evidence That the C-7 Methoxy Group Is Part of the Effector Domain and Positioned at the Fkbp12-Frap Interface. *Chemistry & Biology* 2: 471-481.

Lyons, W. E., George, E. B., Dawson, T. M., Steiner, J. P., and Snyder, S. H. (1994) Immunosuppressant FK506 promotes neurite outgrowth in cultures of PC12 cells and sensory ganglia. *Proceedings of the National Academy of Sciences of the United States of America* 91:3191-3195.

Marshall, J. A., and Shiping, X. (1995) *J. Org. Chem.,* 60, 7230-7237.

Matsuura, M., Noguchi, T., Yamaguchi, D., Aida, T., Asayama, M., Takahashi, H. and Shirai, M. (1996). The sre gene (ORF469) encodes a site-specific recombinase responsible for integration of the $R_4$ phage genome. *J Bact.* 178 (11):3374-3376.

McAlpine, J. B, Swanson S. J., Jackson, M., Whittern, D. N. (1991). Revised NMR assignments for rapamycin. *Journal of Antibiotics* 44: 688-690.

McDaniel, R., Thamchaipenet, A., Gustafsson, C., Fu, H., Betlach, M. and Ashley, G. (1999) Multiple genetic modifications of the erythromycin polyketide synthase to produce a library of novel "unnatural" natural products. *Proceedings of the National Academy of Sciences of the United States of America* 96: 1846-1851.

Molnár, I., Aparicio, J. F., Haydock, S. F., Khaw, L. E., Schwecke, T., König, A., Staunton, J., and Leadlay, P. F. (1996) Organisation of the biosynthetic gene cluster for rapamycin in *Streptomyces hygroscopicus*: analysis of genes flanking the polyketide synthase. *Gene* 169: 1-7.

Morice, M. C., Serruys, P. W., Sousa, J. E., Fajadet, J., Ban Hayashi, E., Perin, M., Colombo, A., Schuler, G., Barragan, P., Guagliumi, G., Molnar, F. and Falotico, R.

(2002). RAVEL Study Group. Randomized Study with the Sirolimus-Coated Bx Velocity Balloon-Expandable Stent in the Treatment of Patients with de Novo Native Coronary Artery Lesions. A randomized comparison of a sirolimus-eluting stent with a standard stent for coronary revascularization. *N. Eng. I J. Med.* 346 (23):1773-80.

Myckatyn, T. M., Ellis, R. A., Grand, A. G., Sen, S. K., Lowe, J. B. 3rd, Hunter, D. A. and Mackinnon, S. E. (2002). The effects of rapamycin in murine peripheral nerve isografts and allografts. *Plast. Reconstr. Surg.* 109 (7):2405-17.

Navé, B. T., Ouwens, D. M., Withers, D. J., Alessi, D. R., and Sheperd, P. R. (1999) Mammalian target of rapamycin is a direct target for protein kinase B: identification of a convergence point for opposing effects of insulin and amino-acid deficiency on protein translation. *Biochemical Journal* 344:427-431.

NCCLS Reference Method for Broth Dilution Antifungal Susceptibility Testing for Yeasts: Approved Standard M27-A, vol. 17 No. 9. (1997).

Nishida, H., Sakakibara, T., Aoki, F., Saito, T., Ichikawa, K., Inagaki, T., Kojima, Y., Yamauchi, Y., Huang, L. H., Guadliana, M. A., Kaneko, T., and Kojima, N. (1995) Generation of novel rapamycin structures by microbial manipulations. *Journal of Antibiotics* 48: 657-666.

Oliynyk, M., Brown, M. J. B., Cortés, J., Staunton, J. and Leadlay, P. F. (1996) A hybrid modular polyketide synthase obtained by domain swapping. *Chemistry & Biology* 3: 833-839.

Paget, M. S. B., Chamberlin, L., Atrih, A., Foster, S. J., and Buttner, M. J. (1999) Evidence that the extracytoplasmic function sigma factor $\sigma^E$ is required for normal cell wall structure in *Streptomyces coelicolor* A3 (2). *Journal of Bacteriology* 181: 204-211)

Paiva, N. L., Demain, A. L., and Roberts, M. F. (1991) Incorporation of acetate, propionate, and methionine into rapamycin By *Streptomyces hygroscopicus*. *Journal of Natural Products* 54: 167-177.

Paiva, N. L., Demain, A. L., and Roberts, M. F. (1993) The immediate precursor of the nitrogen-containing ring of rapamycin is free pipecolic acid. *Enzyme and Microbial Technology* 15: 581-585.

Patterson, C. E., Schaub, T., Coleman, E. J., and Davies E. C. (2000) Developmental regulation of FKBP65. An ER-localized extracellular matrix binding-protein. *Molecular Biology of the Cell* 11:3925-3935.

Perin, E C, (2005), "Choosing a Drug-Eluting Stent: A Comparison Between CYPHER and TAXUS", *Reviews in Cardiovascular Medicine*, 6 (suppl 1), ppS13-S21.

Powell, N., Till, S., Bungre, J., Corrigan, C. (2001). The immunomodulatory drugs cyclosporin A, mycophenolate mofetil, and sirolimus (rapamycin) inhibit allergen-induced proliferation and IL-5 production by PBMCs from atopic asthmatic patients. *J. Allergy Clin. Immunol.* 108 (6):915-7.

Rabinovitch, A., Suarez-Pinzon, W. L., Shapiro, A. M., Rajotte, R. V. and Power, R. (2002). Combination therapy with sirolimus and interleukin-2 prevents spontaneous and recurrent autoimmune diabetes in NOD mice. *Diabetes* 51 (3):638-45.

Raught, B., Gingras, A. C., and Sonenberg, N. (2001) The target of rapamycin (TOR) proteins. *Proceedings of the National Academy of Sciences of the United States of America* 98: 7037-7044.

J. A. Reather, Ph.D. Dissertation, University of Cambridge, 2000

Reeves, C. D., Murli, S., Ashley, G. W., Piagentini, M., Hutchinson, C. R. and McDaniel, R. (2001) Alteration of the substrate specificity of a modular polyketide synthase acyltransferase domain through site-specific mutations. *Biochemistry* 40: 15464-15470.

Reid, R., Piagentini, M., Rodriguez, E., Ashley, G., Viswanathan, N., Carney, J., Santi, D. V., Hutchinson, C. R. and McDaniel, R. (2003) A model of structure and catalysis for ketoreductase domains in modular polyketide synthases. *Biochemistry* 42: 72-29.

Reitamo, S., Spuls, P., Sassolas, B., Lahfa, M., Claudy, A. and Griffiths, C. E.; Sirolimus European Psoriasis Study Group. (2001). Efficacy of sirolimus (rapamycin) administered concomitantly with a subtherapeutic dose of cyclosporin in the treatment of severe psoriasis: a randomized controlled trial. *Br. J. Dermatol.* 145 (3):438-45.

Rosen, M. K. and Schreiber, S. L. (1992) Natural products as probes of cellular function: studies of immunophilins. *Angewandte Chemie-International Edition in English* 31: 384-400.

Roth T., Burger A. M., Dengler W., Willmann H. and Fiebig H. H. (1999) Human tumor cell lines demonstrating the characteristics of patient tumors as useful models for anti-cancer drug screening. In: Fiebig H H, Burger A M (eds). Relevance of Tumor Models for Anticancer Drug Development. *Contrib. Oncol.*, 54: 145-156.

Rowe, C. J., Cortés, J., Gaisser, S., Staunton, J. and Leadlay, P. F: (1998) Construction of new vectors for high-level expression in actinomycetes. *Gene* 216, 215-223.

Rowe, C. J., Böhm, I. U., Thomas, I. P., Wilkinson, B., Rudd, B. A. M., Foster, G., Blackaby, A. P., Sidebottom, P. J., Roddis, Y., Buss, A. D., Staunton, J. and Leadlay, P. F. (2001) Engineering a polyketide with a longer chain by insertion of an extra module into the erythromycin-producing polyketide synthase. *Chemistry & Biology* 8: 475-485.

Roymans, D., and Slegers, H. (2001) Phosphatidylinositol 3-kinases in tumor progression. *European Journal of Biochemistry* 268:487-498.

Ruan, X., Pereda, A., Stassi, D. L., Zeidner, D., Summers, R. G., Jackson, M., Shivakumar, A., Kakavas, S., Staver, M. J., Donadio, S, and Katz, L. (1997) Acyltransferase domain substitutions in erythromycin polyketide synthase yield novel erythromycin derivatives. *Journal of Bacteriology* 179:6416-6425.

Salituro, G. M., Zink, D. L., Dahl, A., Nielsen, J., Wu, E., Huang, L., Kastner C. and Dumont, F. (1995) Meridamycin: a novel nonimmunosuppressive FKBP12 ligand from *Streptomyces hygroscopicus*. *Tetrahydron letters* 36: 997-1000.

Sambrook, J., Fritsch, E. F., and Maniatis, T. (1989) Molecular cloning: a laboratory manual, 2nd ed. Cold Spring Harbor Laboratory Press, N. Y.

Schreiber, S. L., and Crabtree, G. R. (1992) The mechanism of action of cyclosporine A and FK506. *Immunology Today* 13: 136-142.

Schwecke, T., Aparicio, J. F., Molnár, I., König, A., Khaw, L. E., Haydock, S. F., Oliynyk, M., Caffrey, P., Cortés, J., Lester, J. B., Böhm, G. A., Staunton, J., and Leadlay, P. F. (1995) The biosynthetic gene cluster for the polyketide immunosuppressant rapamycin. *Proceedings of the National Academy of Sciences of the United States of America* 92: 7839-7843.

Sedrani, R., Cottens, S., Kallen, J., and Schuler, W. (1998) Chemical modifications of rapamycin: the discovery of SDZ RAD. *Transplantation Proceedings* 30: 2192-2194.

Sehgal, S. N., Baker, H., and Vézina, C. (1975) Rapamycin (AY-22,989), a new antifungal antibiotic II. Fermentation, isolation and characterization. *Journal of Antibiotics* 28: 727-733.

Shepherd, P. R, Withers, D. J., and Siddle K. (1998) Phosphoinositide 3-kinase: the key switch mechanism in insulin signalling. *Biochemical Journal* 333: 471-490.

Smovkina, T., Mazodier, P., Boccard, F., Thompson, C. J. and Guerineau, M. (1990) Construction of a series of pSAM2-based integrative vectors for use in actinomycetes. *Gene* 94: 53-59.

Stassi, D. L., Kakavas, S. J., Reynolds, K. A., Gunawardana, G., Swanson, S., Zeidner, D., Jackson, M., Liu, H., Buko, A. and Katz, L. (1998) Ethyl-substituted erythromycin derivatives produced by directed metabolic engineering *Proceedings of the National Academy of Sciences of the United States of America* 95: 7305-7309.

Steiner, J. P., Hamilton, G. S., Ross, D. T., Valentine, H. L., Guo, H., Connolly, M. A., Liang, S., Ramsey, C., Li, J.-H. J., Huang, W., Howorth, P., Soni, R., Fuller, M., Sauer, H., Nowotnik, A. C., and Suzdak, P. D. (1997) Neutrophic immunophilin ligands stimulate structural and functional recovery in neurodegenerative animal models. *Proceedings of the National Academy of Sciences of the United States of America* 94:2019-2024.

Stella V. J. et al (1985) "Prodrugs: A Chemical Approach to Targeted Drug Delivery" *Directed Drug Delivery* R. Borchardt et al (ed.) pages 247-267 (Humana Press)

Tang, S. J., Reis, G., Kang, H., Gingras, A.-C., Sonenberg, N., and Schuman, E. M. (2002) A rapamycin-sensitive signalling pathway contributes to long-term synaptic plasticity in the hippocampus. *Proceedings of the National Academy of Sciences of the United States of America* 1:467-472.

Van Duyne, G. D., Standaert, R. F., Karplus, P. A., Schreiber, S. L., and Clardy, J. (1993) Atomic structures of the human immunophilin FKBP-12 complexes with FK506 and rapamycin. *Journal of Molecular Biology* 229: 105-124.

Van Mellaert, L., Mei, L., Lammertyn, E., Schacht, S., and Anné, J. (1998) Site-specific integration of bacteriophage VWB genome into *Streptomyces venezuelae* and construction of a VWB-based integrative vector. *Microbiology* 144: 3351-3358.

Vézina, C., Kudelski, A., and Sehgal, S. N. (1975) Rapamycin (AY-22,989), a new antifungal antibiotic. I. Taxonomy of the producing streptomycete and isolation of the active principle. *Journal of Antibiotics* 28: 721-726.

Vilella-Bach, M., Nuzzi, P., Fang, Y. M., and Chen, J. (1999) The FKBP12-rapamycin-binding domain is required for FKBP12-rapamycin-associated protein kinase activity and $G_1$ progression. *Journal of Biological Chemistry* 274: 4266-4272.

Waller, J. R., and Nicholson, M. L. (2001) Molecular mechanisms of renal allograft fibrosis. *British Journal of Surgery* 88:1429-1441.

Warner, L. M., Adams, L. M., Chang, J. Y. and Sehgal, S. N. (1992) A modification of the in vivo mixed lymphocyte reaction and rapamycin's effect in this model. *Clin. Immunol. Immunopathol.* 64 (3):242-7.

Wilman D. E. V. (1986) "Prodrugs in Cancer Chemotherapy" *Biochemical Society Transactions* 14, 375-382 (615th Meeting, Belfast)

Wong, G. K., Griffith, S., Kojima, I., and Demain, A. L. (1998) Antifungal activities of rapamycin and its derivatives, prolylrapamycin, 32-desmethylrapamycin, and 32-desmethoxyrapamycin. *Journal of Antibiotics* 51: 487-491.

Wu, K., Chung, L., Revill, W. P., Katz, L., and Reeves, C. D. (2000) The FK520 gene cluster of *Streptomyces hygroscopicus* var. *ascomyceticus* (ATCC 14891) contains genes for biosynthesis of unusual polyketide extender units. *Gene* 251: 81-90.

Yem, A. W., Tomasselli, A. G., Heinrikson, R. L., Zurcher-Neely, H., Ruff, V. A., Johnson, R. A., and Deibel, M. R. (1992) The Hsp56 component of steroid receptor complexes binds to immobilized FK506 and shows homology to FKBP-12 and FKBP-13. *Journal of Biological Chemistry* 267: 2868-2871.

Yin, J., Zarkowsky, D. S., Thomas, D. W., Zhao, M. M., and Huffman, M. A. (2004) *Org. Lett.* 6; 1465-1468

Yu, K., Toral-Barza, L., Discafani, C., Zhang, W. G., Skotnicki, J., Frost, P., Gibbons, J. J. (2001) mTOR, a novel target in breast cancer: the effect of CCI-779, an mTOR inhibitor, in preclinical models of breast cancer. *Endocrine-Related Cancer* 8:249-258.

Zhu, J., Wu J., Frizell, E., Liu, S. L., Bashey, R., Rubin, R., Norton, P. and Zern, M. A. (1999). Rapamycin inhibits hepatic stellate cell proliferation in vitro and limits fibrogenesis in an in vivo model of liver fibrosis. *Gastroenterology.* 117 (5):1198-204.

The invention claimed is:

1. A compound having the following formula:

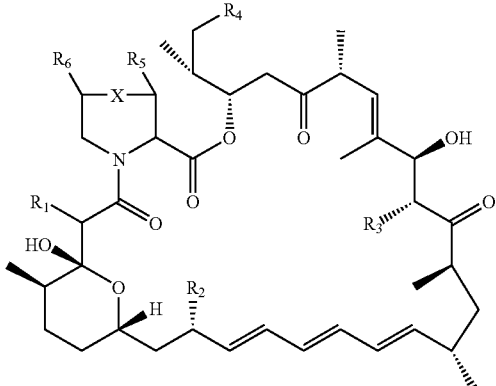

wherein:

x represents a direct bond, —CH$_2$—, —S—CH$_2$—, —CH$_2$—S— or —S(=O)—CH$_2$—;

or —CHR$_5$-x-CHR$_6$— represents

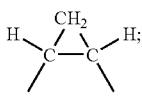

R$_1$ represents =O or (H,H);
R$_2$ represents OH or OMe;
R$_3$ represents H, OH or OMe;
R$_4$ represents a structural fragment selected from groups A, B, C, D, E and F,

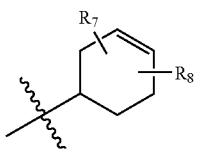
A

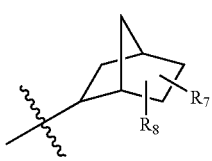
B

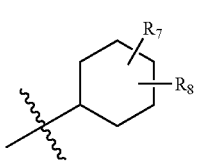
C

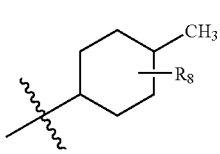
D

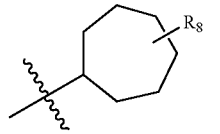
E

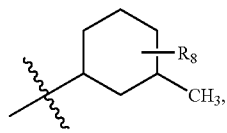
F in which
the wavy line indicates the position of attachment of the fragment,
R$_7$ represents H or OH and
R$_8$ represents H, OH, halo, thiol or C$_{1-4}$ alkyl;
or R$_4$ alternatively represents a 5- to 7-membered heterocycle containing one or more heteroatoms selected from the group consisting of O, S and N, which heterocycle is optionally substituted with one or more substituents selected from C$_{1-4}$ alkyl, OH, F and Cl; and
R$_5$ and R$_6$ are each independently H or OH,
or pharmaceutically acceptable salts thereof.

2. A compound according to claim 1, wherein R$_4$ represents a structural fragment selected from the groups A, B, C, E and F, as defined in claim 2, in which R$_7$ represents H or OH and R$_8$ represents H, OH, Cl or F.

3. A compound according to claim 2, wherein R$_4$ represents a structural fragment selected from the groups A(i), C(i), E(i) and F(i):

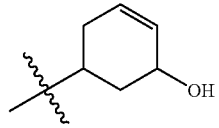
A(i)

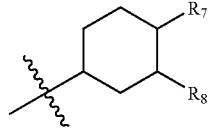
C(i)

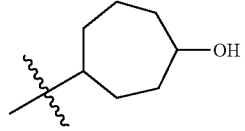
E(i)

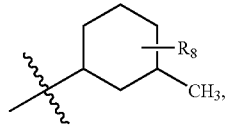
F(i)

wherein R$_7$ represents H or OH and R$_8$ represents H, or OH.

4. A compound according to claim 1, wherein when R$_5$ represents OH, R$_6$ represents H and when R$_6$ represents OH R$_5$ represents H.

5. A compound according to claim 1, wherein x represents a direct bond or CH$_2$.

6. A compound according to claim 1, wherein x represents $CH_2$.

7. A compound according to claim 1, wherein $R_2$ represents OH.

8. A compound according to claim 1 wherein $R_1$ represents (H, H), $R_2$ represents OH, $R_3$ represents H, $R_4$ represents the structural fragment C(i), as defined in claim 4, except that $R_7$ represents OH and $R_8$ represents H, and x represents $CH_2$.

9. A compound according to claim 1 wherein $R_1$ represents (H, H) or =O, $R_2$ represents OH or OMe, $R_3$ represents OH or OMe, $R_4$ represents the structural fragment C(i), as defined in claim 4, except that $R_7$ represents OH and $R_8$ represents H, or OH, and x represents $CH_2$.

10. A compound according to claim 1 wherein $R_1$ represents =O, $R_2$ represents OH or OMe, $R_3$ represents H, OH or OMe, $R_4$ represents the structural fragment C(i), as defined in claim 4, except that $R_7$ represents OH and $R_8$ represents F or Cl, and x represents $CH_2$.

11. A compound according to claim 1 wherein $R_1$ represents =O, $R_2$ represents OH, $R_3$ represents OMe, $R_4$ represents the structural fragment C(i), as defined in claim 4, except that $R_7$ represents OH and $R_8$ represents H, and x represents $CH_2$.

12. A compound according to claim 1 wherein $R_1$ represents =O, $R_2$ represents OH, $R_3$ represents OH, $R_4$ represents the structural fragment C(i), as defined in claim 4, except that $R_7$ represents OH and $R_8$ represents H, and x represents $CH_2$.

13. A compound having the following formula:

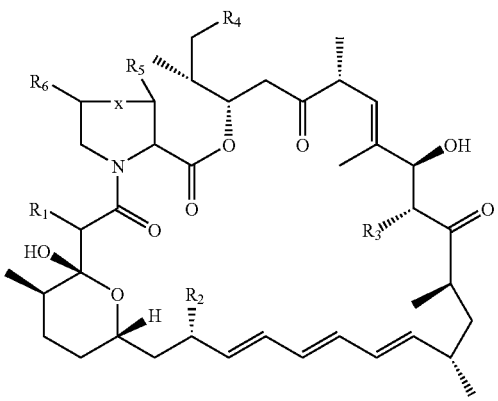

wherein $R_1$ represents =O, $R_2$ represents OH, $R_3$ represents OMe, $R_4$ represents the structural fragment C(i), as defined in claim 4, except that $R_7$ represents OH and $R_8$ represents OMe, and x represents $CH_2$.

14. A pharmaceutical composition comprising a compound according to any one of claims 1-7 and 8-13 or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 7,803,808 B2  
APPLICATION NO. : 11/659936  
DATED : September 28, 2010  
INVENTOR(S) : Matthew Alan Gregory et al.

It is certified that error appears in the above-identified patent and that said Letters Patent is hereby corrected as shown below:

On the title page item (73),

Change Assignee from Wyeth LLC, Madison, NJ (US)

to Biotica Technology Limited, Essex, (UK)

Signed and Sealed this  
Twelfth Day of July, 2011

David J. Kappos  
*Director of the United States Patent and Trademark Office*

SEQUENCE LISTING

```
<160> NUMBER OF SEQ ID NOS: 18

<210> SEQ ID NO 1
<211> LENGTH: 5
<212> TYPE: PRT
<213> ORGANISM: Artificial
<220> FEATURE:
<223> OTHER INFORMATION: Artificially generated restriction site

<400> SEQUENCE: 1

Phe Pro Gly Gln Gly
1               5

<210> SEQ ID NO 2
<211> LENGTH: 15
<212> TYPE: DNA
<213> ORGANISM: Artificial
<220> FEATURE:
<223> OTHER INFORMATION: Artificially generated restriction site
```

-continued

<400> SEQUENCE: 2
tttcccgggc aggga                                                      15

<210> SEQ ID NO 3
<211> LENGTH: 5
<212> TYPE: PRT
<213> ORGANISM: Artificial
<220> FEATURE:
<223> OTHER INFORMATION: Artificially generated restriction site

<400> SEQUENCE: 3

Phe Pro Gly Gln Gly
1               5

<210> SEQ ID NO 4
<211> LENGTH: 15
<212> TYPE: DNA
<213> ORGANISM: Artificial
<220> FEATURE:
<223> OTHER INFORMATION: Artificially generated restriction site

<400> SEQUENCE: 4
ttcccgggtc agggg                                                      15

<210> SEQ ID NO 5
<211> LENGTH: 5
<212> TYPE: PRT
<213> ORGANISM: Artificial
<220> FEATURE:
<223> OTHER INFORMATION: Artificially generated restriction site

<400> SEQUENCE: 5

Phe Pro Gly Gln Gly
1               5

<210> SEQ ID NO 6
<211> LENGTH: 15
<212> TYPE: DNA
<213> ORGANISM: Artificial
<220> FEATURE:
<223> OTHER INFORMATION: Artificially generated restriction site

<400> SEQUENCE: 6
tttcctggcc agggg                                                      15

<210> SEQ ID NO 7
<211> LENGTH: 5
<212> TYPE: PRT
<213> ORGANISM: Artificial
<220> FEATURE:
<223> OTHER INFORMATION: Artificially generated restriction site

<400> SEQUENCE: 7

Ala Val Leu Gly Asp
1               5

<210> SEQ ID NO 8
<211> LENGTH: 15
<212> TYPE: DNA
<213> ORGANISM: artificial
<220> FEATURE:
<223> OTHER INFORMATION: Artificially generated restriction site

<400> SEQUENCE: 8
gcggtgctgg gtgat                                                      15

```
<210> SEQ ID NO 9
<211> LENGTH: 5
<212> TYPE: PRT
<213> ORGANISM: Artificial
<220> FEATURE:
<223> OTHER INFORMATION: Artificially generated restriction site

<400> SEQUENCE: 9

Ala Val Leu Gly Asp
1               5

<210> SEQ ID NO 10
<211> LENGTH: 15
<212> TYPE: DNA
<213> ORGANISM: Artificial
<220> FEATURE:
<223> OTHER INFORMATION: Artificially generated restriction site

<400> SEQUENCE: 10
gcggtgctgg gtgat                                                   15

<210> SEQ ID NO 11
<211> LENGTH: 5
<212> TYPE: PRT
<213> ORGANISM: Artificial
<220> FEATURE:
<223> OTHER INFORMATION: Artificially generated restriction site

<400> SEQUENCE: 11

Ala Val Leu Gly Asp
1               5

<210> SEQ ID NO 12
<211> LENGTH: 15
<212> TYPE: DNA
<213> ORGANISM: Artificial
<220> FEATURE:
<223> OTHER INFORMATION: Artificially generated restriction site

<400> SEQUENCE: 12
gcggtcctag gtgat                                                   15

<210> SEQ ID NO 13
<211> LENGTH: 26
<212> TYPE: DNA
<213> ORGANISM: Artificial
<220> FEATURE:
<223> OTHER INFORMATION: Primer

<400> SEQUENCE: 13
gtcctaggtg atgtcccggc aacacg                                       26

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
cacctgcagg cccaactcgg ccagctcgct                                   30

<210> SEQ ID NO 15
<211> LENGTH: 1596
<212> TYPE: DNA
```

<213> ORGANISM: Artificial
<220> FEATURE:
<223> OTHER INFORMATION: Left region of homology PCR product from AT10, amplified from S. hygroscopicus using SEQ ID NOs 1 and 2, which contain additional restriction sites.

<400> SEQUENCE: 15

```
cacctgcagg cccaactcgg ccagctcgct gatcagcgcc tcgtccgggg cgctgcggga      60
cagcaacagc agatgacgca caccgcgttc ggccaccagg tgccgggcgg cgatccccgc     120
cagcacaccc gaaccaccgg tgatcagaac cgtgccatcc ggatcccaga cgccttcagg     180
ctcaggctca gcgacgcccg tacgagtcag tcgcggtgcc tcgtaccggc cgtcgatgac     240
ccgcagccgc ggctcatcga gcccgacggt ggcggccagt tggtccgggg tgagggtgtc     300
gtcgtcactt tccaccagga cgaaccggcc cgggtgctcc gactgagccg aacgcatcaa     360
ccccgacacc gcggctgcgg ccaaaccagt tccggtccgc acaaccagcg tactgtcagt     420
gaaacgctcc cccgccagcc acacctgcac cgcctgcaga acctcagcgg tcagccgacg     480
agtctgtgcc agcgggtcac cgctgtcggg gagtgcggtg aacacaacga catcgggcat     540
cggcacctcg ccgtccgcga ggtcttcaaa cttgcccacc gtcacgccga cctgctggga     600
gaccgggatc tccgtccacg tcagggcgaa cagatcatcg acagcagaac cgagcgcatc     660
ggctgccacc ggacgggtca ccagcgagcc gatggtggcc accggccgac cgatgtcatc     720
agcgacccgc acacccagc catccgcgac ccgtgtcatc gcgacccgca cgtggccga     780
gccagtgaca tggacctgga cgtggttcca ggagaacggc aaccgcacgg tgtcgcggtc     840
ggcatcgggt gtgttcagga tcccggcgtg cagggcggca tccaacaccg cagggtggac     900
ggcgaatcgt gccgcgtcct gggtctgctc ctcagccaga gcaacctcgg cgaagacggt     960
gtcaccatca cgccacgcgg cctgcaaacc ctggaaggca ggtccgtact cgtaacccgc    1020
cctggtcagc tggtcgtaga agcctgccac gtccaccggc ttggcctgcg caggtggcca    1080
cgcggtgagg tccgacgttg gcacagtcgt gtcggacacg ctgacggtgg cggaaacgtg    1140
ccggacccag gcatcggcgc tgtccgcccg ggagaagacc gtcaccgcgc ggtgtccgga    1200
ctcgtcggcc tcgccgacgg atacggacag ttgcacaccg ccggtctgcg gcagcagaag    1260
cggggcttcg acgatcagct cgtcaacgac gtcgcagccc acctcatcag ccgcgcggac    1320
aaccagctcc acaaacccgg taccgggcag caggacactg ccccggaccg cgtgatcagc    1380
cagccacgcg tgggtggcca gtgataccc cccggtcagc atcacaccat ccgaacccgg    1440
catcgccagc accgcaccca gcaacggatg gcccaccgca tccagacccg cccccgacac    1500
atcggcagac cggccggcct cagcccaata ccgctggtgc tggaacgcgt acgtcggaag    1560
atccagcacc cgtgttgccg ggacatcacc taggac                             1596
```

<210> SEQ ID NO 16
<211> LENGTH: 28
<212> TYPE: DNA
<213> ORGANISM: Artificial
<220> FEATURE:
<223> OTHER INFORMATION: Primer

<400> SEQUENCE: 16

```
cctggccagg aaagacgaac acgatcct                                         28
```

<210> SEQ ID NO 17
<211> LENGTH: 29
<212> TYPE: DNA
<213> ORGANISM: Artificial

```
<220> FEATURE:
<223> OTHER INFORMATION: Primer

<400> SEQUENCE: 17
cgaagcttga gccgctggcg atcgtggga                                              29

<210> SEQ ID NO 18
<211> LENGTH: 1550
<212> TYPE: DNA
<213> ORGANISM: Artificial
<220> FEATURE:
<223> OTHER INFORMATION: Right region of homology PCR product from AT10,
      amplified from S. hygroscopicus using SEQ ID NOs 1 and 2, which
      contain additional restriction sites.

<400> SEQUENCE: 18
cctgccagga aagacgaaca cgatcctggg gtcggacacc gcggtgccgg tgacggtctc          60
atctccaagg agtacggcgc ggtgctcgaa caccgaccgt gtcaccgcca gcgtcgatgc         120
cacagcccgt atatccactc cgggcgacgc cgccaggtag gcgcggagcc ggtcttcgtg         180
ttcggtcagg gcgggctggg tcttggccga tatcaccagc ggcaccagtt ccgaaaccag         240
tacgggtgta gagccagccg tgtcgcccac agactgtgcc ggtgcactct caaggatgac         300
gtgggcgtta gtgccactga tcccgaacga cgacacacct gcccgacggg gtcggccggt         360
ctccggccac ggctggttct ccgccaccag ctcgaccgca cccgccgacc agtccacatg         420
ccgcgacggc tcatccacat gcaacgtgcg cggcaccatg ctgtgctgca gggccatcac         480
catcttgatg acacccgaca cacctgcggc agcctgggta tggccgacgt tcgacttcag         540
cgatcccagc agcagcggct ccccgcgcc ctggccgtaa gtagcgatca ccgcctgggc          600
ctcgatcggg tcacccagcg tcgtacccgt gccgtgcgcc tcgaccacat ccacctcgtg         660
cggcgccagg ccggcgttgc tgagagcggc ccggatcacc cgctgctgcg aaggaccgtt         720
cggcgcggac aggccgttcg acgcaccgtc ctggttcacc gccgagctac ggaccaccgc         780
caatatctgg tgaccgttgg cctgagcatc cgacaaacgc tccaccaata ggacgccgac         840
gccctcagcc cacccgtgc cgtccgcggc gtcagcgaac gccttgcacc ggccatcggc          900
tgacaagcct cgctgccgcg agaactccac gaaagtctgc ggcgtggcca tcacggtcac         960
gccgccgacc agggccagcg aacactcacc ctgtcgcagg gcataccccg cctgatgcaa        1020
cgccaccagc gacgacgaac acgccgtgtc caccgtgaac gcgggacctt cgagaccgaa        1080
gaagtacgac accggcccg acaacacact cgccgcacca gcagttgtcc cgaagccgcc         1140
gaggtcggca ccgatgccgt agccaccggg gtaagcacct atgaagacgc cggtgtcgct        1200
gccgcgtacg gaaccgggct cgatcccggc ccgctcgaac gcctcccagg acacctcaag        1260
catcaaccgc tgctgcggat ccatcgccaa cgcctcacgc ggactgatcc cgaagaacga        1320
ggcgtcgaaa ccgccgcgg catccaggaa gccgccctgc acgctgtagg acttcccggg         1380
cgcgtccggg tccggatcgt acaggttctc gacgtccag ccgcggtcgg ttgggaagcc         1440
ggaaatcgcg tccgtaccgg actcgaccaa gcgccacaga tcctccggcg acgagactcc        1500
accgggtagg cggcaggcca ttcccacgat cgccagcggc tcaagcttcg                   1550
```